(12) United States Patent
Matsuzaki

(10) Patent No.: US 11,638,695 B2
(45) Date of Patent: May 2, 2023

(54) DEVELOPMENT OF METHOD AND APPARATUS FOR PRODUCING LIPID PARTICLES HAVING DESIRED PARTICLE DIAMETER

(71) Applicant: OSAKA UNIVERSITY, Osaka (JP)

(72) Inventor: Takashi Matsuzaki, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 262 days.

(21) Appl. No.: 16/760,440

(22) PCT Filed: Oct. 31, 2018

(86) PCT No.: PCT/JP2018/040574
§ 371 (c)(1),
(2) Date: Apr. 27, 2021

(87) PCT Pub. No.: WO2019/088193
PCT Pub. Date: May 9, 2019

(65) Prior Publication Data
US 2021/0259971 A1    Aug. 26, 2021

(30) Foreign Application Priority Data

Nov. 1, 2017 (JP) .............................. JP2017-212020

(51) Int. Cl.
*A61K 9/127* (2006.01)
*A61K 45/06* (2006.01)
(Continued)

(52) U.S. Cl.
CPC ............ *A61K 9/1277* (2013.01); *A61K 45/06* (2013.01); *B01D 61/28* (2013.01); *B01D 61/32* (2013.01); *B01D 63/02* (2013.01)

(58) Field of Classification Search
CPC ........ A61K 9/1277; A61K 45/06; A61K 9/10; A61K 8/14; A61K 9/1075; A61K 9/127;
(Continued)

(56) References Cited

U.S. PATENT DOCUMENTS 5,700,482 A    12/1997  Frederiksen et al.
6,596,305 B1*   7/2003  Edgerly-Plug ....... A61K 9/1277
                                                     264/4.1
(Continued)

FOREIGN PATENT DOCUMENTS

CN    1338923 A    3/2002
EP    0616801 A1   9/1994
(Continued)

OTHER PUBLICATIONS

International Search Report for related International Application No. PCT/JP2018/040574 dated Feb. 5, 2019.
(Continued)

*Primary Examiner* — Krishnan S Menon
(74) *Attorney, Agent, or Firm* — Renner, Otto, Boisselle & Sklar, LLP

(57) ABSTRACT

The present invention provides a method for producing lipid particles that have a desired particle diameter, the method comprising: (A) a step for preparing, in a first mixing region, a primary dilution by mixing a first solution containing a lipid and an alcohol with a second solution containing water; (B) a step for feeding the primary dilution from the first mixing region to a second mixing region through a liquid feed pipe within a prescribed time; and (C) a step for preparing a secondary dilution by mixing the primary dilution with a third solution containing water in the second mixing region, wherein the steps (A)-(C) are continuously carried out, and the particle diameter of the lipid particles is controlled by adjusting at least one condition selected from
(Continued)

the group consisting of the concentration of the alcohol and the concentration of the lipid in the primary dilution, the prescribed time, and the temperature during mixing.

14 Claims, 30 Drawing Sheets

(51) Int. Cl.
  *B01D 61/28* (2006.01)
  *B01D 61/32* (2006.01)
  *B01D 63/02* (2006.01)
(58) Field of Classification Search
  CPC ........ B01D 61/28; B01D 61/32; B01D 63/02; B01J 13/04; A23L 5/00
  See application file for complete search history.

(56) References Cited

U.S. PATENT DOCUMENTS

| | | |
|---|---|---|
| 7,901,708 B2 | 3/2011 | MacLachlan et al. |
| 2017/0232390 A1 | 8/2017 | Matsuzaki et al. |

FOREIGN PATENT DOCUMENTS

| | | |
|---|---|---|
| JP | 2002-536316 A | 10/2002 |
| JP | 2005-538967 A | 12/2005 |
| WO | 00/45791 A2 | 8/2000 |
| WO | 2004/002453 A1 | 1/2004 |
| WO | 2011140627 A1 | 11/2011 |
| WO | 2013064911 A2 | 5/2013 |
| WO | 2016/024510 A1 | 2/2016 |
| WO | 2016149625 A1 | 9/2016 |

OTHER PUBLICATIONS

Brief Communication and corrected Written Opinion for corresponding European Application No. 18871997.5 dated Nov. 26, 2020.
Second Office Action for corresponding Chinese Application No. 201880085075.0 dated May 7, 2022 and its English Translation.
Extended European Search Report and Search Opinion for corresponding European Application No. 18871997.5 dated Oct. 8, 2020.
Office Action for corresponding Japanese Application No. 2019-550468 dated Apr. 30, 2021 and its English translation.
First Office Action for corresponding Chinese Application No. 201880085075.0 dated Nov. 15, 2021 and its English Translation.
Communication pursuant to Article 94(3) EPC for corresponding European Application No. 18871997.5 dated Oct. 20, 2021.
Office Action for corresponding Japanese Application No. 2019-550468 dated Sep. 27, 2021 and its English Machine Translation.
Decision to Grant a Patent for corresponding Japanese Application No. 2019-550468 dated Oct. 13, 2021 and its English Machine Translation.
Third Office Action for corresponding Chinese Application No. 201880085075.0 dated Nov. 3, 2022 and its English Translation.

* cited by examiner

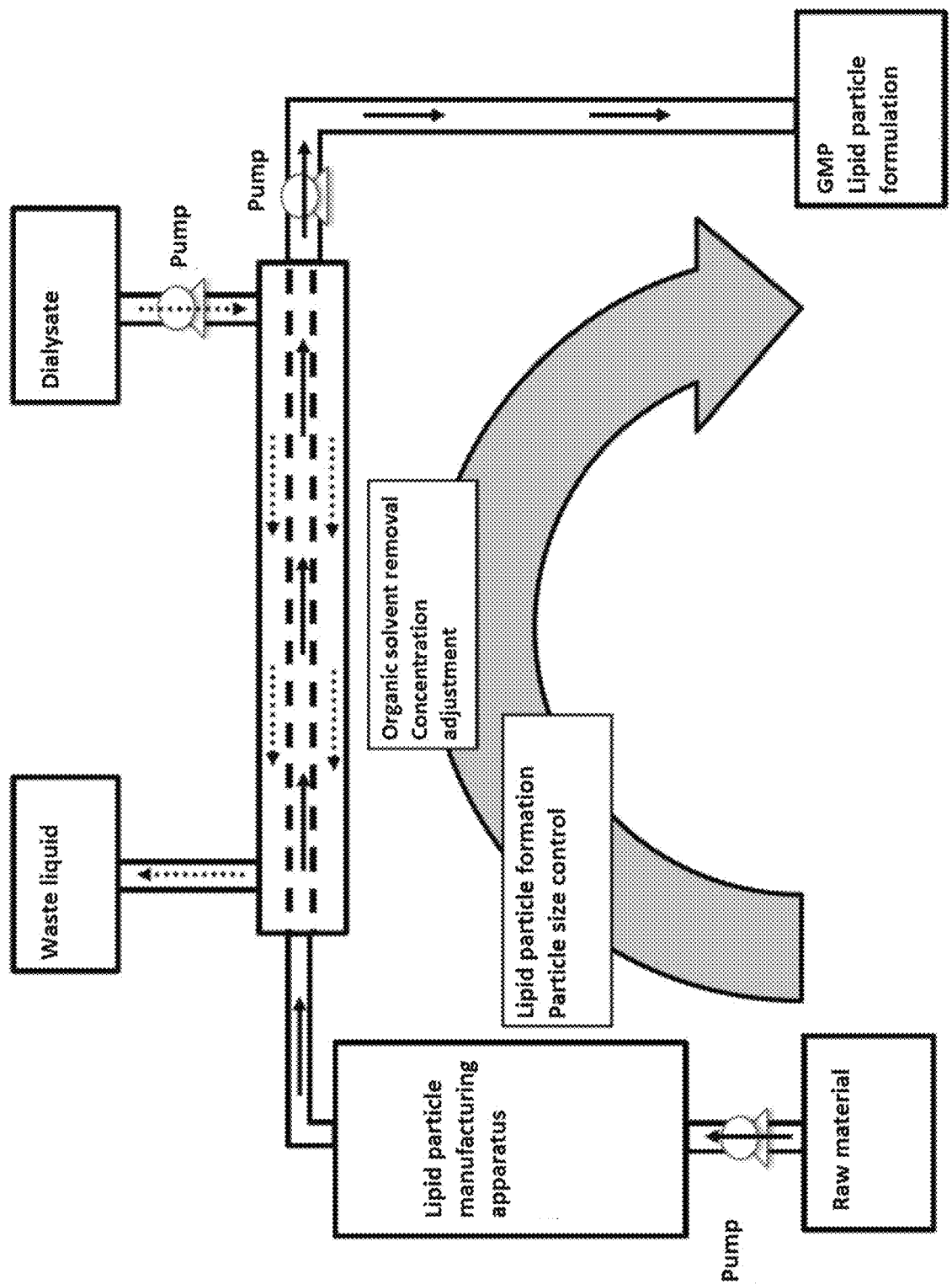

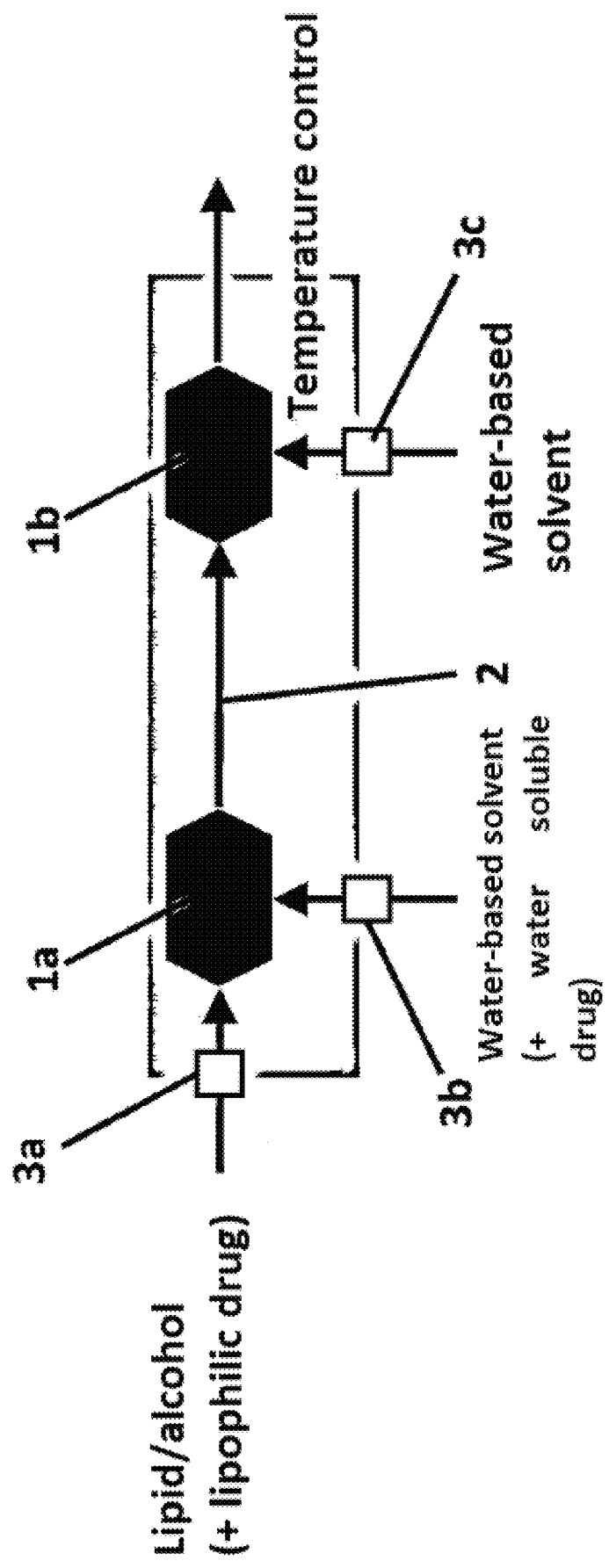

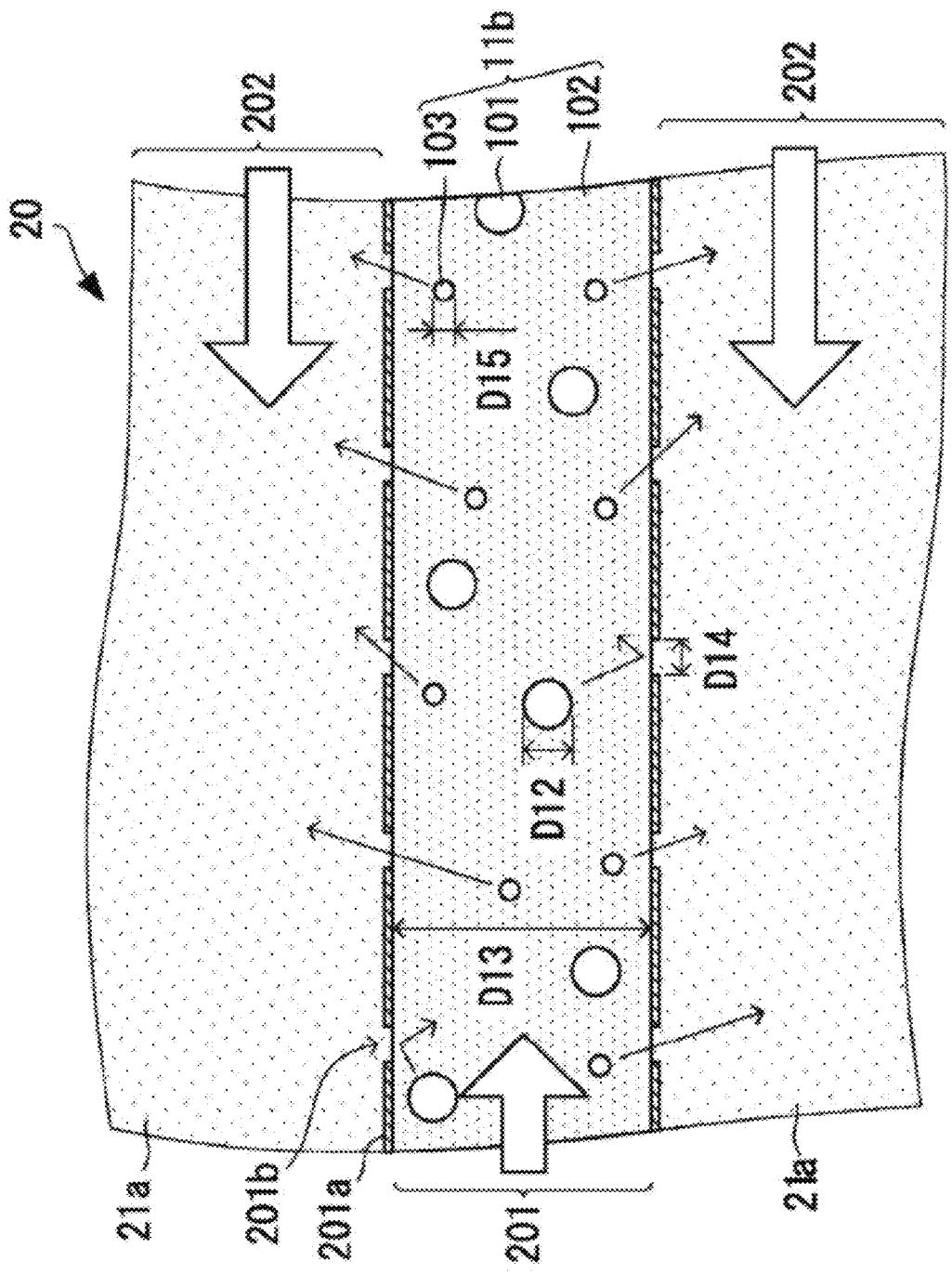

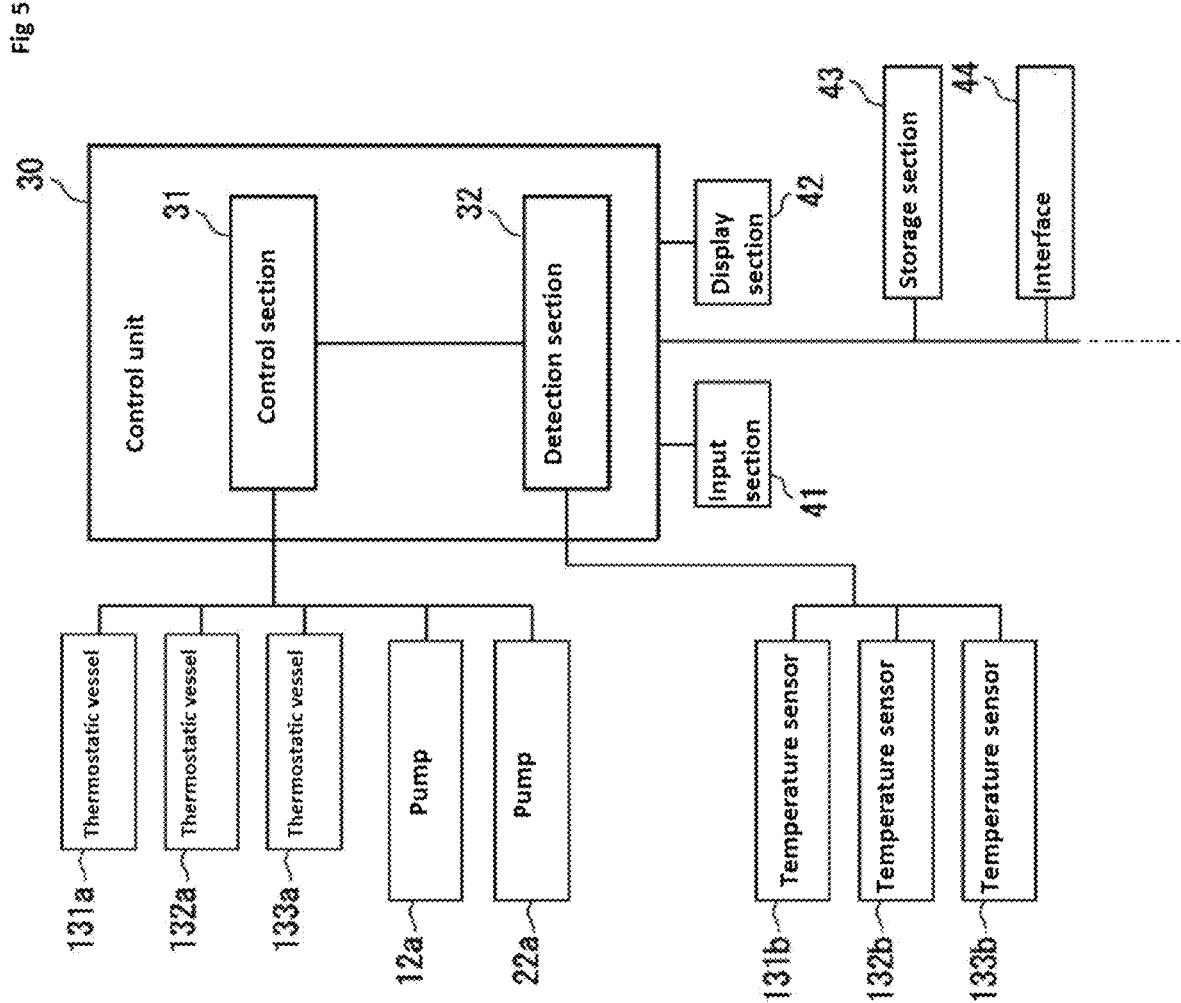

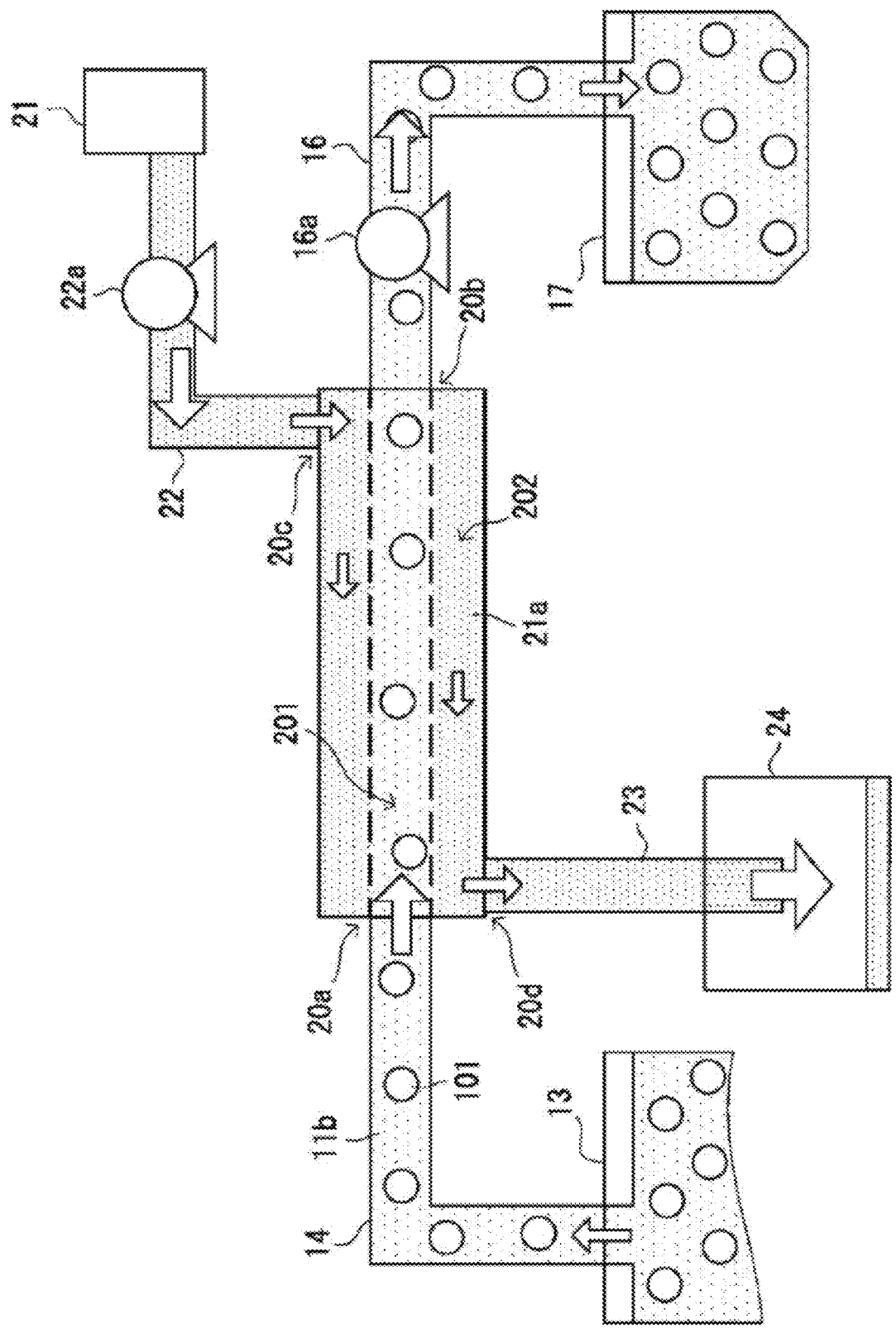

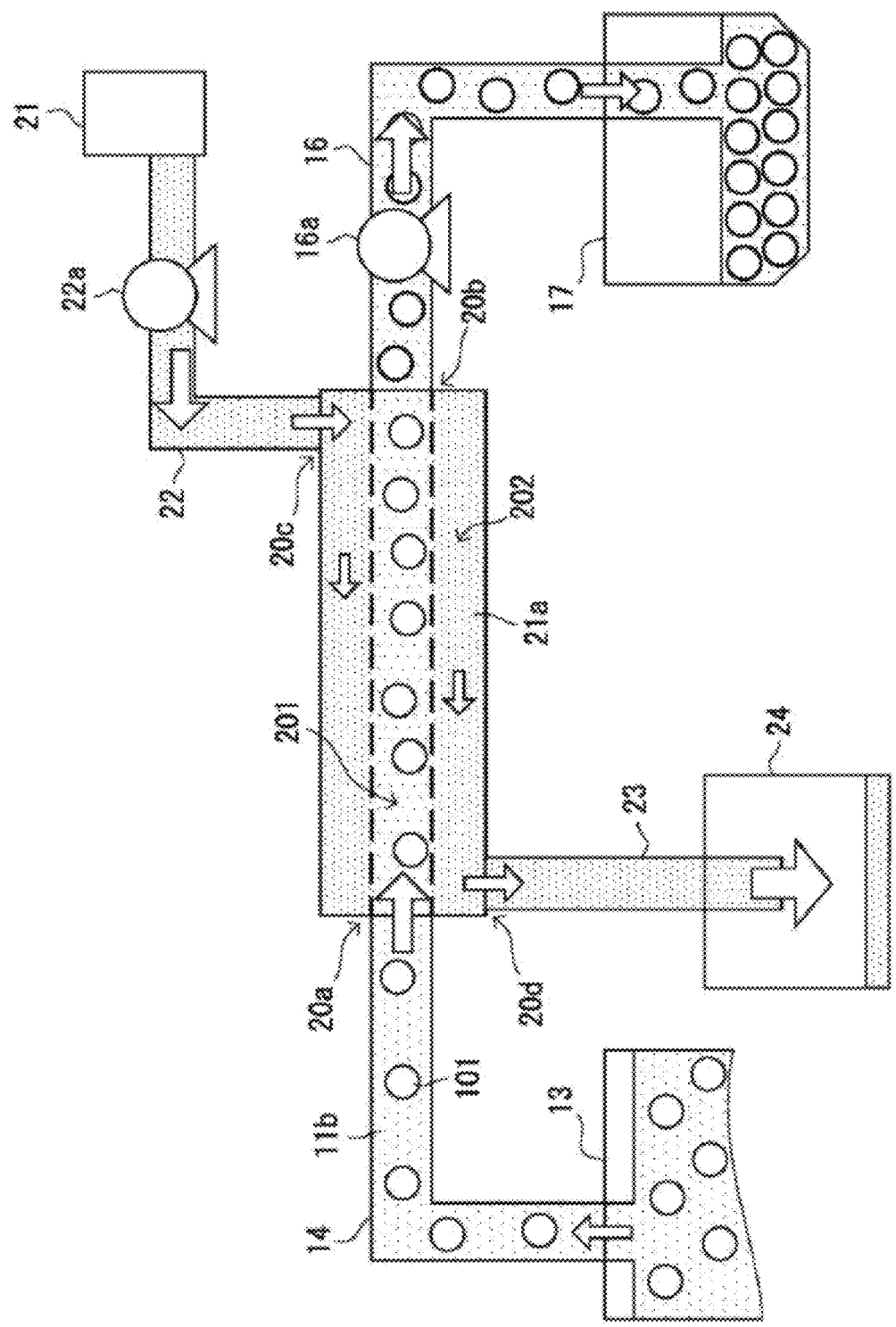

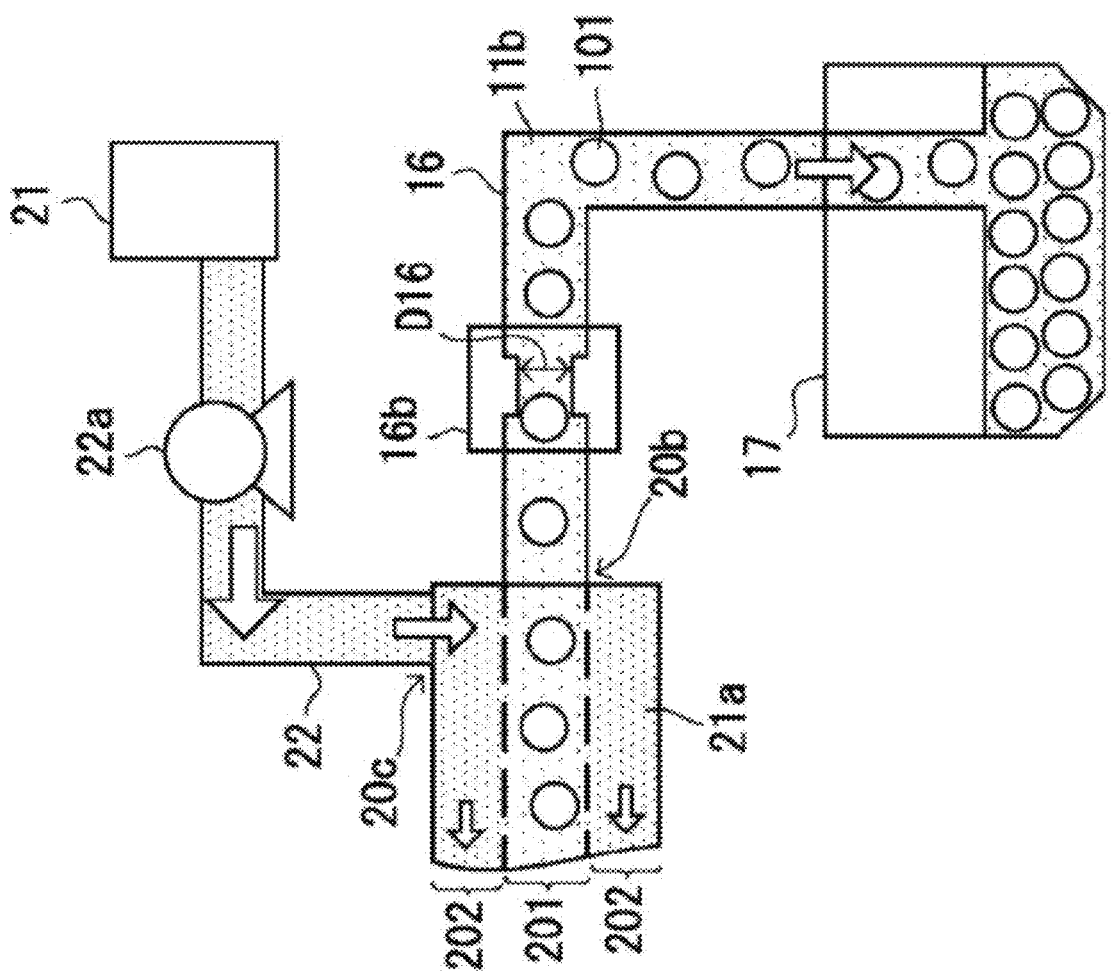

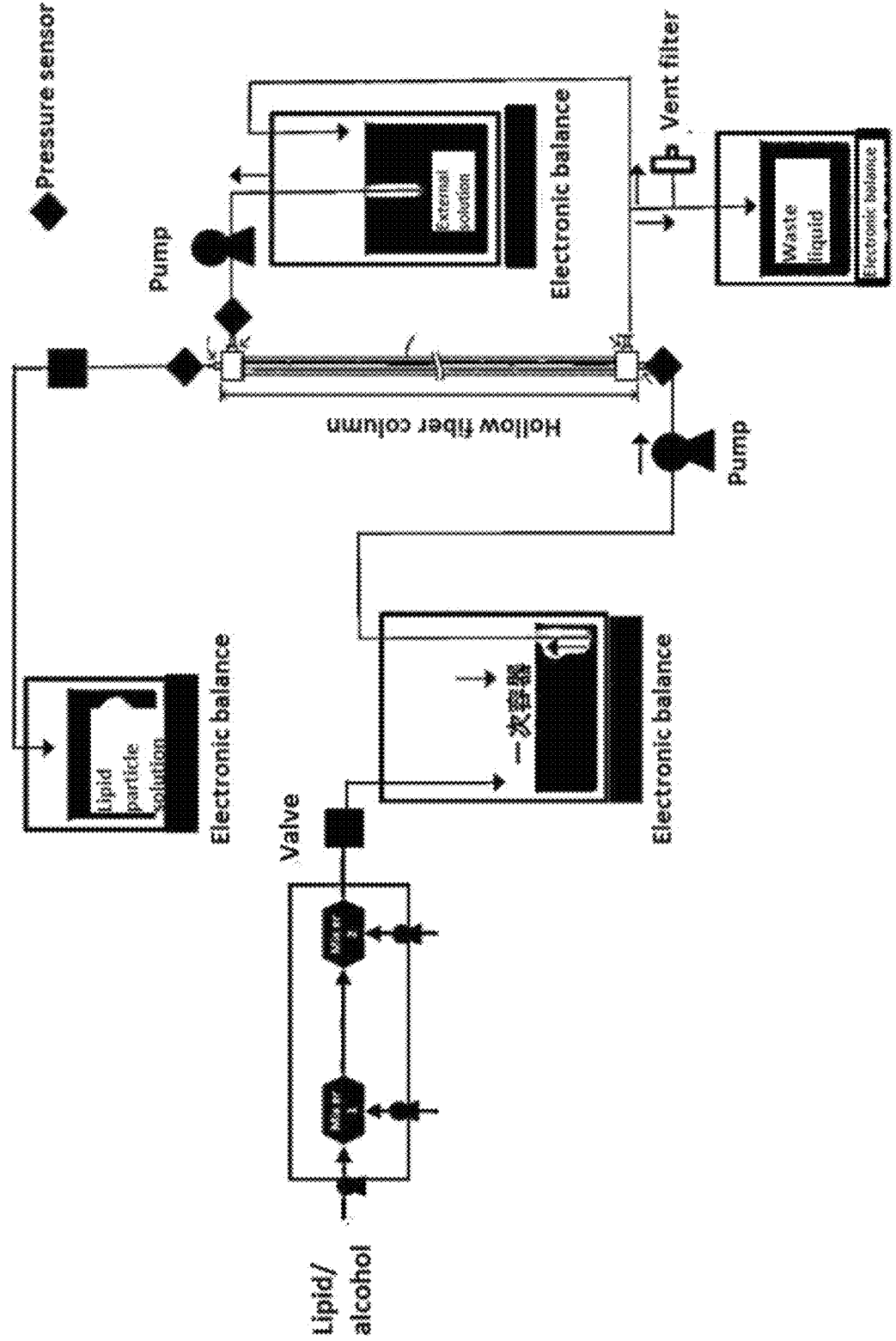

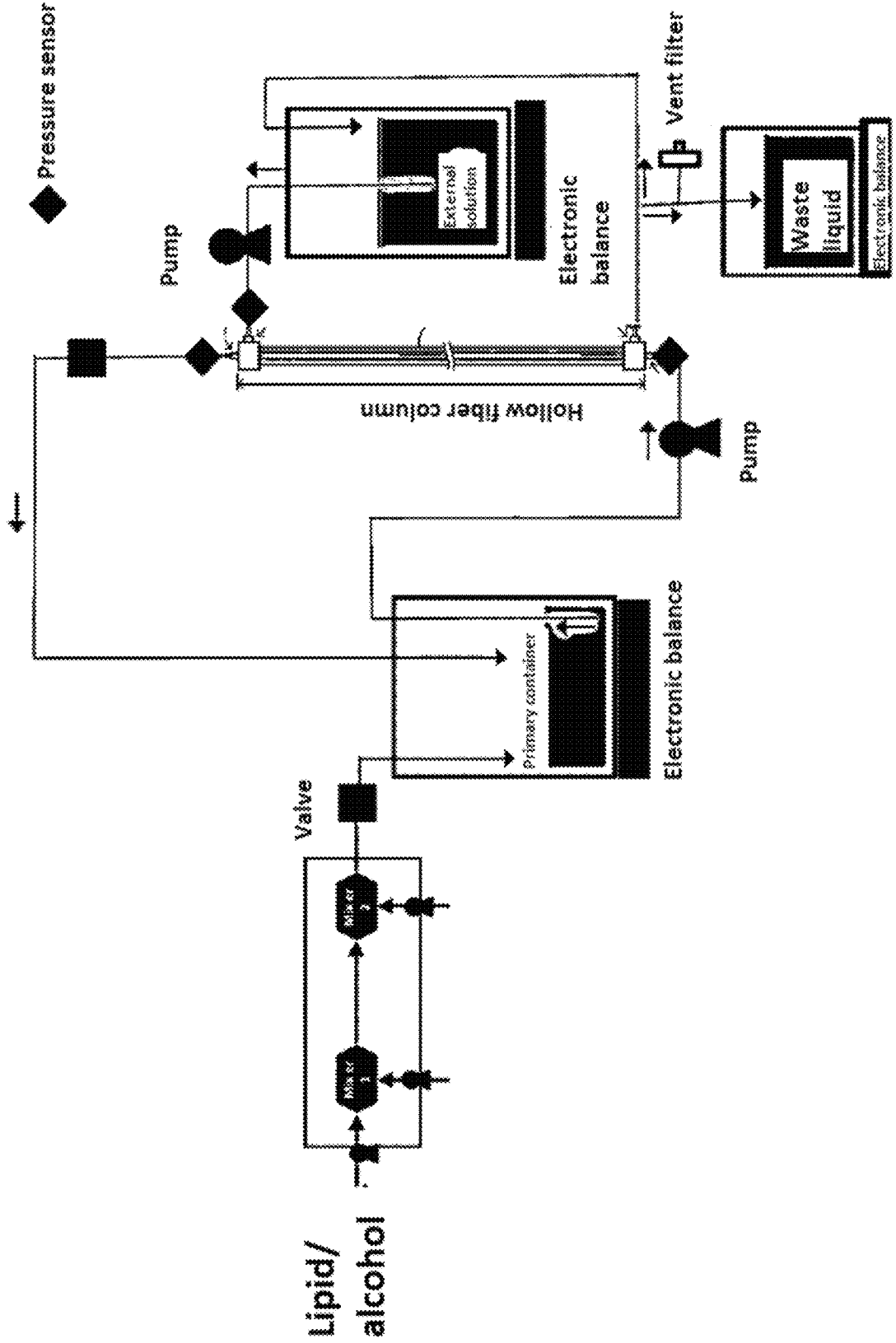

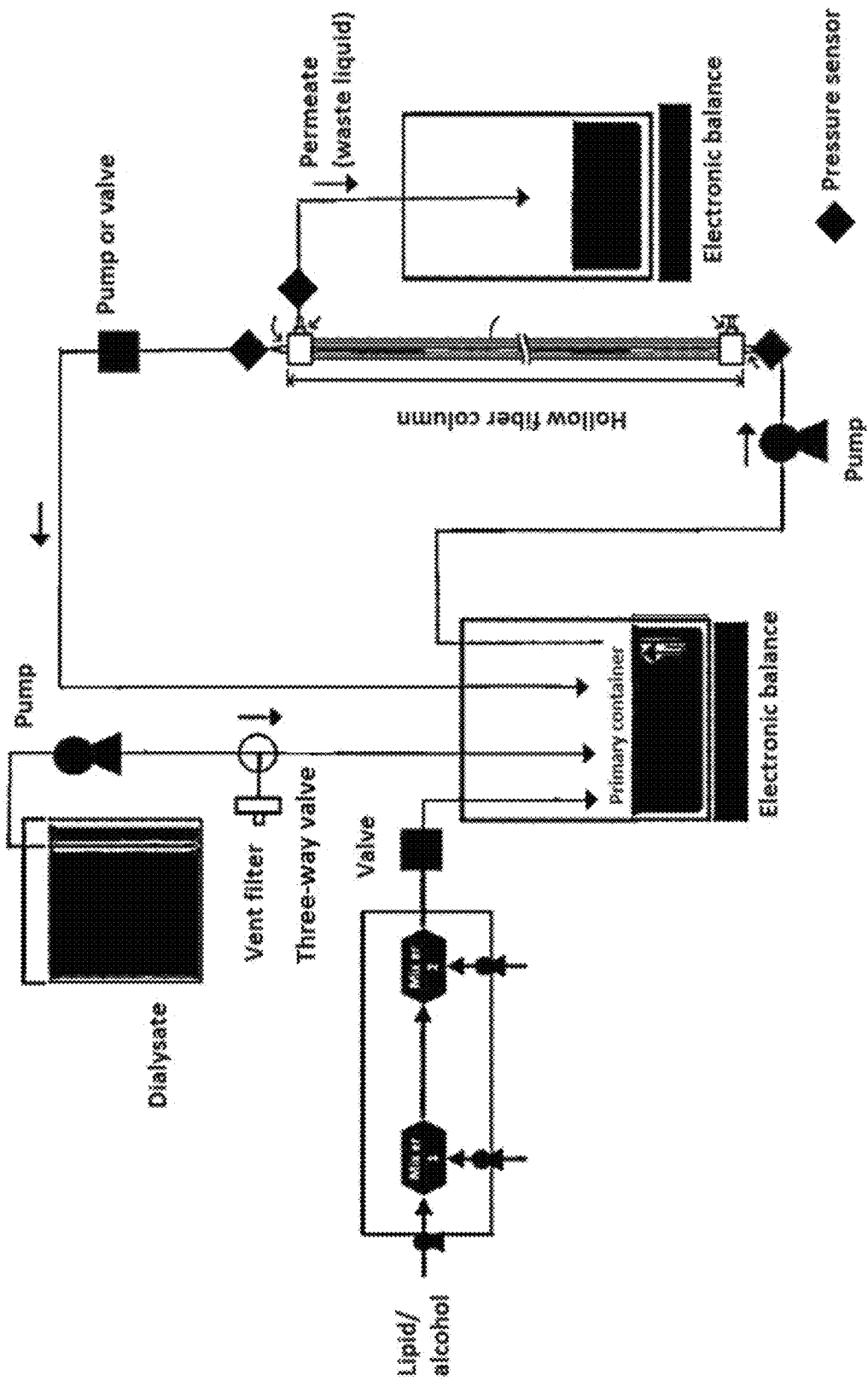

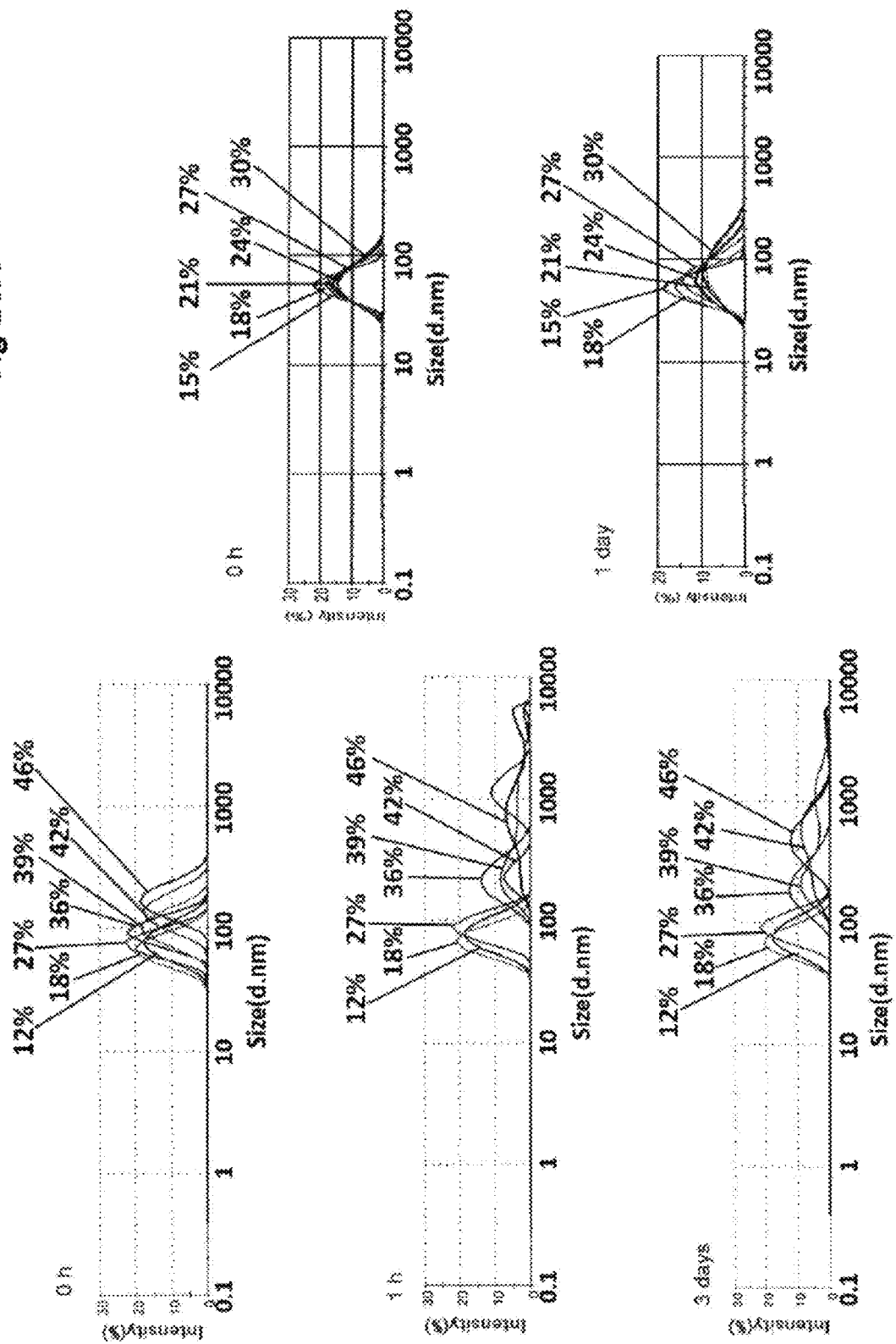

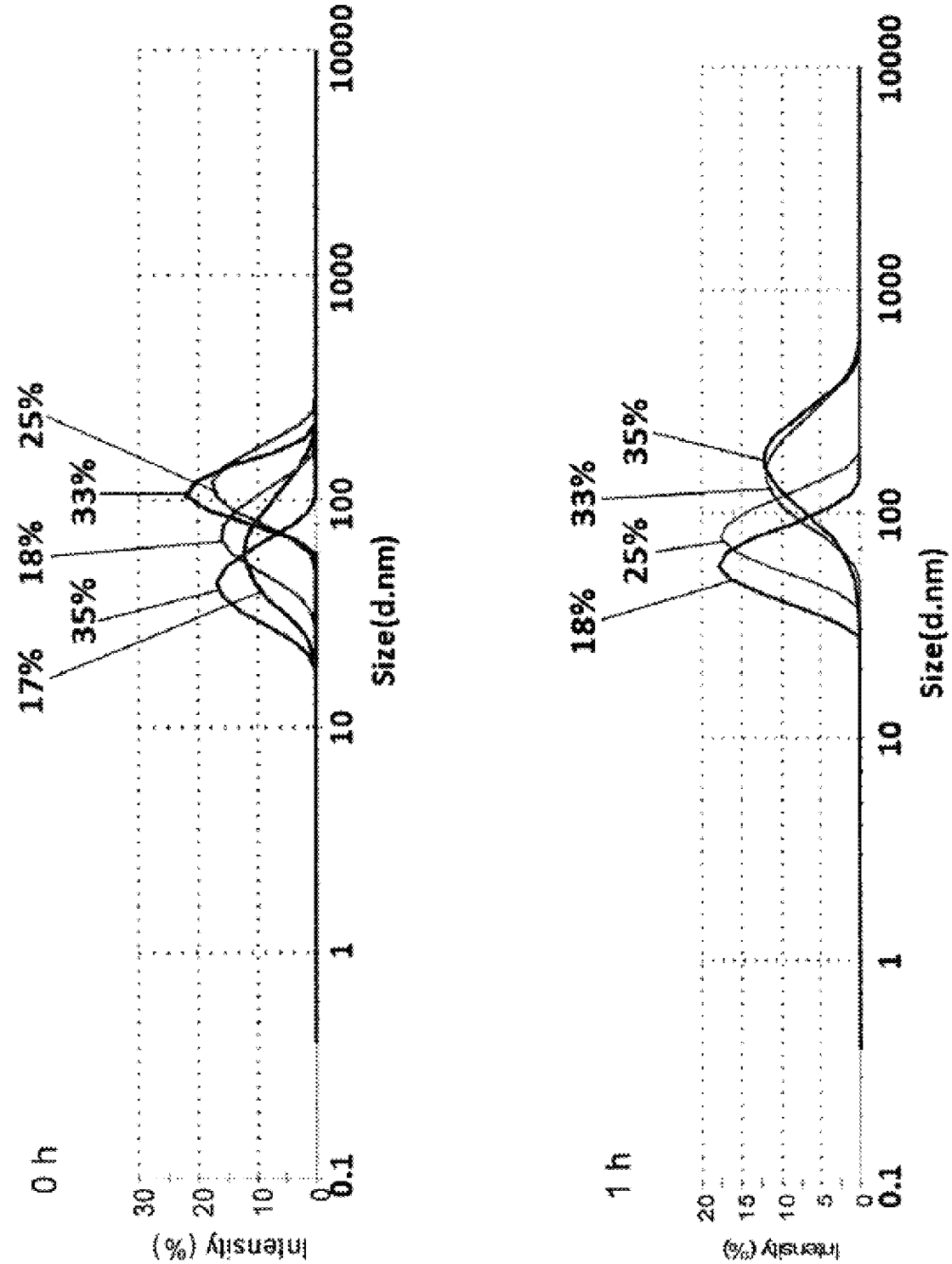

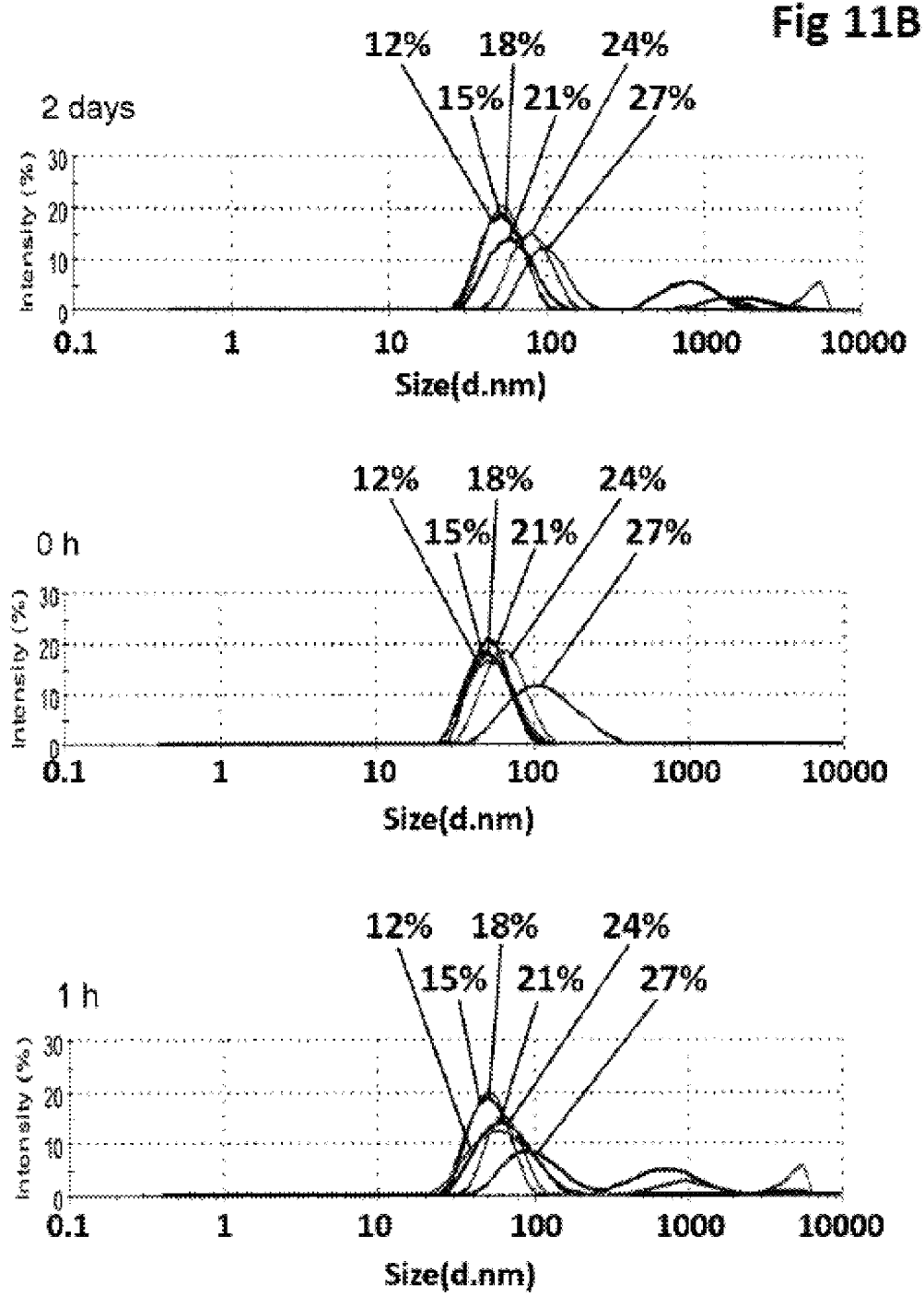

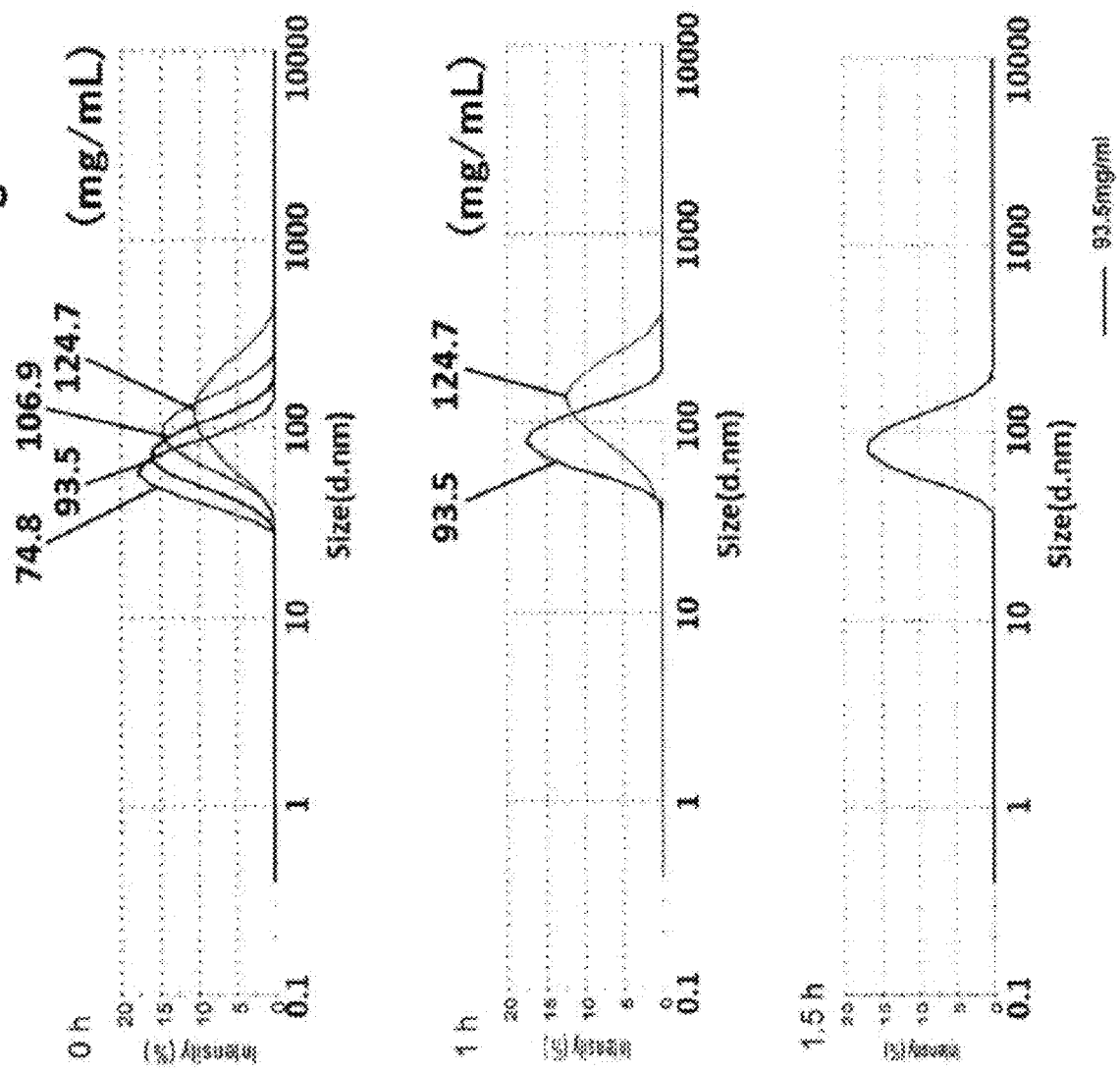

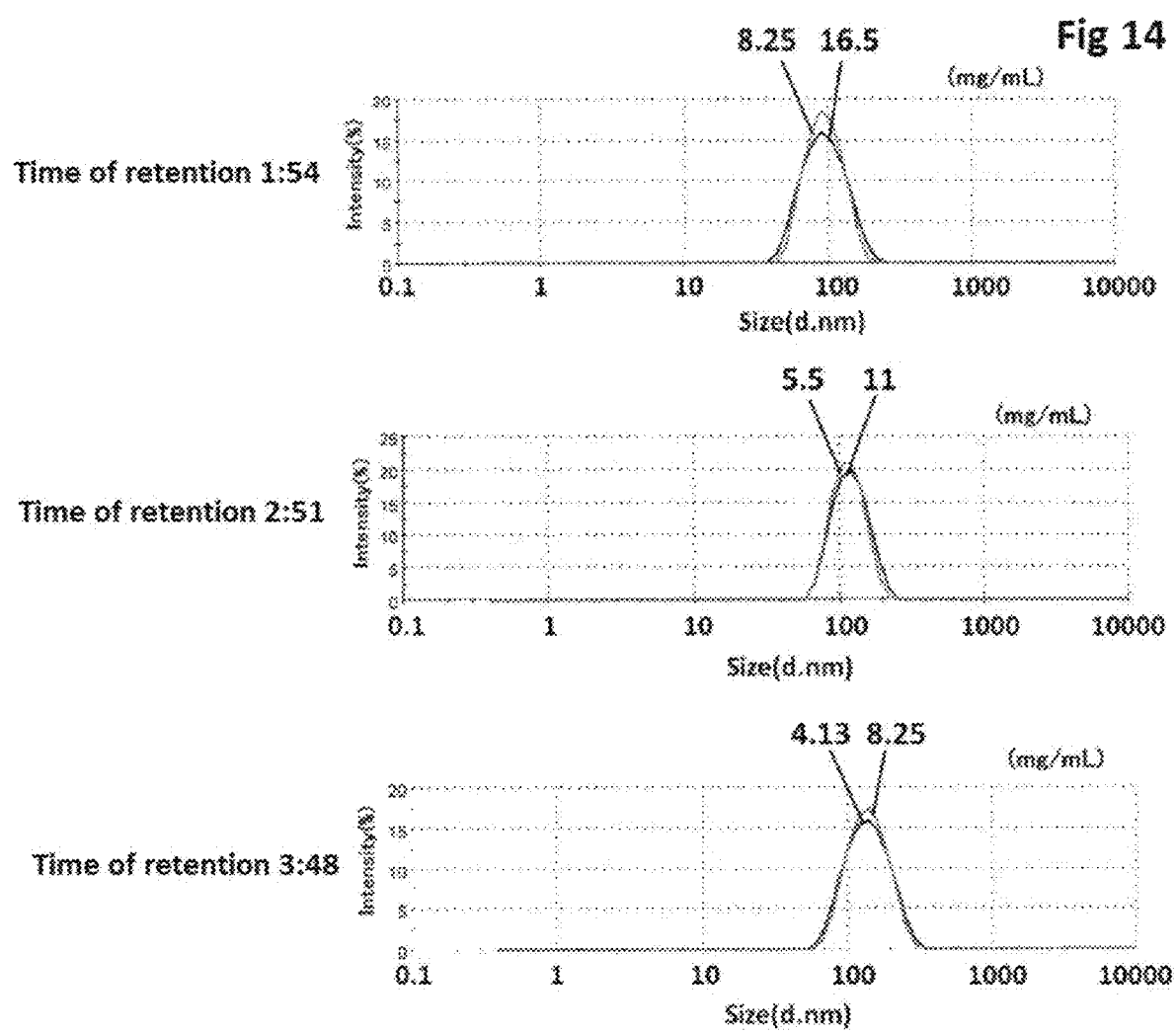

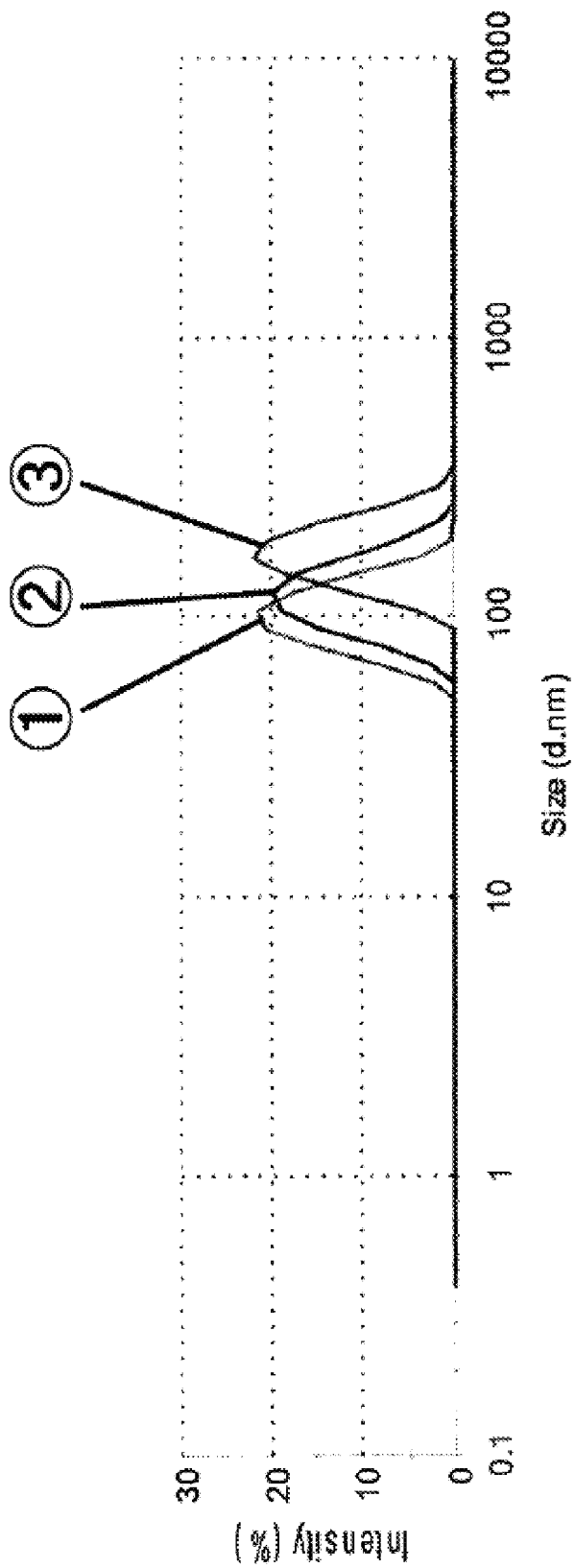

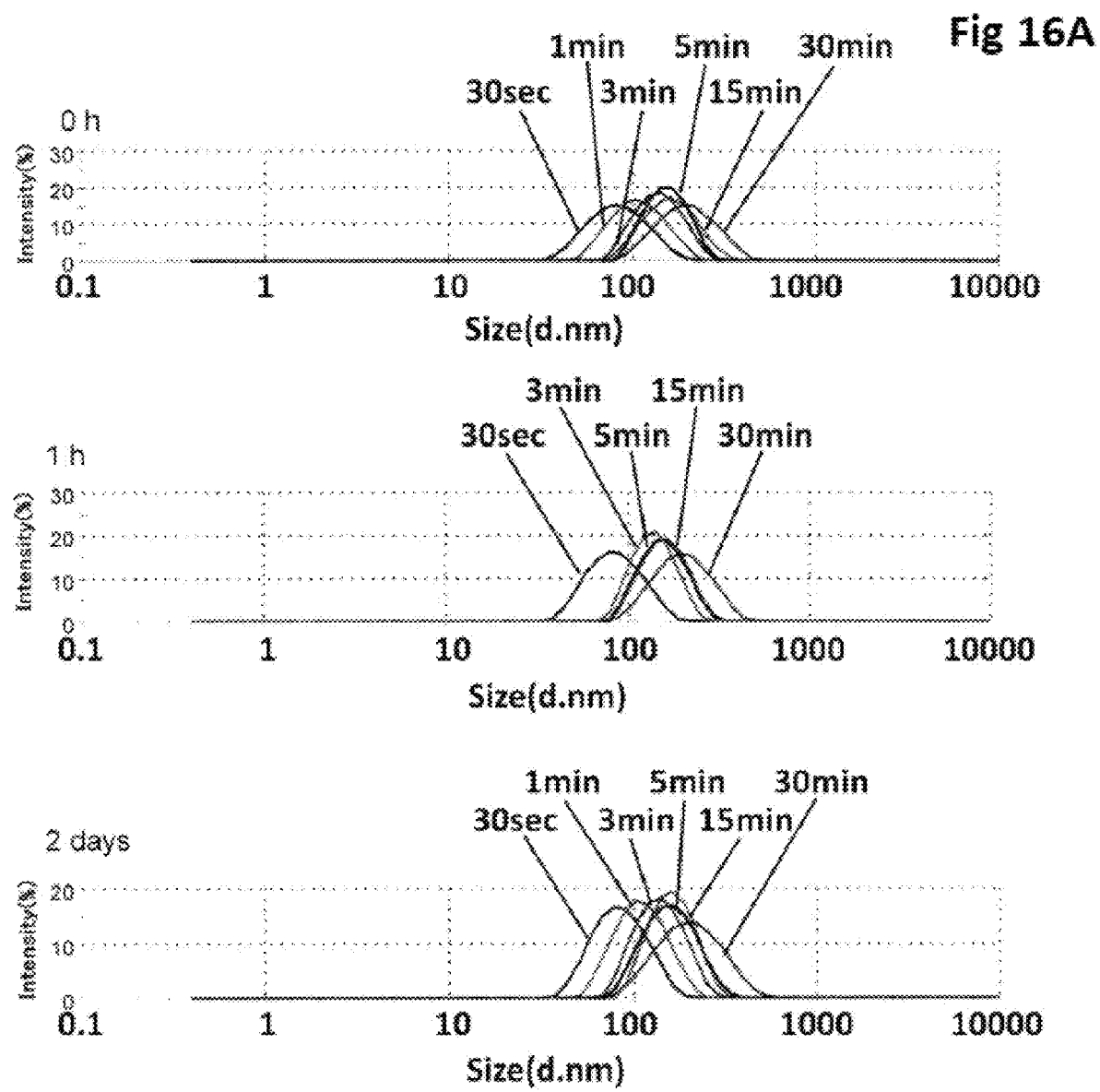

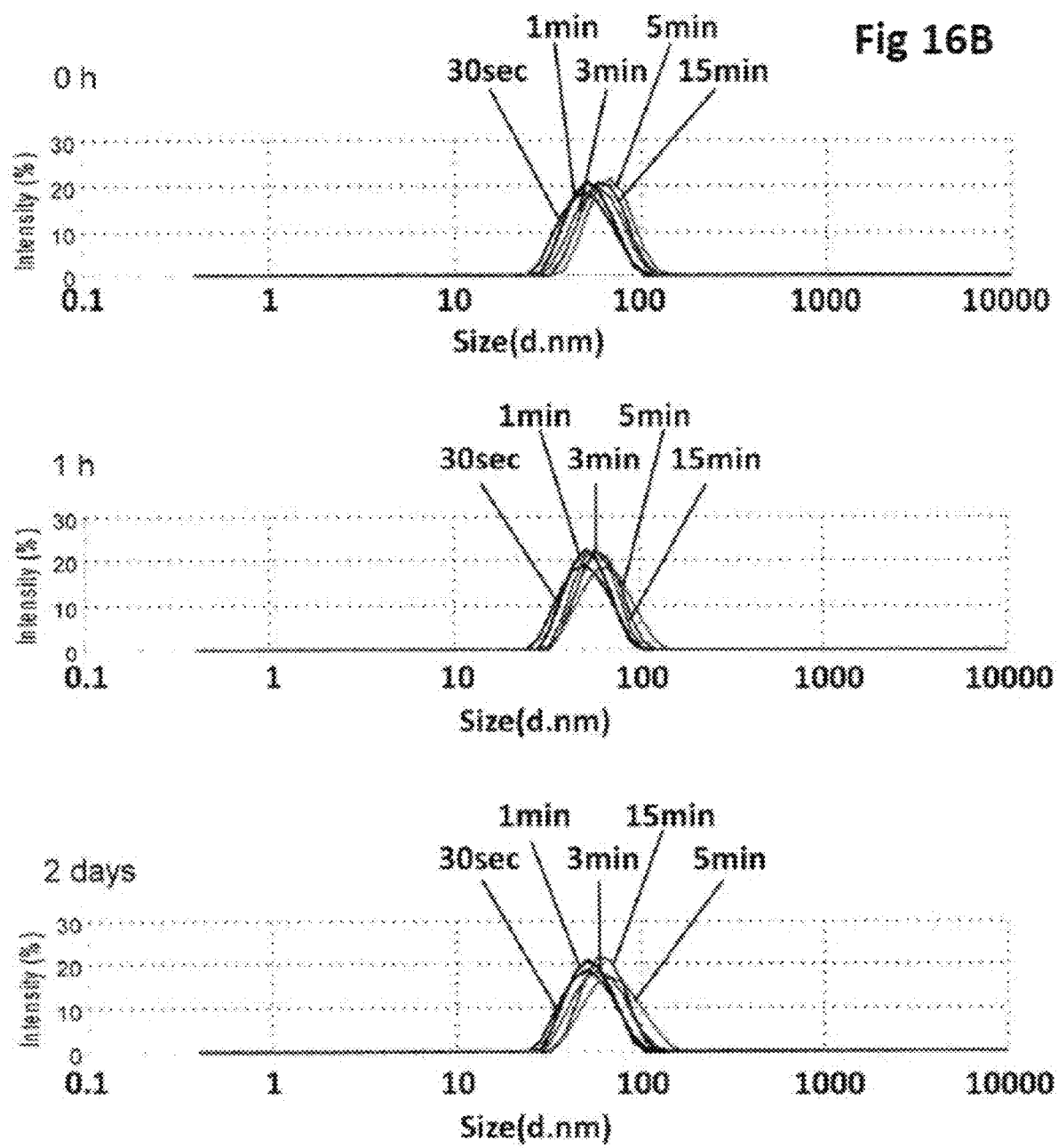

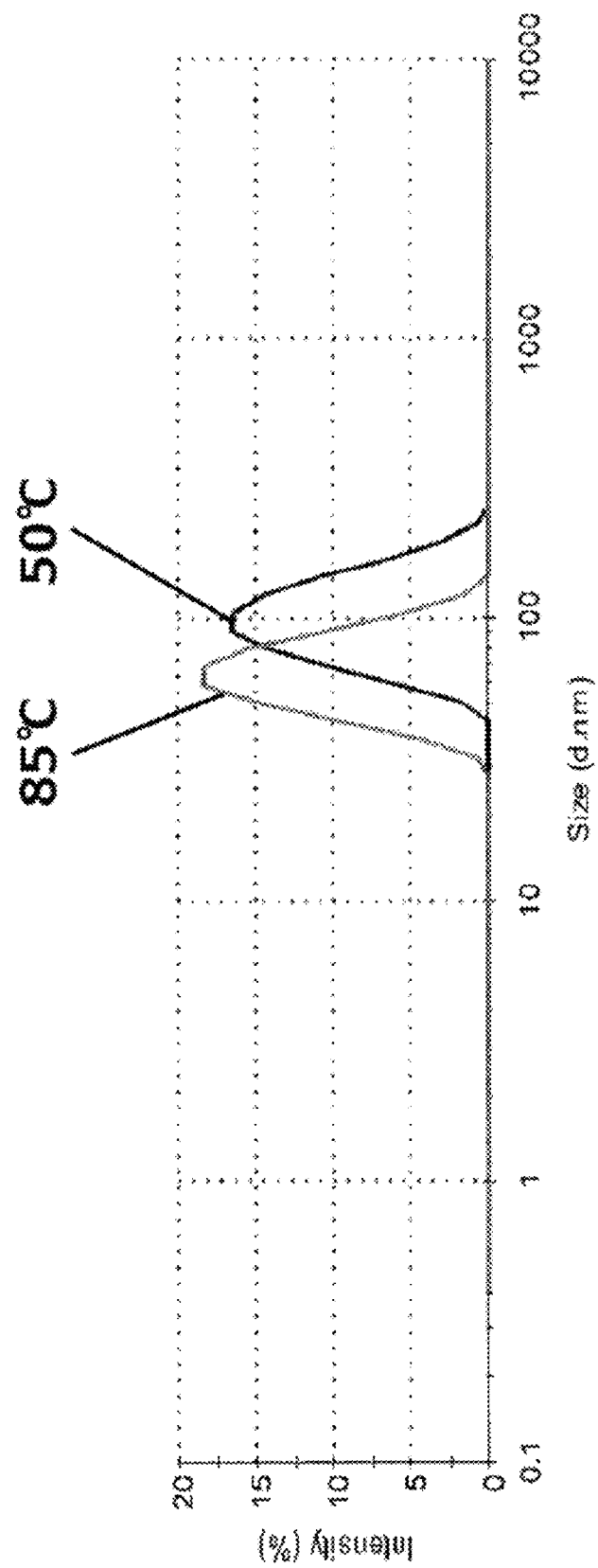

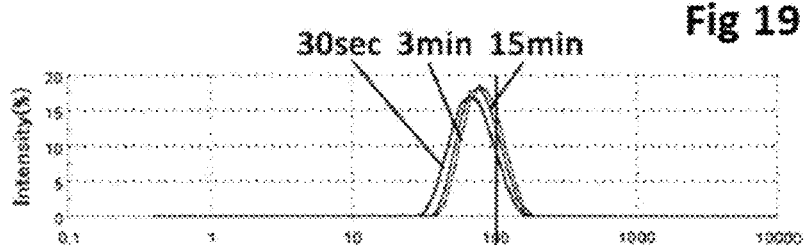
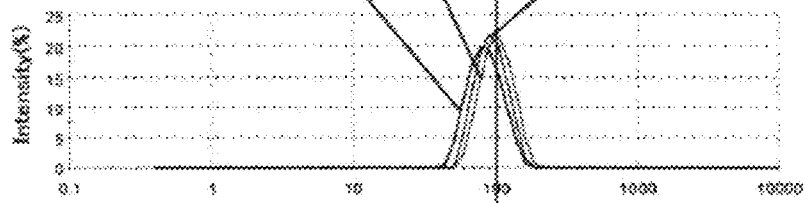
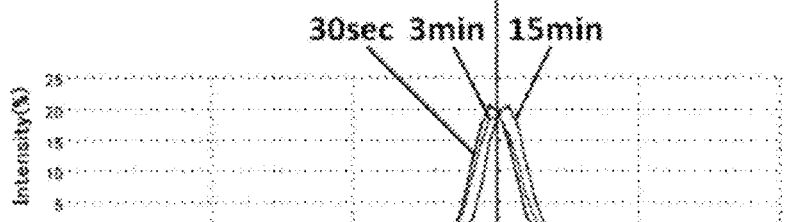
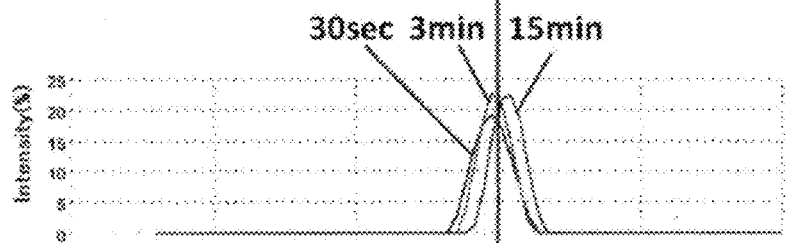
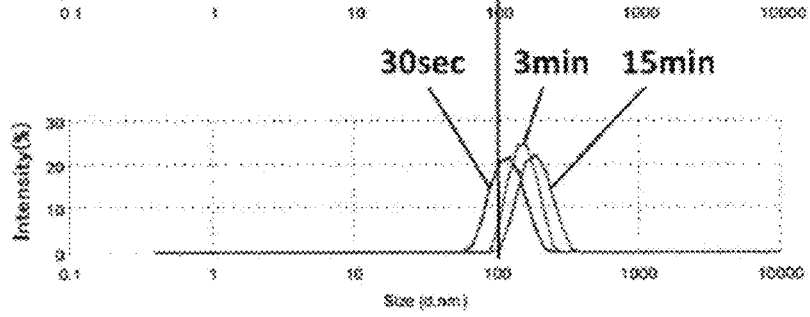
Fig 19

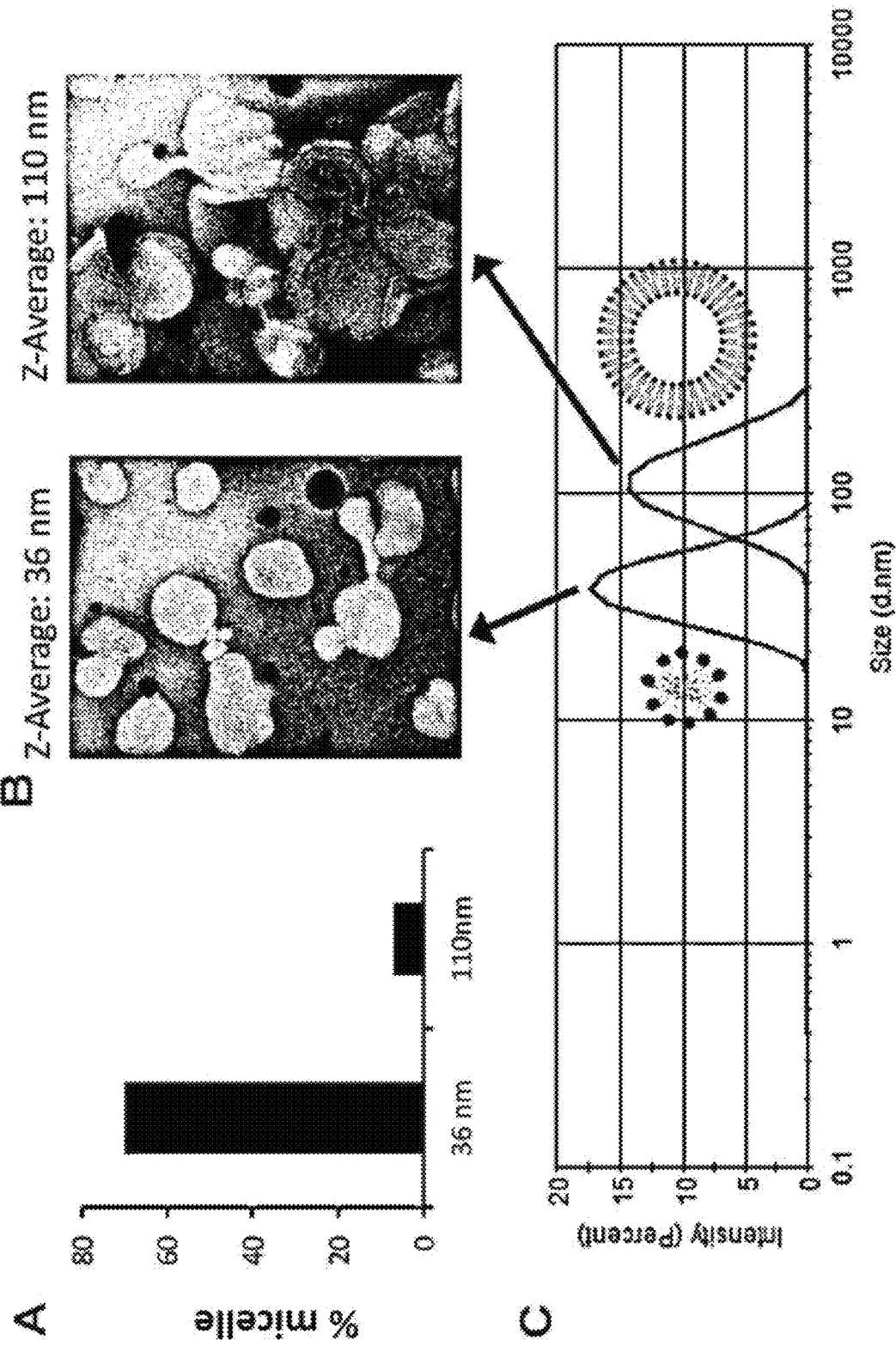

DEVELOPMENT OF METHOD AND APPARATUS FOR PRODUCING LIPID PARTICLES HAVING DESIRED PARTICLE DIAMETER

TECHNICAL FIELD

The present invention relates to a method and apparatus for manufacturing lipid particles with a desired particle size. More specifically, the present invention relates to a technology for manufacturing lipid particles with a desired particle size by serially diluting a solution comprising a lipid.

BACKGROUND ART

"Inline liposome manufacturing technology" that enables continuous liposome formation within a closed fine tube has drawn attention as a technology for producing aseptic lipid particles. Development of a technology for adjusting the concentration of formed liposomes inline is ongoing (Cited Reference 1). However, different conditions must be considered in order to attain the same particle size if the composition of phospholipid or the drug to be loaded is different. Therefore, inline manufacture of lipid particles with a uniform particle size using phospholipids having a desired structure was challenging.

One of the conventional lipid particle manufacturing methods, "ethanol injection", is a manufacturing method of lipid particles, which injects or adds dropwise ethanol with phospholipids dissolved therein into a water-based solvent and utilizes bilayer formation due to self-organization of phospholipids in the water-based solvent. The lipid particles manufactured by such a method resulted in uneven particle sizes.

CITATION LIST

Patent Literature

[PTL 1] International Publication No. WO 2016/024510

SUMMARY OF INVENTION

Solution to Problem

The present invention focuses on lipid particles becoming unstable in the presence of a high concentration of alcohol to perform a primary dilution of an alcohol containing a solution with lipids dissolved therein at an alcohol concentration where lipid particles become unstable, and then perform a secondary dilution to obtain stabilized lipid particles. In this regard, it was found that the particle size of the lipid particles can be controlled while maintaining a uniform granularity distribution by adjusting the time of retention from the primary dilution to the secondary dilution.

Therefore, the present invention provides the following.
(Item X1)
A method of manufacturing a lipid particle with a desired particle size, the method comprising:
(A) preparing a primary diluting solution by mixing a first solution comprising a lipid and alcohol with a second solution comprising water in a first mixing region;
(B) supplying the primary diluting solution from the first mixing region to a second mixing region through a liquid supplying tube in a predetermined time; and
(C) preparing a secondary diluting solution by mixing the primary diluting solution with a third solution comprising water in the second mixing region;
wherein steps (A) to (C) are performed sequentially, and
wherein a particle size of a lipid particle is controlled by adjusting at least one condition selected from the group consisting of a concentration of the alcohol in the primary diluting solution, a concentration of the lipid, the predetermined time, and a temperature upon the mixing.
(Item X2)
The method of item X1, wherein the lipid particle is a liposome or micelle.
(Item X3)
The method of item X1, wherein the lipid particle is a liposome.
(Item X4)
The method of any one of items X1 to X3, wherein the lipid particle is further loaded with a drug, the method further comprising, before step (A):
(A-1) measuring a particle size of a lipid particle formed when a concentration of the alcohol is changed by diluting a solution comprising the drug, the lipid, and the alcohol; and
(A-2) measuring a chronological change in a particle size of a lipid particle loaded with the drug under a condition where the concentration of the alcohol is constant;
wherein at least one condition required for adjusting the desired particle size selected from the group consisting of the concentration of the alcohol in the primary diluting solution, the concentration of the lipid, the predetermined time, and the temperature upon the mixing is determined based on information obtained by steps (A-1) and (A-2).
(Item X5)
The method of any one of items X1 to X4, wherein the alcohol concentration in the primary diluting solution is adjusted to 18 wt % or greater.
(Item X6)
The method of any one of items X1 to X5, wherein steps (A) to (C) are performed in a closed system.
(Item X7)
The method of any one of items X1 to X6, wherein additional particle size controlling processing is not performed after step (C).
(Item X8)
The method of any one of items X1 to X7, wherein the predetermined time is adjusted by at least one of a length of the liquid supplying tube and a flow rate.
(Item X9)
The method of any one of items X1 to X8, wherein a pressure in the liquid supplying tube is 1 MPa or greater.
(Item X10)
The method of any one of items X1 to X9, wherein the secondary diluting solution is further supplied to a hollow fiber membrane column.
(Item X11)
A system for manufacturing a lipid particle with a desired particle size, the system comprising:
(A) a first mixing region for preparing a primary diluting solution by mixing a first solution comprising a lipid and alcohol with a second solution comprising water;
(B) a second mixing region for preparing a secondary diluting solution by mixing the primary diluting solution with a third solution comprising water; and
(C) a liquid supplying tube for supplying the primary diluting solution from the first mixing region to the second mixing region in a predetermined time;

wherein a particle size of a lipid particle is controlled by adjusting at least one condition selected from the group consisting of a concentration of the alcohol in the primary diluting solution, a concentration of the lipid, the predetermined time, and a temperature upon the mixing.

(Item X12)

The system of item X11, wherein the lipid particle is a liposome or micelle.

(Item X13)

The system of item X11, wherein the lipid particle is a liposome.

(Item X14)

The system of any one of items X11 to X13, wherein the lipid particle is further loaded with a drug, the system further comprising a control section for performing:

(A-1) measuring a particle size of a lipid particle formed when a concentration of the alcohol is changed by diluting a solution comprising the drug, the lipid, and the alcohol; and (A-2) measuring a chronological change in a particle size of a lipid particle loaded with the drug under a condition where the concentration of the alcohol is constant;

wherein the control section determines at least one condition selected from the group consisting of the concentration of the alcohol in the primary diluting solution, the concentration of the lipid, the predetermined time, and the temperature upon the mixing based on information obtained by steps (A-1) and (A-2).

(Item X15)

The system of any one of items X11 to X14, wherein an alcohol concentration in the primary diluting solution is adjusted to 18 wt % or greater.

(Item X16)

A system for manufacturing a lipid particle with a desired particle size, the system comprising:

(1) a lipid particle manufacturing apparatus; and (2) a dialyzer, wherein the particle size manufacturing apparatus comprises:

(1-A) a first mixing region for preparing a primary diluting solution by mixing a first solution comprising a lipid and alcohol with a second solution comprising water;

(1-B) a second mixing region for preparing a secondary diluting solution by mixing the primary diluting solution with a third solution comprising water; and (1-C) a liquid supplying tube for supplying the primary diluting solution from the first mixing region to the second mixing region in a predetermined time;

wherein a particle size of a lipid particle is controlled by adjusting at least one condition selected from the group consisting of a concentration of the alcohol in the primary diluting solution, a concentration of the lipid, the predetermined time, and a temperature upon the mixing, and the dialyzer comprises:

(2-A) a hollow fiber dialysis column having a hollow fiber membrane and a first flow channel where a solution subjected to dialysis flows inside the hollow fiber membrane;

(2-B) a liquid supplying section for supplying the solution subjected to dialysis to an inlet of the first flow channel; and (2-C) a second flow channel having a portion in contact with the hollow fiber membrane.

(Item X17)

The system of item X16, wherein the lipid particle is a liposome or a micelle.

(Item X18)

The system of item X16, wherein the lipid particles is a liposome.

(Item X19)

The system of any one of items X16 to X18, wherein the second flow channel is a flow channel where an external solution flows outside the hollow fiber membrane.

(Item X20)

The system of any one of items X16 to X18, wherein the second flow channel is a flow channel where a filtrate of the hollow fiber membrane flows.

(Item X21)

The system of item X20, comprising a third flow channel for adding an external solution to the solution subjected to dialysis.

(Item X22)

The system of any one of items X16 to X21, comprising a solution storage container, wherein the solution storage container is connected to the lipid particle manufacturing apparatus and the dialyzer, and the solution storage container stores a lipid particle containing solution flowing in from the lipid particle manufacturing apparatus.

(Item X23)

The system of any one of items X16 to X22, wherein the dialyzer comprises (2-D) a flow rate/pressure varying section, which can change a flow rate and/or pressure of the solution subjected to dialysis when flowing out from an outlet of the first flow channel, wherein the flow rate varying section comprises an apparatus, provided downstream of the outlet of the first flow channel, for supplying the solution subjected to dialysis that has flowed out from the outlet of the first flow channel downstream at a lower flow rate and/or lower pressure than a flow rate at the liquid supplying section at the inlet of the first flow channel.

(Item X24)

The system of item X23, wherein the apparatus of the flow rate varying section comprises:

(1) a pump for supplying the solution subjected to dialysis that has flowed out from the outlet of the first flow channel downstream at a predetermined flow rate; or (2) a valve for narrowing a flow channel of the solution subjected to dialysis that has flowed out from the outlet of the first flow channel.

(Item X25)

The system of any one of items X16 to X24, wherein an alcohol concentration in the primary diluting solution is adjusted to 18 wt % or greater.

(Item X26)

The system of any one of items X16 to X25 configured so that the solution subjected to dialysis that has flowed out from the outlet of the first flow channel flows in again.

(Item Y1)

A method of manufacturing a liposome with a desired particle size, the method comprising:

(A) preparing a primary diluting solution by mixing a first solution comprising a lipid and alcohol with a second solution comprising water in a first mixing region;

(B) supplying the primary diluting solution from the first mixing region to a second mixing region through a liquid supplying tube in a predetermined time; and (C) preparing a secondary diluting solution by mixing the primary diluting solution with a third solution comprising water in the second mixing region;

wherein steps (A) to (C) are performed sequentially, and wherein a particle size of a liposome is controlled by adjusting at least one condition selected from the group consisting of a concentration of the alcohol in the primary diluting solution, a concentration of the lipid, the predetermined time, and a temperature upon the mixing.
(Item Y2)

The method of item Y1, wherein the liposome is further loaded with a drug, the method further comprising, before step (A):

(A-1) measuring a particle size of a liposome formed when a concentration of the alcohol is changed by diluting a solution comprising the drug, the lipid, and the alcohol; and
(A-2) measuring a chronological change in a particle size of a liposome loaded with the drug under a condition where the concentration of alcohol is constant;

wherein at least one condition required for adjusting the desired particle size selected from the group consisting of the concentration of the alcohol in the primary diluting solution, the concentration of the lipid, the predetermined time, and the temperature upon the mixing is determined based on information obtained by steps (A-1) and (A-2).
(Item Y3)

The method of item Y1 or Y2, wherein an alcohol concentration in the primary diluting solution is adjusted to 18 wt % or greater.
(Item Y4)

The method of any one of items Y1 to Y3, wherein steps (A) to (C) are performed in a closed system.
(Item Y5)

The method of any one of items Y1 to Y4, wherein additional particle size controlling processing is not performed after step (C).
(Item Y6)

The method of any one of items Y1 to Y5, wherein the predetermined time is adjusted by at least one of a length of the liquid supplying tube and a flow rate.
(Item Y7)

The method of any one of items Y1 to Y6, wherein a pressure in the liquid supplying tube is 1 MPa or greater.
(Item Y8)

The method of any one of items Y1 to Y7, wherein the secondary diluting solution is further supplied to a hollow fiber membrane column.
(Item Y9)

A system for manufacturing a liposome with a desired particle size, the system comprising:
(A) a first mixing region for preparing a primary diluting solution by mixing a first solution comprising a lipid and alcohol with a second solution comprising water;
(B) a second mixing region for preparing a secondary diluting solution by mixing the primary diluting solution with a third solution comprising water; and
(C) a liquid supplying tube for supplying the primary diluting solution from the first mixing region to the second mixing region in a predetermined time;

wherein a particle size of a liposome is controlled by adjusting at least one condition selected from the group consisting of a concentration of the alcohol in the primary diluting solution, a concentration of the lipid, the predetermined time, and a temperature upon the mixing.
(Item Y10)

The system of item Y9, wherein the liposome is further loaded with a drug, the system further comprising a control section for performing:

(A-1) measuring a particle size of a liposome formed when a concentration of the alcohol is changed by diluting a solution comprising the drug, the lipid, and the alcohol; and
(A-2) measuring a chronological change in a particle size of a liposome loaded with the drug under a condition where the concentration of the alcohol is constant;

wherein the control section determines at least one condition selected from the group consisting of the concentration of the alcohol in the primary diluting solution, the concentration of the lipid, the predetermined time, and the temperature upon the mixing based on information obtained by steps (A-1) and (A-2).
(Item Y11)

The system of item Y10 or Y11, wherein the alcohol concentration in the primary diluting solution is adjusted to 18 wt % or greater.
(Item Y12)

A system for manufacturing a liposome with a desired particle size, the system comprising:
(1) a liposome manufacturing apparatus; and
(2) a dialyzer,
wherein the liposome manufacturing apparatus comprises:

(1-A) a first mixing region for preparing a primary diluting solution by mixing a first solution comprising a lipid and alcohol with a second solution comprising water;
(1-B) a second mixing region for preparing a secondary diluting solution by mixing the primary diluting solution with a third solution comprising water; and
(1-C) a liquid supplying tube for supplying the primary diluting solution from the first mixing region to the second mixing region in a predetermined time;

wherein a particle size of a liposome is controlled by adjusting at least one condition selected from the group consisting of a concentration of the alcohol in the primary diluting solution, a concentration of the lipid, the predetermined time, and a temperature upon the mixing, and the dialyzer comprises:

(2-A) a hollow fiber dialysis column having a hollow fiber membrane and a first flow channel where a solution subjected to dialysis flows inside the hollow fiber membrane;
(2-B) a liquid supplying section for supplying the solution subjected to dialysis to an inlet of the first flow channel; and
(2-C) a second flow channel having a portion in contact with the hollow fiber membrane.
(Item Y13)

The system of item Y12, wherein the second flow channel is a flow channel wherein an external solution flows outside the hollow fiber membrane.
(Item Y14)

The system of Y12, wherein the second flow channel is a flow channel where a filtrate of the hollow fiber membrane flows.
(Item Y15)

The system of item Y14, comprising a third flow channel for adding an external solution to the solution subjected to dialysis.
(Item Y16)

The system of any one of items Y12 to Y15, comprising a solution storage container, wherein the solution storage container is connected to the liposome manufacturing apparatus and the dialyzer, and the solution storage container stores a liposome containing solution flowing in from the liposome manufacturing apparatus.
(Item Y17)

The system of any one of items Y12 to Y16, wherein the dialyzer comprises
(2-D) a flow rate/pressure varying section, which can change a flow rate and/or pressure of the solution subjected to dialysis when flowing out from an outlet of the first flow channel,
wherein the flow rate varying section comprises an apparatus, provided downstream of the outlet of the first flow channel, for supplying the solution subjected to dialysis that has flowed out from the outlet of the first flow channel downstream at a lower flow rate and/or lower pressure than a flow rate at the liquid supplying section at the inlet of the first flow channel.

(Item Y18)

The system of item Y17, wherein the apparatus of the flow rate varying section comprises:

(1) a pump for supplying the solution subjected to dialysis that has flowed out from the outlet of the first flow channel downstream at a predetermined flow rate; or (2) a valve for narrowing a flow channel of the solution subjected to dialysis that has flowed out from the outlet of the first flow channel.

(Item Y19)

The system of any one of items Y12 to Y18, wherein an alcohol concentration in the primary diluting solution is adjusted to 18 wt % or greater.

(Item Y20)

The system of any one of items Y12 to Y19 configured so that the solution subjected to dialysis that has flowed out from the outlet of the first flow channel flows in again.

The present invention is intended so that one or more of the features described above can be provided not only as the explicitly disclosed combinations, but also as other combinations thereof. Additional embodiments and advantages of the invention are recognized by those skilled in the art by reading and understanding the following detailed description as needed.

Advantageous Effects of Invention

Lipid particles comprised of various lipid compositions and loaded drug can be provided with a desired particle size and particle size distribution by using the present invention. The present invention is thus useful for studying pharmacokinetics, stabilization of an active ingredient, formulation design, and the like.

BRIEF DESCRIPTION OF DRAWINGS

FIG. 1 is a schematic diagram of a one-step inline closed lipid particle manufacturing system.

FIG. 2 is a schematic diagram of a lipid particle manufacturing system. 1a and 1b are first and second mixing regions, respectively. 2 is a liquid supplying tube. 3a, 3b, and 3c are each pumps.

FIG. 4 is a diagram showing an example of a hollow fiber membrane column in a dialyzer.

FIG. 5 is a block diagram showing the configurations of a concentration control unit for a solution subjected to dialysis, separated into each function.

FIG. 6 is a diagram for describing the control when removing organic microparticles in a solution subjected to dialysis by hardly changing the concentration of the solution subjected to dialysis (lipid particle solution).

FIG. 7 is a diagram for describing the control when a solution subjected to dialysis (lipid particle solution) is concentrated while removing organic microparticles.

FIG. 8 is a diagram showing a modified example of a flow rate varying section of the dialyzer according to an embodiment of the invention.

FIG. 9A is a diagram showing an exemplary embodiment combining the lipid particle manufacturing apparatus and dialyzer of the invention.

FIG. 9B is a diagram showing an exemplary embodiment combining the lipid particle manufacturing apparatus and dialyzer of the invention.

FIG. 9C is a diagram showing an exemplary embodiment combining the lipid particle manufacturing apparatus and dialyzer of the invention.

FIG. 10A is a diagram showing a change in the particle size distribution when using HSPC:Cholesterol:MPEG 2000 DSPE (56:39:5) as the lipid composition (molar ratio). The left side shows the particle size distribution of liposomes immediately after preparation and 1 hour after preparation at ethanol concentrations of 12%, 18%, 27%, 36%, 39%, 42%, and 46%. The right side shows the particle size distribution of liposomes immediately after preparation and 1 day after preparation at ethanol concentrations of 15%, 18%, 21%, 24%, 27%, and 30%.

FIG. 10C is a diagram showing the particle size distribution of liposomes immediately after preparation and 1 hour after preparation when using DOPC:DOPG:DPPC:DPPG:Cholesterol (1:1:1:1:2.7) as the lipid composition (molar ratio).

FIG. 11B is a diagram showing the particle size distribution immediately after, 1 hour after, and 2 days after the preparation of liposomes prepared at each of the secondary dilution concentrations when using the composition of HSPC, Cholesterol, and MPEG 2000 DSPE described in Examples 2-2.

FIG. 12C is a diagram showing the particle size distribution at 25% dilution concentration of liposomes prepared at each lipid concentration when using DOPC:DOPG:DPPC: DPPG:Cholesterol (1:1:1:1:2.7) as the lipid composition (molar ratio).

FIG. 14 FIG. 14 is a diagram showing the particle distribution of liposomes when the flow rate and flow channel length are changed.

FIG. 15B is a diagram showing the particle size distribution of liposomes prepared at each flow rate (time of retention) when using DOPC:DOPG:DPPC:DPPG:Cholesterol (1:1:1:1:2.7) as the lipid composition (molar ratio).

FIG. 16A is a diagram showing the particle size distribution immediately after, 1 hour after, and 2 days after the preparation of liposomes prepared at each time of retention when using the composition of DOPC, DOPG, DPPC, DPPG, and Cholesterol described in Examples 4-4.

FIG. 16B is a diagram showing the particle size distribution immediately after, 1 hour after, and 2 days after the preparation of liposomes prepared at each time of retention when using the composition of HSPC, Cholesterol, and DSPG described in Examples 4-5.

FIG. 17 is a diagram showing the particle size distribution of liposomes when the temperature was changed.

FIG. 19 is a diagram showing the particle size distribution of liposomes in a first diluting solution at each concentration.

FIG. 20 is a diagram showing a comparison of micelles and liposomes prepared by the method of the invention. FIG. 20A shows the percentage (%) of micelles among all lipid particles in each lipid particle preparation, measured by electron microscopy. FIG. 20B shows observed images of representative lipid particles in each lipid particle preparation stained with phosphotungstic acid (×200,000 magnification). FIG. 20C shows the particle size distribution in each lipid particle preparation.

DESCRIPTION OF EMBODIMENTS

Figure 3A:
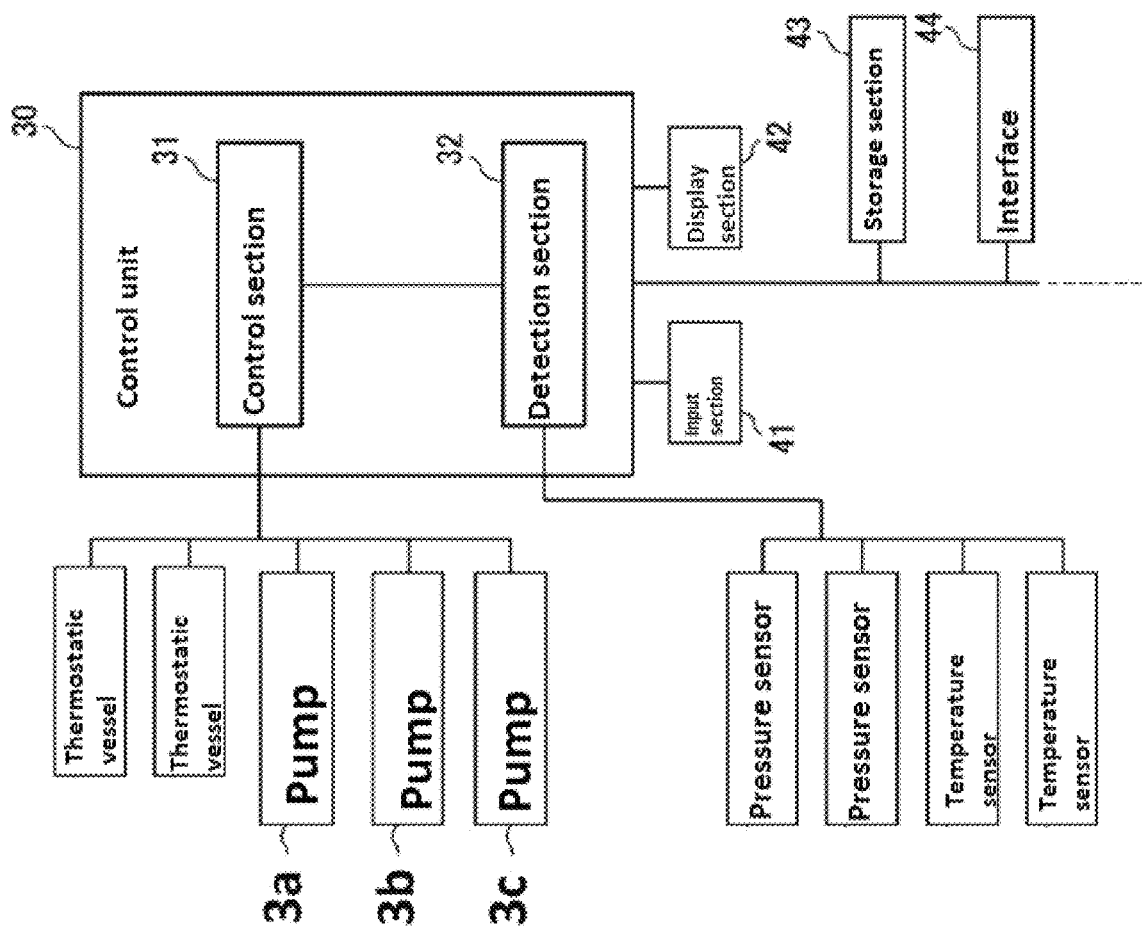
FIG. 3A is a block diagram showing the configurations of a lipid particle size control unit in one embodiment of the invention, separated into each function.

The present invention is described hereinafter while showing the best mode of the invention. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

The definitions of the terms and/or basic technical matters especially used herein are described hereinafter when appropriate.

Definition

As used herein, "lipid particle" refers to particulate substances formed in a fluid, comprising lipid molecules having a hydrophobic group and a hydrophilic group. Local hydrophilic and hydrophobic environments are produced between the inside and outside of lipid particle or inside a lipid particle, based on the polarity of a hydrophobic group and a hydrophilic group of a lipid molecule. A lipid particle can comprise a liposome and a micelle. Lipid particles can be typically lipid nanoparticles with a mean particle size of less than 1 μm. Lipid particles or the lipid bilayer thereof are readily accepted into a biological environment because they are similar to a cellular membrane constituting an organism. Since lipid particles provide an independent and local environment, a drug can be loaded. For this reason, lipid particles are sometimes used in a drug delivery system (DDS). For example, a drug can be loaded into a lipid particle and transported to a predetermined site in the organism. While the lipid particles of the invention are especially suitable for pharmaceutical use, the use is not limited. The lipid particles can be used in applications such as food products, cosmetics, agriculture, imaging, or the like.

As used herein, "liposome" refers to a lipid vesicle comprised of a lipid bilayer comprising a lipid molecule, or specifically to a vesicle with a space separated from the external environment by a lipid bilayer generated based on the polarity of a hydrophobic group and a hydrophilic group of a lipid molecule. A liposome can be a unilamellar liposome having a single lipid bilayer (SUV: Small Unilamellar Vesicle) or a multilamellar liposome with a plurality of layers (MLV: Multilamellar Vesicle). A bilayer is comprised of two unilamellar lipid membranes having a hydrophobic "tail" region and a hydrophilic "head" region. A membrane bilayer is structured so that the hydrophobic (nonpolar) "tail" of a lipid monolayer faces the center of the bilayer, while the hydrophilic "head" faces the aqueous phase.

As used herein, "micelle" refers to a particulate substance comprising a lipid molecule having a hydrophobic group and a hydrophilic group, resulting in each of a hydrophilic environment and a hydrophobic environment in the inside and outside thereof, based on the polarity of the hydrophobic group and hydrophilic group of the lipid molecule. For example, a lipid molecule can be oriented to position the hydrophobic group of the lipid molecule inside and the hydrophilic group of the lipid molecule outside in a micelle formed in an aqueous solvent.

When a drug is "loaded" in a lipid particle herein, the drug is retained inside and/or on the surface of the lipid particle. When a drug is "loaded" in a lipid particle, at least a part of the drug is retained inside or on the surface of the lipid particle. A drug can be at any of the aqueous phase in the liposome, lipid phase of a liposome membrane, lipid phase in a micelle, interface between phases of a lipid particle, interface between a lipid particle and the external environment, and combination thereof, or immobilized on the lipid particle surface layer by electrostatic interaction or the like, or a part of all parts of the drug can be contained within one of the phases of the lipid particles.

As used herein, "lipid particle formulation" refers to the lipid particle itself, or a formulation using a lipid particle as a carrier that is loaded with a drug. A lipid particle formulation can be lipid particles dispersed or suspended in a lipid particle external solution or lyophilized.

As used herein, "lipid" is used in the meaning that is commonly used in the art, referring to a substance having a hydrophobic portion such as a long-chain fatty acid or a hydrocarbon chain. Examples of lipids include phosphatidylcholines (soy lecithin, hydrogenated soy lecithin, egg yolk lecithin, and the like), phosphatidylserines, phosphatidylethanolamines, phosphatidylinositols, phosphasphingomyelins, phosphatidic acids, long-chain alkyl phosphates, gangliosides, glycolipids, phosphatidylglycerols, cholesterols, fatty acid esters of glycerol, tocopherol, steroid, fatty acid, and the like.

As used herein, "amphiphilic lipid" refers to a lipid with both hydrophobic and hydrophilic portions. A hydrophilic portion can be, for example, a portion comprising a group having polarity or charge such as a phosphoric acid group, carboxylic acid group, sulfuric acid group, amino group, sulfhydryl group, nitro group, or hydroxy group. A hydrophobic portion can be a portion comprising a nonpolar group such as a long-chain saturated or unsaturated aliphatic hydrocarbon group, aromatic group, or alicyclic or heterocyclic group. Examples of amphiphilic lipids include, but are not limited to, phospholipids, amino lipids, sphingolipids, glycosphingolipids, diacylglycerols, β-acyloxy acids, and the like. A phospholipid is generally an amphiphilic substance with a hydrophobic group comprised of a long-chain alkyl group and a hydrophilic group comprised of a phosphoric acid group within a molecule. Examples of phospholipids include, but are not limited to, phosphatidylcholine (=lecithin), phosphatidylglycerol, phosphatidylethanolamine, phosphatidylserine, phosphatidylinositol, phosphatidic acid, sphingophospholipid, diphosphatidyl-based phospholipid, palmitoyl oleoyl phosphatidylcholine, lysophosphatidylcholine, lysophosphatidylethanolamine, dimyristoylphosphatidylcholine (DMPC), dimyristoylphosphatidylglycerol (DMPG), dipalmitoylphosphatidylcholine (DPPC), dipalmitoylphosphatidylglycerol (DPPG), dioleoylphosphatidylcholine (DOPC), distearoylphosphatidylcholine (DSPC), distearoylphosphatidylglycerol (DSPG), dioleoylphosphatidylethanolamine (DOPE), palmitoylstearoylphosphatidylcholine (PSPC), palmitoylstearoylphosphatidylglycerol (PSPG), dilinoleoylphosphatidylcholine, and the like.

As used herein, "acyl (group)" is used in the meaning that is commonly used in the art, referring to a group made by removing a hydroxyl group from an organic acid (carboxylic acid; fatty acid). An acyl (group) also broadly encompasses a formyl group HCO—, acetyl group $CH_3CO$—, malonyl group —$COCH_2CO$—, benzoyl group $C_6H_5CO$—, cinnamoyl group $C_6H_5CH$=CHCO—, ketone derivatives, and the like. In a preferred embodiment, an acyl group included in a phospholipid is also known as a fatty acid group because such a group forms a fatty acid. A fatty acid can be expressed herein by the number of carbons and the number of double bonds. For example, arachidonic acid can be expressed as (20:4). When the position of a double bond is further specified, cis or trans, or E or Z can be indicated by specifying all positions or by systems such as ω3 system or ω6 system.

If a lipid comprises a fatty acid or an acyl group based thereon, the fatty acid or the acyl group can have any chain length and any double bond. For example, the number of carbons is one or more, typically 1 to 30, and normally in the range of 4 to 30. Examples thereof include, but are not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and the like. As the number of double bonds, any allowable number can be used in accordance with the number of carbons, such as 0, 1, 2, 3, 4, 5, 6, 7, or the like. The position of a double bond is typically the ω-3 system, ω-6 system, ω-9 system, or the like. In addition, ω-5 system, ω-7 system, and the like are also confirmed. Any available system thereamong can be used. A fatty acid can comprise a triple bond. As the number, any allowable number can be used in accordance with the number of carbons such as 0, 1, 2, 3, 4, 5, 6, o7, or the like.

As used herein, "anionic lipid" refers to a lipid with a negative charge at a physiological pH. Examples of such a lipid include, but are not limited to, phosphatidylglycerol, cardiolipin, diacylphosphatidylserine, diacylphosphatidic acid, N-dodecanoylphosphatidylethanolamine, N-succinylphosphatidylethanolamine, N-glutarylphosphatidylethanolamine, lysylphosphatidylglycerol, and other anionic modified groups bound to a neutral lipid.

As used herein, "cationic lipid" refers to a lipid with a positive charge at a physiological pH. Examples of such a lipid include, but are not limited to, N,N-dioleoyl-N,N-dimethylammonium chloride ("DODAC"), N-(2,3-oleoyloxy)propyl-N,N,N-trimethylammonium chloride ("DOTMA"), N,N-distearyl-N,N-dimethylammonium bromide ("DDAB"), N-(2,3-oleoyloxy)propyl-N,N,N-trimethylammonium chloride ("DOTAP"), 3-(N—(N',N'-dimethylaminoethane)-carbamoyl) cholesterol ("DC-Chol"), and N(1,2-dimyristyloxyprop-3-yl)N,N-dimethylhydroxyethylammonium bromide ("DMRIE"), and the like.

Examples of cholesterols include cholesterol, phytosterol (sitosterol, stigmasterol, fucosterol, spinasterol, and brassicasterol), lanosterol, ergosterol, fatty acid ester thereof, and the like.

As used herein, "agent" is used broadly and may be any substance or other elements (e.g., light, radiation, heat, electricity, and other forms of energy) as long as the intended objective can be achieved. Examples of such a substance include, but are not limited to, protein (including antibodies and the like), polypeptide, oligopeptide, peptide, polynucleotide, oligonucleotide, nucleotide, nucleic acid (including, for example, DNAs such as cDNA and genomic DNA and RNAs such as mRNA), polysaccharide, oligosaccharide, lipid, organic small molecule (e.g., hormone, ligand, information transmitting substance, organic small molecule, molecule synthesized by combinatorial chemistry, small molecule that can be used as medicine, and composite molecule thereof.

In general, the composition, medicament, agent (therapeutic agent, prophylactic agent, and the like) and the like of the present invention generally comprise a therapeutically effective amount of medicament or active ingredient and a pharmaceutically acceptable carrier or excipient. As used herein, "pharmaceutically acceptable" means government regulatory agency-approved or pharmacopoeia or other commonly recognized pharmacopoeia-listed for use in animals and more specifically in humans.

As used herein, "drug" is used in the meaning that is commonly used in the art, referring to a substance effecting some type of physiological action when administered to an organism. Examples thereof include proteins (including enzymes, antibodies, and the like), peptides, nucleic acids (DNA, mRNA, siRNA, and miRNA), vectors, viral particles, plasmids, toxins, saccharides (oligosaccharides and polysaccharides), polymer compounds, anticancer agents, antibiotics, enzymatic agents, antioxidants, lipid uptake inhibitors, hormonal agents, anti-inflammatory agents, steroidal agents, vasodilators, angiotensin converting enzyme inhibitors, angiotensin receptor antagonists, smooth muscle cell proliferation/migration inhibitors, platelet aggregation inhibitors, anticoagulants, chemical mediator release inhibitors, vascular endothelial cell growth promoters or inhibitors, aldose reductase inhibitors, mesangial cell proliferation inhibitors, lipoxygenase inhibitors, immunosuppressants, immunostimulants, antirheumatic drugs, anti-inflammatory enzyme formulations, gout treating drugs, antihistamines, chemical transmitter release inhibitors, antiviral agents, Maillard reaction inhibitors, amyloidosis inhibitors, nitrogen monoxide synthesis inhibitors, AGF (Advanced glycation end product) inhibitors, hemoglobins, radical scavengers, glycosaminoglycans and derivatives thereof, corticosteroids such as prednisolone, methylprednisolone, and dexamethasone and derivatives thereof, non-steroidal anti-inflammatory agents such as aspirin, indomethacin, ibuprofen, mefenamic acid, and phenylbutazone, mesangial cell growth inhibitors such as heparin and low molecular weight heparin, immunosuppressants such as cyclosporine; ACE (angiotensin converting enzyme) inhibitors such as captopril, AGE (advanced glycation end product) inhibitors such as methylguanidine, TGF-β antagonists such as biglycan and decorin, PKC (protein kinase C) inhibitors, prostaglandin formulations such as PGE1 and PGI2, peripheral vasodilators such as papaverine based drugs, nicotinic acid based drugs, tocopherol based drugs, and Ca antagonists, antithrombotic drugs such as phosphodiesterase inhibitors, ticlopidine, and aspirin, anticoagulants such as warfarin, heparin, and antithrombin agent, thrombolytic drugs such as urokinase, chemical mediator release inhibitors, antibiotics, antioxidants, enzymatic agents, lipid uptake inhibitors, hormonal agents, vitamin C, vitamin E, SOD and other radical scavengers, antisense oligonucleotides having an inhibitory effect on mesangial cell growth, and the like.

As used herein, "particle size" is a scale used to represent the size of a particle, and is used as a value corresponding to the diameter if the particle is assumed to be a complete sphere for convenience, as in the meaning that is commonly used in the art. The particle size of a lipid particle can be measured with any method known in the art. For example, the particle size can be measured by freeze fracture using a transmission electron microscope (TEM) or a method utilizing dynamic light scattering such as Malvern Zetasizer. As used herein, "mean particle size" can be used to refer to either the number average particle size or the Z-mean particle size, but refers to the Z-mean particle size calculated from the measured particle size, unless specifically noted otherwise. As used herein, "particle size distribution" is used in the meaning that is commonly used in the art, referring to the spread of particle sizes. Polydispersity index (PDI) is used as the scale representing the particle size distribution.

As used herein, "alcohol" refers to any organic compound wherein a hydroxy functional group (—OH) is bound to a saturated carbon atom. Alcohol can be monovalent or have higher valency. Alcohol can have a carbon chain comprising 1 to 20 carbon atoms. The carbon chain can comprise a ring and/or a double bond. The carbon chain can be linear or branched. Examples of alcohol include methanol, ethanol, isopropyl alcohol, 1-propanol, butyl alcohol, and pentanol.

As used herein, "hollow fiber membrane" is used in the meaning that is commonly used in the art, referring to fine tubes with numerous pores on the tubular wall. This can be used to perform dialysis.

As used herein, "membrane filtration" refers to a mechanical separation method for separating a liquid flow using a dialysis membrane. Examples of membrane filtration include reverse osmosis (RO), nanofiltration (NF), ultrafiltration (UF), and microfiltration (MF).

As used herein, "flow rate" refers to the rate at which a solution flows within a tube. As used herein, flow rate is a quantity that can be expressed in terms of the dimension of (distance)/(time) or (volume)/(time).

As used herein, "time of retention" refers to the time required for a solution to move from a region to another region. For example, if region A is linked to region B via a liquid supplying tube C, the time of retention from region A to region B can be calculated by (length of liquid supplying tube)/(flow rate [cm/min]).

As used herein, "measure" is used in the meaning that is commonly used in the art, referring to measuring and finding the amount for a certain subject. As used herein, "detect" is used in the meaning that is commonly used in the art, referring to testing and finding out a substance, component, or the like. "Identify" refers to an act of finding a classification for a certain subject from among existing classifications associated therewith. When used in the field of chemistry, this refers to determining the identity as a chemical substance of a target substance (e.g., determining a chemical structure). "Quantify" refers to determining the existing amount of the target substance.

As used herein, the "amount" of an analyte in a bodily fluid sample generally refers to an absolute value reflecting the mass of the analyte that can be detected in a volume of sample. However, amount is also intended as a relative amount as compared to the amount of another analyte. For example, the amount of an analyte in a sample can be an amount that is greater than a control level or a normal level of an analyte that is generally present in a sample.

The term "about", when used herein in relation to a quantitative measurement excluding measurement of the mass of an ion, refers to the indicated value plus or minus 10%. Even if "about" is not explicitly indicated, a value can be interpreted in the same manner as if the term "about" is used. Mass spectrometers can slightly vary in the determination of mass of a given analyte. The term "about" in relation to the mass of ions or the mass/charge ratio of ions refers to +/−0.5 atom mass unit.

Preferred Embodiments

The preferred embodiments of the invention are described hereinafter. It is understood that the embodiments provided hereinafter are provided for better understanding of the invention, so that the scope of the present invention is not limited to the following descriptions. It is therefore apparent that those skilled in the art can refer to the descriptions herein to make appropriate modifications within the scope of the present invention. It is understood that the following embodiments of the invention can be used alone or in combination.

(Method of Producing Lipid Particles)

In one aspect, the present invention provides a method of manufacturing a lipid particle (e.g., liposome or micelle) with a desired particle size. This method comprises: A) preparing a primary diluting solution by mixing a first solution comprising a lipids and alcohol with a second solution comprising water in a first mixing region; B) supplying the primary diluting solution from the first mixing region to a second mixing region through a liquid supplying tube in a predetermined time; and C) preparing a secondary diluting solution by mixing the primary diluting solution with a third solution comprising water in the second mixing region; wherein a particle size of lipid particles is controlled by adjusting at least one condition selected from the group consisting of a concentration of the alcohol in the primary diluting solution, a concentration of the lipid, the predetermined time, and a temperature upon the mixing. In one embodiment, additional particle size controlling processing is not performed after step (C). In one embodiment, the method can further perform, after step (C), supplying the secondary diluting solution from the secondary mixing region to a third mixing region through a liquid supplying tube in a predetermined time, and preparing a tertiary diluting solution by mixing the secondary diluting solution with a fourth solution comprising water (can be defined in the same manner as one of first, second, and third solution) in the third mixing region. In one embodiment, the method can comprise dissolving a lipid (and/or drug) into alcohol in the preparation of a solution comprising a lipid and alcohol.

One of the important points in the present invention is that the particle size of a lipid particle (e.g., liposome or micelle) can be adjusted by adjusting at least one of a concentration of alcohol in a primary diluting solution, concentration of a lipid, predetermined time, and temperature upon mixing. Although not wishing to be bound by any theory, one of the important points in the present invention is particularly that the particle size of a lipid particle (e.g., liposome or micelle) can be finely adjusted by serially adjusting the alcohol concentration. It is also one of the important points in the present invention that a lipid particle (e.g., liposome or micelle) with a desired particle size can be manufactured by serially adjusting the alcohol concentration and then supplying a solution in a predetermined time, and in doing so, the particle size distribution that is narrow to the extent that it is acceptable at a drug development level can be achieved. Furthermore, the particle size of a lipid particle (e.g., liposome or micelle) can be adjusted more finely by adjusting the temperature upon mixing.

In one embodiment, the present invention provides a method of manufacturing a lipid particle (e.g., liposome or micelle) with a desired particle size, which are loaded with a drug, the method further comprising: measuring a particle size of lipid particles formed when a concentration of alcohol is changed by diluting a solution comprising a drug, lipid, and alcohol; and measuring a chronological change in a particle size of lipid particles comprising the drug under a condition where the concentration of alcohol is constant; wherein at least one condition required for adjusting the desired particle size selected from the group consisting of the concentration of the alcohol in the primary diluting solution, the concentration of the lipid, the predetermined time, and the temperature upon the mixing for obtaining the desired particle size is determined based on information obtained in this manner. The at least one condition selected from the group consisting of a concentration of the alcohol in the primary diluting solution, a concentration of the lipid, the predetermined time, and a temperature upon the mixing measured under such a condition can be used to manufacture a lipid particle (e.g., liposome or micelle) with a desired particle size hereinafter.

The lipid contained in the first solution can be a combination of any lipids. Each lipid component can be included at any ratio. In one embodiment, a lipid is selected so that a drug is loaded inside a lipid particle (e.g., liposome or micelle). In one embodiment, a lipid is selected so that a drug is loaded on a surface of lipid particles (e.g., liposome or micelle). In one embodiment, a lipid is selected so that a drug is loaded on a lipid bilayer of a liposome. In one embodiment a lipid contained in a first solution has a phase transition temperature that is higher than the temperature in the body (35 to 37° C.). By using such a lipid, a drug loaded in a lipid particle (e.g., liposome or micelle) can be less likely to leak to the outside from lipid particles during storage or in a biological environment such as blood.

In one embodiment, alcohol contained in a first solution comprises monovalent or divalent alcohol comprising 1 to 6 carbon atoms. Alternatively, alcohol contained in a first solution comprises monovalent or divalent alcohol. In another embodiment, alcohol contained in a first solution comprises monovalent alcohol. In a specific embodiment, alcohol contained in a first solution comprises monovalent alcohol comprising 1 to 3 carbon atoms. In a specific embodiment, alcohol contained in a first solution comprises methanol, ethanol, isopropyl alcohol, or a combination thereof.

In one embodiment, a second solution and/or third solution can comprise alcohol contained in a first solution at a lower concentration than in the first solution.

Solutions used in the method of manufacturing lipid particles of the invention, including the first solution, second solution, and third solution, can comprise a solvent other than water and alcohol. Examples of such a solvent include, but are not limited to, solvents miscible with water such as ethers, esters, ketones, acetals, tetrahyrofuran, 1,4-dioxane, acetone, acetonitrile, dimethylformamide, and dimethylsufoxide, and solvents nonmiscible with water such as hexane, benzene, toluene, chloroform, ethyl acetate, and methyl chloride.

In one embodiment, one of the first solution, second solution, and third solution comprises a drug of interest to be loaded in lipid particles. In one embodiment, one of the first solution and the second solution comprises a drug of interest to be loaded in lipid particles. In one embodiment, solution that is not the first solution, second solution, or third solution can comprise a drug of interest to be loaded in lipid particles. A drug of interest can be any drug. A drug of interest does not need to be a drug intended for therapy, such as an insecticide, herbicide, cosmetic agent, fragrance, food additive, flavor, imaging agent, dye, fluorescent marker, hair growth agent, humectant, pigment, whitening agent, pigment, X-ray contrast agent, ultrasonic diagnostic drug, radioisotope-labeled nuclear medicine diagnostic drug, or diagnostic agent for nuclear magnetic resonance diagnostics.

Any solution used in the method of manufacturing lipid particles of the invention, including the first solution, second solution, and third solution, can comprise an additive as needed, such as an osmoregulation agent, stabilizer, antioxidant, or pH regulator.

An osmoregulation agent is not particularly limited. Examples thereof include inorganic salts such as sodium chloride, potassium chloride, sodium hydrogen phosphate, sodium dihydrogen phosphate, and potassium dihydrogen phosphate, polyols such as glycerol, mannitol, and sorbitol, and saccharides such as glucose, fructose, lactose, and sucrose.

A stabilizer is not particularly limited. Examples thereof include saccharides such as glycerol, mannitol, sorbitol, lactose, and sucrose, and sterol such as cholesterol.

An antioxidant is not particularly limited. Examples thereof include ascorbic acid, uric acid, and tocopherol homologs (e.g., vitamin E). While tocopherol has 4 isomers α, β, γ, and δ, any of them can be used in the present invention.

A pH regulator can be any basic or acidic compound. Examples thereof include sodium hydroxide, citric acid, acetic acid, triethanolamine, sodium hydrogen phosphate, sodium dihydrogen phosphate, and the like.

Examples of other additives include pharmaceutically acceptable organic solvents, collagen, polyvinyl alcohol, polyvinylpyrrolidone, carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, gelatin, agar, diglycerin, propylene glycol, polyethylene glycol, petrolatum, paraffin, stearyl alcohol, stearic acid, human serum albumin (HSA), PBS, biodegradable polymer, serum-free medium, surfactant acceptable as a pharmaceutical additive, buffer with a physiological pH, and the like.

The inventors found that the particle size of lipid particles chronologically changes if the alcohol concentration (wt %) in a primary diluting solution is adjusted to a specific value (also referred to as a "fluidity changing point" herein) or greater, whereas the particle size of lipid particles hardly changes at an alcohol concentration less than the fluidity changing point. In one embodiment, the fluidity changing point can change depending on the composition of lipid particles, temperature, and pressure. In one embodiment, the fluidity changing point can change depending on the type of alcohol in the primary diluting solution. In one embodiment, the fluidity changing point can change depending on the composition of lipid particles, temperature, and pressure. In one embodiment, the fluidity changing point does not change depending on the composition of lipid particles and/or presence/absence of drug loaded in lipid particles if the type of alcohol in the primary diluting solution is the same. These conditions and conditions described elsewhere that are disclosed herein can be applied to both liposomes and micelles as long as they are lipid particles.

In one embodiment, the alcohol concentration in the primary diluting solution can be about 10 to about 50 wt %, such as about 10 wt %, about 15 wt %, about 18 wt %, about 20 wt %, about 25 wt %, about 30 wt %, about 35 wt %, about 40 wt %, about 45 wt %, or about 50 wt %.

In one embodiment, the alcohol concentration in the secondary diluting solution is less than or equal to, or less than the fluidity changing point. The particle size distribution of lipid particles controlled in the primary diluting solution is fixed so that the value does not change by adjusting the concentration to such a concentration. In one embodiment, the fluidity changing point when alcohol is ethanol can be about 18 wt %. In one embodiment, the alcohol concentration in the secondary diluting solution can be about 0 to about 30 wt %, such as about 0 wt %, about 5 wt % or less, about 10 wt %, or less, about 15 wt % or less, about 18 wt %, or less, about 20 wt % or less, about 25 wt % or less, or about 30 wt % or less. The secondary diluting solution can be further diluted by mixing with an additional solution.

To control the particle size of lipid particles, it is preferable to use a specific combination of a range of alcohol concentrations in the primary diluting solution and a range of alcohol concentrations in the secondary diluting solution. Examples of such a combination include alcohol concentration in the primary diluting solution of about 10 to about 50 wt % and alcohol concentration in the secondary diluting solution of about 0 to about 30 wt %, alcohol concentration in the primary diluting solution of about 15 to about 50 wt % and alcohol concentration in the secondary diluting solution of about 0 to about 25 wt %, alcohol concentration in the primary diluting solution of about 20 to about 50 wt %, and alcohol concentration in the secondary diluting solution of about 0 to about 20 wt %, and the like. The range can vary depending on the type of solvent contained in the first solution. For example, if the first solution contains ethanol, the combination can be ethanol concentration in the primary diluting solution of about 10 to about 50 wt %, and ethanol concentration in the secondary diluting solution of about 0 to about 25 wt %, preferably ethanol concentration in the primary diluting solution of about 15 to about 50 wt % and ethanol concentration in the secondary diluting solution of about 0 to about 20 wt %, and more preferably ethanol concentration in the primary diluting solution of about 20 to about 50 wt % and ethanol concentration in the secondary diluting solution of about 0 to about 18 wt %. In one embodiment, the alcohol concentration in the primary diluting solution is preferably in a range where the liposome membrane does not sufficiently stabilize, and the alcohol concentration in the secondary diluting solution is preferably in a range where the liposome membrane stabilizes.

In one embodiment, a solution is mixed by generating a turbulence in a mixing region. In one embodiment, a solution is mixed by a mixing element (e.g., mixer) in a mixing region.

In one embodiment, the particle size of a liposome can be controlled by adjusting the predetermined time (time of retention) for the primary diluting solution to reach the second mixing region from the first mixing region (in some cases, predetermined time for the secondary diluting solution to reach the third mixing region from the second mixing region). In one embodiment, the predetermined time (time of retention) can be about 0.1 to about 60 minutes, such as about 0.1 minutes, about 0.2 minutes, about 0.5 minutes, about 1 minute, about 2 minutes, about 5 minutes, about 10 minutes, about 15 minutes, about 20 minutes, about 25 minutes, about 30 minutes, about 45 minutes, about 60 minutes, or greater. The primary diluting solution can be mixed with an addition solution during the travel from the first mixing region to the second mixing region. Lipid particles or a membrane thereof is destabilized in the primary diluting solution, and the fluidity of lipid increases by heating the lipid to the phase transition temperature or higher. Thus, the frequency of lipid particles fusing upon contact with one another due to Brownian motion increases. For this reason, it is understood that fusion between lipid particles generated with passage of time proceeds uniformly so that the particle size increases while maintaining a certain granularity distribution. The same applies to the control of the predetermined time for the secondary diluting solution to reach the third mixing region to the second mixing region.

In one embodiment, the predetermined time the primary diluting solution is retained in a liquid supplying tube until reaching the second mixing region from the first mixing region (in some cases, time the secondary diluting solution is retained in a liquid supplying tube until reaching the third mixing region from the second mixing region) is controlled with at least one of length of a flow channel length and flow rate between mixing regions. In one embodiment, the predetermined time the primary diluting solution is retained in a liquid supplying tube until reaching the second mixing region from the first mixing region is controlled with the flow rate between the first mixing region and the second mixing region. In one embodiment, the predetermined time the primary diluting solution is retained in a liquid supplying tube until reaching the second mixing region from the first mixing region is controlled with the length of a flow channel between the first mixing region and the second mixing region. In one embodiment, the length of a flow channel from the first mixing region to the second mixing region can be in the range of, for example, 0.1 to 500 m, 1 to 100 m, or 5 to 50 m, such as 0.1 m, 0.5 m, 1 m, 5 m, 10 m, 20 m, 30 m, 40 m, 50 m, 70 m, 100 m, 150 m, 200 m, or 500 m. In one embodiment, the flow rate between the first mixing region and the second mixing region can be in the range of, for example, 0.1 to 500 m/min, 1 to 100 m/min, or 5 to 50 m/min, such as 0.1 m/min, 0.2 m/min, 0.5 m/min, 1 m/min, 5 m/min, 10 m/min, 20 m/min, 30 m/min, 40 m/min, 50 m/min, 70 m/min, 100 m/min, 150 m/min, 200 m/min, or 500 m/min, or in the range of 0.1 to 500 mL/min, 1 to 100 mL/min, or 5 to 50 mL/min, such as 0.1 mL/min, 0.2 mL/min, 0.5 mL/min, 1 mL/min, 5 mL/min, 10 mL/min, 20 mL/min, 30 mL/min, 40 mL/min, 50 mL/min, 70 mL/min, 100 mL/min, 150 mL/min, 200 mL/min, or 500 mL/min. If the predetermined time (time of retention) the primary diluting solution is retained in a liquid supplying tube until reaching the second mixing region from the first mixing region is held constant, the effect of each of the length of a flow channel and flow rate on the particle size of lipid particles is low. For this reason, when the time of retention used is determined, a suitable combination of length of a flow channel and flow rate can be selected while taking into consideration the mixing ratio among solutions at each site of a lipid particle manufacturing apparatus, pressure, Reynolds number, and other elements. The same applies for control of the predetermined time for the secondary diluting solution to reach the third mixing region from the second mixing region.

In one embodiment, the diluting solution flows in a liquid supplying tube between mixing regions as a laminar flow. In one embodiment, the particle size of lipid particles can be controlled by adjusting the Reynolds number (Nre) in a diluting solution flowing in a liquid supplying tube between mixing regions. In one embodiment, the Reynolds number (Nre) in a primary diluting solution flowing in a liquid supplying tube between mixing regions can be less than 2000, less than 1000, less than 500, less than 300, less than 200, less than 100, or less than 50.

In one embodiment, the particle size of lipid particles can be controlled by controlling the temperature in each step of the method of manufacturing lipid particles of the invention. In one embodiment, a temperature at which a lipid maintains a dissolved state can be used. In one embodiment, the temperature is adjusted to maintain the temperature within the first mixing region and/or the liquid supplying tube in the range of 30° C. or greater and 95° C. or less, more preferably 50° C. or greater and 90° C. or less, and still more preferably 70° C. or greater and 85° C. or less. In one embodiment, the temperature is adjusted to maintain the temperature within the first mixing region at 30° C., 40° C., 50° C., 60° C., 70° C., 75° C., 80° C., 85° C., 90° C., 95° C., 100° C., or the like. In one embodiment, the temperature within the first mixing region and/or the liquid supplying tube is adjusted to be maintained in a range of temperatures where the lipid in the primary diluting solution and drug of interest to be loaded in lipid particles are completely dissolved or higher. When the temperature is adjusted in this manner, the temperature does not need to be strictly managed. For example, the temperature only needs to be maintained within the range of target temperature±5° C. or the like. In one embodiment, the temperature is adjusted so that the secondary diluting solution and/or solution in subsequent steps is maintained in the range of, for example, 0° C. or greater than 50° C. or less, more preferably 5° C. or greater and 30° C. or less, and still more preferably 15° C. or greater and 25° C. or less. The temperature of a solution can be adjusted using a heating medium. A heating medium can be any substance, and can be a liquid (e.g., water), gas, or solid (e.g., aluminum block).

In one embodiment, the particle size of lipid particles can be controlled by adjusting the concentration of lipid contained in the primary diluting solution. The particle size of lipid particles can increase with an increase in lipid concentration. In one embodiment, the concentration of lipid contained in the primary diluting solution can be in a range of 0.5 to 1000 mg/mL, 5 to 500 mg/mL, or 10 to 200 mg/mL, such as 0.5 mg/mL, 1 mg/mL, 5 mg/mL, 10 mg/mL, 20 mg/mL, 30 mg/mL, 40 mg/mL, 50 mg/mL, 70 mg/mL, 80 mg/mL, 100 mg/mL, 150 mg/mL, 200 mg/mL, 300 mg/mL, 500 mg/mL, 700 mg/mL, 1000 mg/mL, or the like, but the suitable concentration can vary depending on the composition of the lipid used. The number of lipid particles generated per unit volume increases with a higher lipid concentration, and the opportunity of contact among lipid particles increases due to Brownian motion or the like. Thus, fusion between lipid particles can be accelerated to increase the particle size.

In one embodiment, the particle size of lipid particles can be controlled by controlling pressure in each step of the method of manufacturing lipid particles of the invention. In one embodiment, pressure is controlled by back pressure. In one embodiment, the pressure within the first mixing region (or in some cases the second mixing region) and/or within the liquid supplying tube can be in the range of 0.01 to 100 MPa, 0.1 to 20 MPa, or 1 to 10 MPa, such as 0.01 MPa, 0.05 MPa, 0.1 MPa, 0.5 MPa, 1 MPa, 5 MPa, 10 MPa, 50 MPa, 100 MPa, or the like. In one embodiment, the pressure in tubing between mixing regions can be 0.5 MPa or greater, 0.8 MPa or greater, 1 MPa or greater, 1.5 MPa or greater, 2 MPa or greater, 3 MPa or greater, 4 MPa or greater, 5 MPa or greater, 8 MPa or greater, or 10 MPa or greater. The particle size distribution of lipid particles (PDI) can be maintained in a narrow range.

In one embodiment, the method of manufacturing lipid particles of the invention comprises adjusting the composition of a solution after producing lipid particles. In one embodiment, the method of manufacturing lipid particles of the invention comprises adjusting the lipid particle concentration after producing lipid particles. The step of adjusting the composition of a solution and the step of adjusting the liposome concentration can be performed simultaneously or separately. For example, the step of adjusting the composition of a solution and the step of adjusting the lipid particle concentration can be performed simultaneously by using a hollow fiber membrane column disclosed in International Publication No. WO 2016/024510. Examples of means for adjusting the lipid particle concentration in a solution comprising the produced lipid particles and adjusting the composition of a solution include, but are not limited to, ultrafiltration, dialysis, and the like.

In one embodiment, the method of manufacturing lipid particles of the invention is performed sequentially. In one embodiment, the method of manufacturing lipid particles of the invention is performed in an aseptic environment. In one embodiment, the method of manufacturing lipid particles of the invention is performed in a closed system. One advantage of the present invention is that lipid particles with a desired particle size can be manufactured even in a closed system. Another advantage is that the particle size distribution can also be contained within a desired range.

In one embodiment, the mean particle size of lipid particles manufactured by the method of the invention can be 10 to 1000 nm such as 10 nm to 500 nm, specifically 20 nm to 300 nm, and more specifically 30 nm to 200 nm. In one embodiment, the mean particle size of liposomes manufactured by the method of the invention can be at least 10 nm, 20 nm, 30 nm, 40 nm, 50 nm, 60 nm, 70 nm, 80 nm, 90 nm, 100 nm, 150 nm, 200 nm, or 250 nm and at most 1000 nm, 900 nm, 800 nm, 700 nm, 600 nm, 500 nm, 400 nm, 300 nm, 250 nm, or 200 nm, such as 20 nm to 1000 nm, 30 nm to 700 nm, 40 nm to 1000 nm, 40 nm to 700 nm, 40 nm to 500 nm, 40 nm to 400 nm, 20 nm to 300 nm, 30 nm to 300 nm, 50 nm to 250 nm, 60 nm to 200 nm, or 100 nm to 200 nm, and typically 40 nm to 300 nm. In one embodiment, the mean particle size of micelles manufactured by the method of the invention can be at least 5 nm, 7 nm, 10 nm, 15 nm, 20 nm, 25 nm, 30 nm, 40 nm, 50 nm, 60 nm, 70 nm, 80 nm, 90 nm, or 100 nm and at most 500 nm, 400 nm, 300 nm, 200 nm, 150 nm, 120 nm, 100 nm, 90 nm, 80 nm, 70 nm, 60 nm, or 50 nm, such as 5 nm to 500 nm, 7 nm to 300 nm, 10 nm to 150 nm, 15 nm to 100 nm, 15 nm to 300 nm, 15 nm to 150 nm, 5 nm to 90 nm, 10 nm to 90 nm, 20 nm to 80 nm, or 30 nm to 70 nm, and typically 15 nm to 90 nm. If the particle size of lipid particles is about 10 to 1000 nm, the size allows passage through many blood vessels in the body, so that an effect can be exerted such as the particles can be systemically administered from blood vessels for migration into various tissues of the body.

In one embodiment, the error between the mean particle size of lipid particles manufactured by the method of the invention and the desired particle size can be ±50 nm or less, ±40 nm or less, ±30 nm or less, ±20 nm or less, ±10 nm or less, ±5 nm or less, ±4 nm or less, ±3 nm or less, ±2 nm or less, ±1 nm or less, ±0.7 nm or less, ±0.5 nm or less, ±0.2 nm or less, or ±0.1 nm or less. The mean particle size of lipid particles can be controlled with high precision with the method of the invention.

In one embodiment, the particle size distribution of lipid particles manufactured by the method of the invention can be less than 0.5 in terms of polydispersity index, such as less than 0.2, specifically less than 0.1, more specifically less than 0.05, or less than 0.01.

In one embodiment, the surface of lipid particles can be modified with a modifier. Examples of modifiers include, but are not limited to, polyethylene glycol (PEG), ficoll, polyvinyl alcohol, styrene-maleic anhydride alternating copolymer, divinyl ether-maleic anhydride alternating copolymer, polyvinylpyrrolidone, polyvinyl methyl ether, polyvinyl methyl oxazoline, polyethyl oxazoline, polyhydroxypropyl oxazoline, polyhydroxypropyl methacrylamide, polymethacrylamide, polydimethylacrylamide, polyhydroxypropyl methacrylate, polyhydroxyethyl acrylate, hydroxymethyl cellulose, hydroxyethyl cellulose, polyaspartamide, synthetic polyamino acid, derivatives thereof, and the like. Lipid particles can be more likely to remain in blood for a long period of time by modification with PEG or a PEG derivative. Lipid particles can be more likely to reach target tissue by modifying the lipid particles with a targeting molecule (e.g., antibody) having affinity for specific tissue.

Liposomes produced by the method of the invention can be used in any application such as medicinal use, food products, cosmetics, agriculture, or imaging.

(System)

The present invention provides a system for manufacturing a lipid particle (e.g., liposome or micelle) with a desired particle size. The system can comprise any suitable means for carrying out the method of manufacturing lipid particles described above.

In one aspect, the present invention provides a system for manufacturing lipid particles with a desired particle size, the system comprising: (A) a first mixing region for preparing a primary diluting solution by mixing a first solution comprising a lipid and alcohol with a second solution comprising water; (B) a second mixing region for preparing a secondary diluting solution by mixing the primary diluting solution with a third solution comprising water; and (C) a liquid supplying tube for supplying the primary diluting solution from the first mixing region to the second mixing region in a predetermined time; wherein a particle size of lipid particles is controlled by adjusting a concentration of the alcohol in the primary diluting solution, a concentration of the lipid, and a temperature upon the mixing. In one embodiment, the system can comprise a third mixing region for preparing a tertiary diluting solution by mixing with a fourth solution comprising water (can be defined in the same manner as one of first, second, and third solution), and a liquid supplying tube for supplying the secondary diluting solution from the second mixing region to the third mixing region in a predetermined time. The particle size of lipid particles can be further controlled by adjusting the concentration of alcohol in the secondary diluting solution, concentration of lipid, and temperature upon mixing.

In one aspect, the system further comprises a control section for performing: measuring a particle size of lipid particles formed when a concentration of the alcohol is changed by diluting a solution comprising a drug, lipid, and alcohol; and measuring a chronological change in a particle size of lipid particles loaded with the drug under a condition where the concentration of alcohol is constant; wherein the control section determines the concentration of alcohol in the primary diluting solution and predetermined time based on information obtained by these steps.

Any tube for supplying liquid can be used in the system of the invention. The material of a tube can be determined while taking into consideration, for example, thermal insulation property (thermal conductivity), thermal resistance, chemical resistance, sealability, or the like. Examples of materials of a liquid supplying tube include, but are not limited to, thermoplastic plastic (e.g., polyvinyl chloride comprising a plasticizer), thermoplastic plastic elastomer (e.g., polyvinyl chloride free of a plasticizer, copolymer of styrene-ethylene-butylene and silicone oil, or polypropylene-based plastic comprising USP petrolatum), thermosetting rubber (e.g., siloxane polymer comprising non-crystalline silica), thermal aggregating fluororubber, and the like. For example, Saint-Gobain K.K's "PharMed BPT", "PharmaPure" or the like can be used as a liquid supplying tube. A liquid supplying tube can have any inner diameter such as about 0.8 mm.

A mixing region of the system of the invention can comprise a mixer. A suitable mixer can be selected while taking into consideration factors such as the composition of a solution, flow rate, and pressure. For example, when a low flow rate is used in relation to pressure, a mixer (Deneb Helix), micro swirl mixer, or the like that utilizes a microflow channel with high mixing efficiency even at low flow rates can be used.

Any container for accommodating each solution can be used in the system of the invention. The material of the container can be determined while taking into consideration thermal insulation property (thermal conductivity), thermal resistance, chemical resistance, sealability, or the like. In one embodiment, the container has an openable lid. In one embodiment, the container is a sealable container. In one embodiment, the container can be connected to the system of the invention while maintaining the sealed state.

A pump (flow rate varying section) can be installed in any part of the system of the invention. A pump can be, for example, a syringe pump, plunger pump, piston pump, or a roller pump. The flow rate, pressure, or the like can be adjusted with a pump.

The lipid particle manufacturing system of the invention can have a control unit 30 shown in FIG. 3A. The control unit 30 has a control section 31 and a detection section 32. The control section 31 and the detection section 32 are communicably connected to each other. The control described above can be executed only with hardware (e.g., dedicated circuit) or the control described above can be executed by having a CPU execute a program.

Figure 3B:
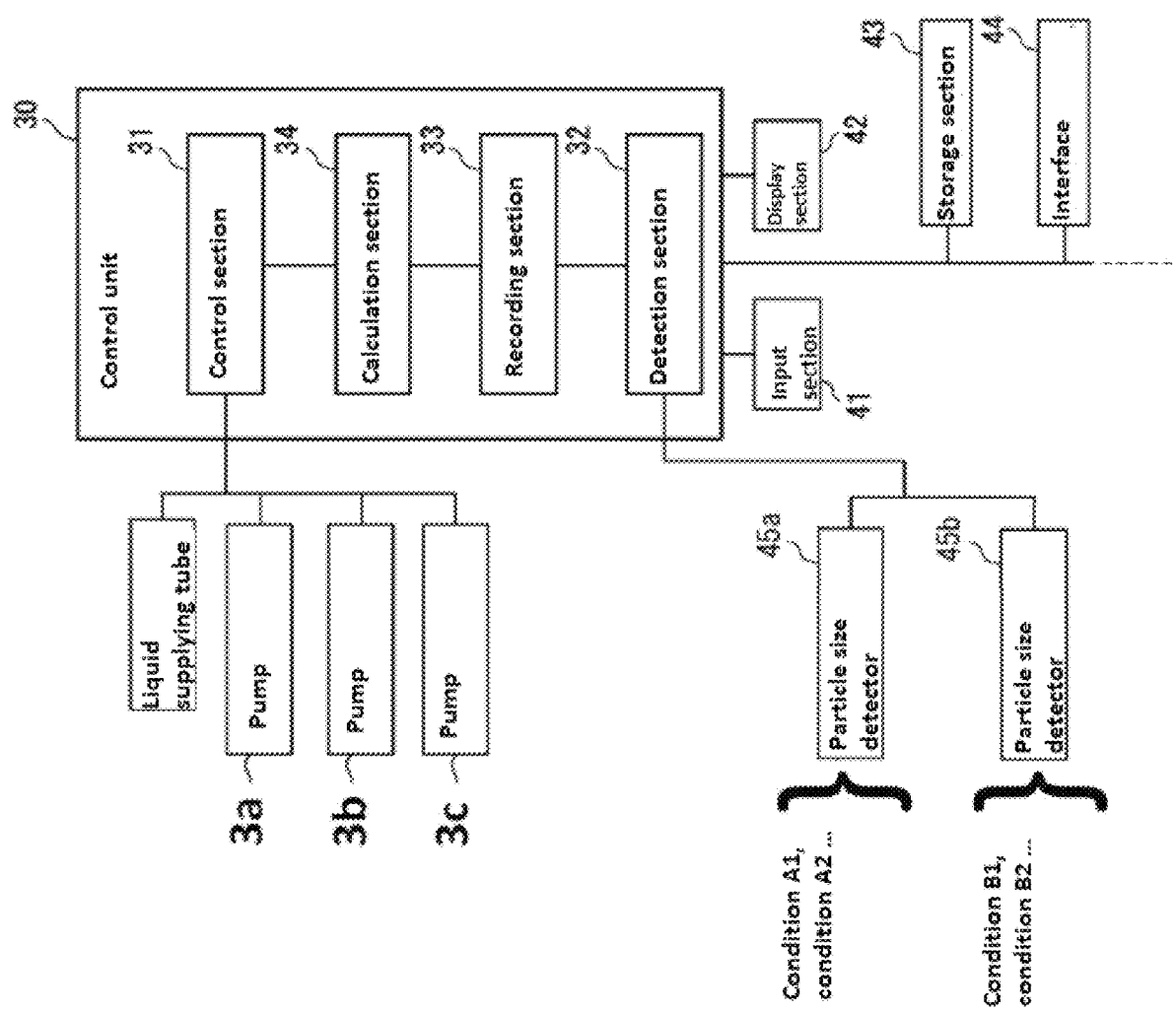
FIG. 3B is a block diagram showing the configurations of a lipid particle size control unit in one embodiment of the invention, separated into each function. Condition A1, Condition A2, and the like are conditions for diluting a solution comprising a drug, lipid, and alcohol to attain a predetermined value of alcohol concentration. Condition B1, Condition B2, and the like are conditions for allowing the time of retention to elapse by only a predetermined amount after dilution of alcohol concentration to a certain concentration.

In one embodiment, the lipid particle manufacturing system of the invention can have a control unit 30 shows in FIG. 3B. The control unit 30 has a control section 31, a detection section 32, a recording section 33, and a calculation section 34. The control section 31, detection section 32, recording section 33, and calculation section 34 are communicably connected to one another. The control described above can be executed only with hardware (e.g., dedicated circuit) or the control described above can be executed by having a CPU execute a program.

A particle size detector 45a detects the particle size of produced lipid particles under various conditions (condition A1, condition A2, and the like) for diluting a solution comprising a drug, lipid, and alcohol to attain a predetermined value of alcohol concentration. A particle size detector 45b detects the particle size of produced lipid particles under various conditions (condition B1, condition B2, and the like) for allowing the time of retention to elapse by only a predetermined amount after dilution of alcohol concentration to a certain concentration. The particle size detector 45a and the particle size detector 45b can be the same or different.

Data obtained with the particle size detector 45a and the particle size detector 45b is transmitted to the detection section 32 and accumulated in the recording section 33. The calculation section 34 calculates the alcohol concentration in the diluting solution and predetermined time (time of retention) until the diluting solution reaches from a mixing region to the next mixing region, which are suitable for the production of lipid particles with a desired particle size, based on information accumulated in the recording section 33 (together with an input from an input section 41 as needed).

The control section 31 is comprised of a CPU (Central Processing Unit), ROM (Read Only Memory), RAM (Random Access Memory), and drive circuits for various actuators included in the lipid particle manufacturing apparatus. Various programs such as BIOS (Basic Input/Output System), OS (Operating System), various drivers, and various applications are stored in ROM 52. The detection section 32 is comprised of detector circuits of various sensors (e.g., temperature sensor, pressure sensor, and particle size detector) included in a lipid particle manufacturing apparatus.

The control unit 30 are communicably connected to each of an input section 41, display section 42, storage section 43, and interface 44. The interface 44 can transmit and receive data between the control unit 30 and an external apparatus. The control unit 30 is connected to, for example, a generic computer (so-called personal computer), via the interface 44.

The input section 41 receives an input from a user. The input section 41 is comprised of, for example, a keyboard, mouse, or touch panel. The display section 42 is comprised of a display such as an LCD (Liquid Crystal Display) or ELD (Electro Luminescence Display). If the input section 41 and the display section 42 are comprised of a touch panel, the input section 41 and the display section 42 would be integrated.

The storage section 43 is comprised of, for example, nonvolatile memory such as a hard disk. Programs associated with various controls, data (e.g., data inputted into the control unit 30 from the input section 41), and the like are stored in the storage section 43. The control section 31 controls a liquid supplying tube and pumps 3a, 3b, and 3c based on information outputted from the calculation section 34.

The control section 31 controls at least one of thermostatic vessel, liquid supplying tube, and pumps 3a, 3b, and 3c based on at least one of data inputted into the control unit 30 from the input section 41, each output signal of a temperature sensor and pressure sensor inputted into the detection unit 32, and information outputted from the calculation section 34. The length of a liquid supplying tube can be controlled, for example, by switching a flow channel or the like.

Any flow rate varying section for changing the flow rate can be used in the system of the invention. In one embodiment, a flow rate varying section is a flow channel area varying apparatus 16b (e.g., throttle section) shown in FIG. 8, where the flow channel width D16 (and thus the flow channel area) can be changed. When the flow channel width D16 (flow channel area) is to be changed, the side walls of a flow channel is displaced to, for example, the inside or outside. For example, the flow rate after passing the flow rate varying section can be reduced by reducing the flow channel width D16 (and thus the flow channel area). In one embodiment, the flow channel area varying apparatus 16b (e.g., flow channel width D16) is controlled with the control unit 30.

The lipid particle manufacturing system of the invention can be further connected to an apparatus for adjusting the lipid particle concentration in a solution and/or an apparatus for replacing a solvent. For example, a dialyzer described in International Publication No. WO 2016/024510 can be used as such an apparatus. Connection of such apparatuses enables manufacture of lipid particles, concentration adjustment, and replacement of solvent in a single closed system as a final product, so that an aseptic environment can be readily achieved. A lipid particle manufacturing system can be connected to an apparatus for adjusting the lipid particle concentration in a solution and/or an apparatus for replacing a solvent directly with a tube, or indirectly by providing a constituent element other than a tube such as a container for storing a solution or the like therebetween.

FIG. 4 shows an example (dialyzer) of a hollow fiber membrane column 20 in a dialyzer. The hollow fiber dialysis column 20 has an assembly of numerous hollow fiber membranes 201a within the housing. Numerous pores 201b are formed on the hollow fiber membrane 201a (specifically, the side surface of a fiber). The hollow fiber dialysis column 20 has a first flow channel 201 where a lipid particle solution 11b (solution subjected to dialysis) flows inside the hollow fiber membrane 201a and a second flow channel 202 where an external solution 21a (dialysate) flows outside the follow fiber membrane 201a. An inlet 20a is provided on the upstream end of the first flow channel 201, and an outlet 20b is provided at the downstream end of the first flow channel 201. An inlet 20c is provided on the upstream end of the second flow channel 202, and an outlet 20d is provided on the downstream end of the second flow channel 202. The inlet 20c of the second flow channel 202 is disposed in the vicinity of the outlet 20b of the first flow channel 201, and the outlet 20d of the second flow channel 202 is disposed in the vicinity of the inlet 20a of the first flow channel 201.

The MWCO (Molecular Weight Cut Off) of the hollow fiber membrane 201a in the hollow fiber dialysis column 20 can be, for example, 3 kD or greater and 750 kD or less. The length D11 from the inlet 20a to the outlet 20b of the first flow channel 201 can be, for example, 10 cm or greater and 300 cm or less. A plurality of hollow fiber dialysis columns can be connected in the longitudinal direction (in series) to substantially form a long hollow fiber dialysis column 20. The inner diameter (inner diameter of a fiber) D13 of the hollow fiber membrane 201a can be, for example, 0.3 mm or greater and 2.0 mm or less. The pore 201b can have, for example, a diameter D14, which is less than the mean particle diameter D12 of lipid particles 101. The diameter D14 of the pore 201b can be, for example, 2 nm or greater and 75 nm or less. Examples of base materials of the hollow fiber membrane 201a include, but are not limited to, mPES (modified polyethersulfone), ME (mixed cellulose ester), PES (polyethersulfone), and PS (polysulfone). For example, Spectrum Laboratories' "MidiKros® module" can be used as the hollow fiber membrane column 20.

In one embodiment, when the lipid particle solution 11b is dialyzed, a pump 22a is actuated to allow the external solution 21a to flow outside the hollow fiber membrane 201a as shown in FIG. 4. For example, the external solution 21a can be the same solvent as the final product. In one embodiment, the external solution 21a does not need to flow outside the hollow fiber membrane 201a when dialyzing a lipid particle solution. In one embodiment, a dialyzer can have a flow channel where a filtrate produced by passing a lipid particle solution through the hollow fiber membrane 201a flows. In one embodiment, dialysis of a lipid particle solution can be tangential flow filtration (TFF) in which waste liquid flows in the direction that is orthogonal to the direction of flow of the lipid particle solution.

The pump 22a pressure feeds (supplies) the external solution 21a within a container 21 toward the hollow fiber dialysis column 20. The external solution 21a flows toward the hollow fiber dialysis column 20 (inlet 20c of the second flow channel 202) within a tube 22 by actuating the pump 22a, and flows outside of the hollow fiber membrane 201a in the second flow channel 202 along the hollow fiber membrane 201a. The external solution 21a flows from the inlet 20c to the outlet 20d of the second flow channel 202 and passes a tube 23 to be collected within a waste liquid container 24.

The direction of flow of the lipid particle solution 11b is preferably in the opposite direction (reverse direction) of the flow of the external solution 21a. The efficiency of dialysis can be improved by the lipid particle solution 11b and the external solution 21a flowing in opposite directions from each other.

As shown in FIG. 4, the lipid particles 101 in the lipid particle solution 11b are greater than the pore 201b, so that they cannot pass through the pore 201b. Meanwhile, organic microparticles 103 are smaller than the pore 201b, so that they can pass through the pore 201b. For this reason, the organic microparticles 103 contained in the lipid particle solution 11b are removed to the outside of the hollow fiber membrane 201a. A dispersion medium 102 in the lipid particle solution 11b also moves outside (second flow channel 202) from the inside (first flow channel 201) of the hollow fiber membrane 201a. Meanwhile, the external solution 21a moves inside (first flow channel 201) from the outside (second flow channel 202) of the hollow fiber membrane 201a.

The difference between the amount of movement of the dispersion medium 102 (amount of solution moving from the first flow channel 201 to the second flow channel 202) and the amount of movement of the external solution 21a (amount of solution moving from the second flow channel 202 to the first flow channel 201) (and thus the concentration of the solution subjected to dialysis) in the hollow fiber dialysis column 20 can be controlled by controlling the amount of lipid particle solution 11b (solution subjected to dialysis) entering the first flow channel 201 and the amount of lipid particle solution 11b (solution subjected to dialysis) leaving the first flow channel 201 while allowing a solution subjected to dialysis to flow in the first flow channel 201 of the hollow fiber membrane column 20 and the external solution 21a to flow in the second flow channel 202 and dialyzing the solution subjected to dialysis. The lipid particle solution 11b after dialysis passes through a tube 16 and flows into a collection section 17.

A dialyzer can have a control unit 30 shown in FIG. 5. The control unit 30 has the control section 31 and the detection section 32. The control section 31 and the detection section 32 are communicably connected to each other. A control unit for a dialyzer can be integral with or independent from a control unit for a lipid particle manufacturing apparatus. A dialyzer can have the same control unit as the control unit for a lipid particle manufacturing apparatus shown in FIGS. 3A and 3B.

In a dialyzer, the control unit 30 controls the concentration of a solution subjected to dialysis (lipid particle solution 11b after dialysis) flowing out from the outlet 20b of the first flow channel 201 based on the difference between the flow rate of a solution subjected to dialysis (lipid particle solution 11b before dialysis) at the inlet 20a of the first flow channel 201 (hereinafter, the first flow rate) and the flow rate of the solution subjected to dialysis (lipid particle solution 11b after dialysis) at the outlet 20b of the first flow channel 201 (hereinafter, the second flow rate).

For example, the organic microparticles 103 (FIG. 4) in the lipid particle solution 11b can be removed without hardly changing the concentration of the lipid particle solution 11b as shown in FIG. 6 with a ratio of flow rates before and after dialysis of 1.0 (first flow rate=second flow rate). While the lipid particle solution 11b flows in the first flow channel 201, the amount of dispersion medium 102 moving from the first flow channel 201 to the second flow channel 202 would be approximately the same as the amount of the dispersion medium 102 moving from the second flow channel 202 to the first flow channel 201.

For example, the lipid particle solution 11b can be concentrated while removing the organic microparticles 103 (FIG. 4) in the lipid particle solution 11b as shown in FIG. 7 with a ratio of flow rates before and after dialysis of less than 1.0 (first flow rate>second flow rate). In contrast, the lipid particle solution 11b can be diluted while removing the organic microparticles 103 in the lipid particle solution 11b with a ratio of flow rates before and after dialysis of greater than 1.0.

A dialyzer (purification section 15 or the like) can readily control the concentration of a solution subjected to dialysis flowing out from the hollow fiber dialysis column 20 by controlling a pump 16a with the control unit 30. As a result, a solution subjected to dialysis with a desired concentration can be obtained with high precision.

FIG. 9 shows an exemplary embodiment providing a container for storing a solution between a lipid particle manufacturing system and an apparatus for lipid particle concentration adjustment and/or replacement of a solvent for an indirect connection thereof. In this example, a lipid particle containing solution from a lipid particle manufacturing system first flows into a primary container. A constituent element for monitoring and/or controlling the flow volume and/or pressure can be provided as needed to a tube connecting constituent elements within the system. The pressure, temperature, and/or liquid volume within the primary container can be monitored and controlled with means of the detection thereof (e.g., weighing instrument) or the like. The solution stored in the primary container is then supplied to the apparatus for lipid particle concentration adjustment and/or replacement of a solvent. The lipid particle containing solution subjected to adjustment of the concentration and/or replacement of a solvent through the apparatus for lipid particle concentration adjustment and/or replacement of a solvent can be retrieved directly (FIG. 9A), or allowed to flow into the primary container or another container and recirculated within the system (FIGS. 9B and 9C). In one embodiment, a solution within the primary container attaining the desired lipid particle concentration and/or solution composition is retrieved. In one embodiment, the pressure, temperature, liquid volume, and/or liquid composition of the lipid particle-free solution (permeate or waste liquid) from the apparatus for lipid particle concentration adjustment and/or replacement of a solvent can be monitored and adjusted to the desired lipid particle concentration and/or solution composition based on the obtained information. In one embodiment, the permeate or waste liquid can be disposed, or reused after treatment as needed. In one embodiment, a flow channel for adding a dialysate (external solution) can be provided to the system, and the flow channel can be configured to add a dialysate (external solution) to the solution subjected to dialysis. In one embodiment, a tube where a dialysate (external solution) flows into the primary container can be connected to the primary container (FIG. 9C). In one embodiment, a tube where a dialysate (external solution) flows into the apparatus for lipid particle concentration adjustment and/or replacement of a solvent can be connected (FIGS. 9A and 9B). In one embodiment, the lipid particle concentration adjustment and replacement of a solvent can be performed while maintaining the liquid volume within the system constant by supplying a dialysate in the same amount as the permeate. The lipid particle concentration adjustment and replacement of a solvent can be performed after storing a lipid particle containing solution from the lipid particle manufacturing system in the primary container, or in parallel with the storage. The lipid particle concentration adjustment and replacement of a solvent can be performed in a plurality of steps or in a single step.

In one embodiment, the lipid particle solution 11b (solution subjected to dialysis) within the first flow channel 201 flows in the opposite direction of the flow of the external solution 21a within the second flow channel 202 in a dialyzer (purification section 15 or the like). The efficiency of dialysis can be improved with a dialyzer with such a configuration.

If the concentration of the manufactured lipid particle solution is too high, the storage stability of the lipid particle solution can deteriorate. A lipid particle solution at a desired concentration can be readily obtained with the dialyzer described above. When the concentration of a lipid particle solution is adjusted, the ratio of flow rates before and after dialysis is preferably 0.2 or greater and 5.0 or less, and more preferably 0.5 or greater and 2.0 or less. The concentration of a solution subjected to dialysis can be adjusted with a ratio of flow rates before and after dialysis of 0.2 or greater and 5.0 or less (more preferably 0.5 or greater and 2.0 or less) with high precision.

The amount of solution treated at once can be increased by increasing the inner diameter (inner diameter of fiber) D13 (FIG. 4) of the hollow fiber membrane 201a or connecting a plurality of hollow fiber membrane columns in parallel. The treated amount can be increased by increasing the flow rate of the solution subjected to dialysis at the inlet 20a of the first flow channel 201. The treated amount can be readily increased simply by adjusting the flow rate in such a method.

In one aspect, the system of the invention determines a condition for producing lipid particles loaded with a given drug so that the given drug has a desired mean particle size (and polydispersity index as needed). The condition is determined using at least one function among a function representing the relationship between the alcohol concentration of a primary diluting solution and the particle size of lipid particles, a function representing the relationship between a given time (time of retention) and the particle size of lipid particles, a function representing the relationship between the temperature of a mixing region (second or third) and/or a liquid supplying tube between mixing regions and the particle size of lipid particles, a function representing the relationship between the lipid concentration of a primary or secondary diluting solution and the particle size of lipid particles, a function representing the relationship between the Reynolds number at the liquid supplying tube between mixing regions and the particle size of lipid particles, and a function representing the relationship between the pressure in the liquid supplying tube between mixing regions and the particle size of lipid particles.

In one embodiment, a function representing the relationship between the alcohol concentration of a primary diluting solution and the particle size of lipid particles can be obtained by the following procedure. A first solution comprising a given drug, a given lipid, and a specific alcohol is mixed with a second solution comprising water to prepare a mixture with alcohol diluted to a predetermined concentration. In this regard, at least two predetermined concentrations are selected. The particle size of lipid particles is measured at a point where a certain time has elapsed after preparation (can be immediately after preparation) for each mixture. A function representing the relationship between the mean particle size of lipid particles (and polydispersity index as needed) and the diluted concentration can be created based on the measurement results. A function representing the relationship between the alcohol concentration of a secondary diluting solution and the particle size of lipid particle liposomes can be obtained in the same manner.

In one embodiment, a function representing the relationship between a given time (time of retention) and the particle size of lipid particles can be obtained by the following procedure. A first solution comprising a given drug, a given lipid, and specific alcohol is mixed with a second solution comprising water to prepare a mixture with alcohol diluted to a certain concentration. The particle size of lipid particles is measured at a point where a predetermined time has elapsed after preparation of the mixture. In this regard, at least two predetermined times are selected. A function representing the relationship between the mean particle size of lipid particles (and polydispersity index as needed) and the time passed after preparation can be created based on the measurement results. While the above is a description related to the time of retention from the first mixing region until reaching the second mixing region, a function representing the relationship between the time of retention from the second mixing region until reaching the third mixing region and the particle size of lipid particles can be obtained in the same manner.

For example, the mean particle size of lipid particles generally increases by loading an agent for hydrophobic agents (embedded in the liposome membrane or loaded inside micelles). For this reason, if the lipid composition is determined, the present invention generally expects a condition that results in agent free lipid particles with a mean particle size that is 20% to 30% smaller than the target particle size of the final formulation. Since hydrophilic agents such as Doxil can be manufactured as an agent-free lipid particle, this is further expected.

(General Technology)

The analytical approach, chemical approach, and pharmaceutical approach used herein are conventional and well known in the art and are described in, for example, (authored by Gregory Gregoriadis, Liposome Technology: Liposome Preparation and Related Techniques, Sep. 12, 2006 CRC Press, ISBN 9780849388217) and the like, the relevant portion (can be the entire document) of which is incorporated herein by reference.

As used herein, "or" is used when "at least one or more" of the listed matters in a sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

The present invention has been described while showing preferred embodiments to facilitate understanding. While the present invention is described hereinafter based on the Examples, the above descriptions and the following Examples are provided for the sole purpose of exemplification, not limitation of the present invention. Thus, the scope of the present invention is not limited to the embodiments and Examples that are specifically described herein and is limited only by the scope of claims.

EXAMPLES

The Examples are described hereinafter.

For reagents, the specific products described in the Examples were used. However, the reagents can be substituted with an equivalent product from another manufacturer (Sigma-Aldrich, Wako Pure Chemical, Nacalai Tesque, R & D Systems, USCN Life Science INC, or the like).

Abbreviations

In addition to the described abbreviations, the following abbreviations are also used herein.
DOPC: 2-dioleoyl-sn-glycero-3-phosphatidylcholine
DOPG: 2-dioleoyl-sn-glycero-3-phosphatidylglycerol
DPPC: dipalmitoylphosphatidylcholine
DPPG: 1,2-dipalmitoleoyl-sn-glycero-3-phosphoglycerol
HSPC: hydrogenated soybean phosphatidylcholine
DSPG: distearoyl phosphatidylglycerol
DMPG: dimyristoyl phosphatidylglycerol
MPEG 2000 DSPE: N-(carbonyl-methoxypolyethyleneglycol-2000)1,2-distearoyl-sn-glycero-3-phosphoethanolamine sodium salt
PDI: polydispersity index The polydispersity index and the mean particle size of lipid particles were measured using dynamic light scattering.

(Example 1) Relationship Between Alcohol Concentration and Particle Size (1-1)
The following solutions were prepared.
Solution A: 95.8 mg of HSPC, 31.9 mg of Cholesterol, and 31.9 mg of MPEG 2000 DSPE were dissolved into 6 ml of ethanol
Solution B: maltose was dissolved into 10 mM sodium phosphate buffer (pH 6.5) at a final concentration of 10% (W/V).

Figure 10B:
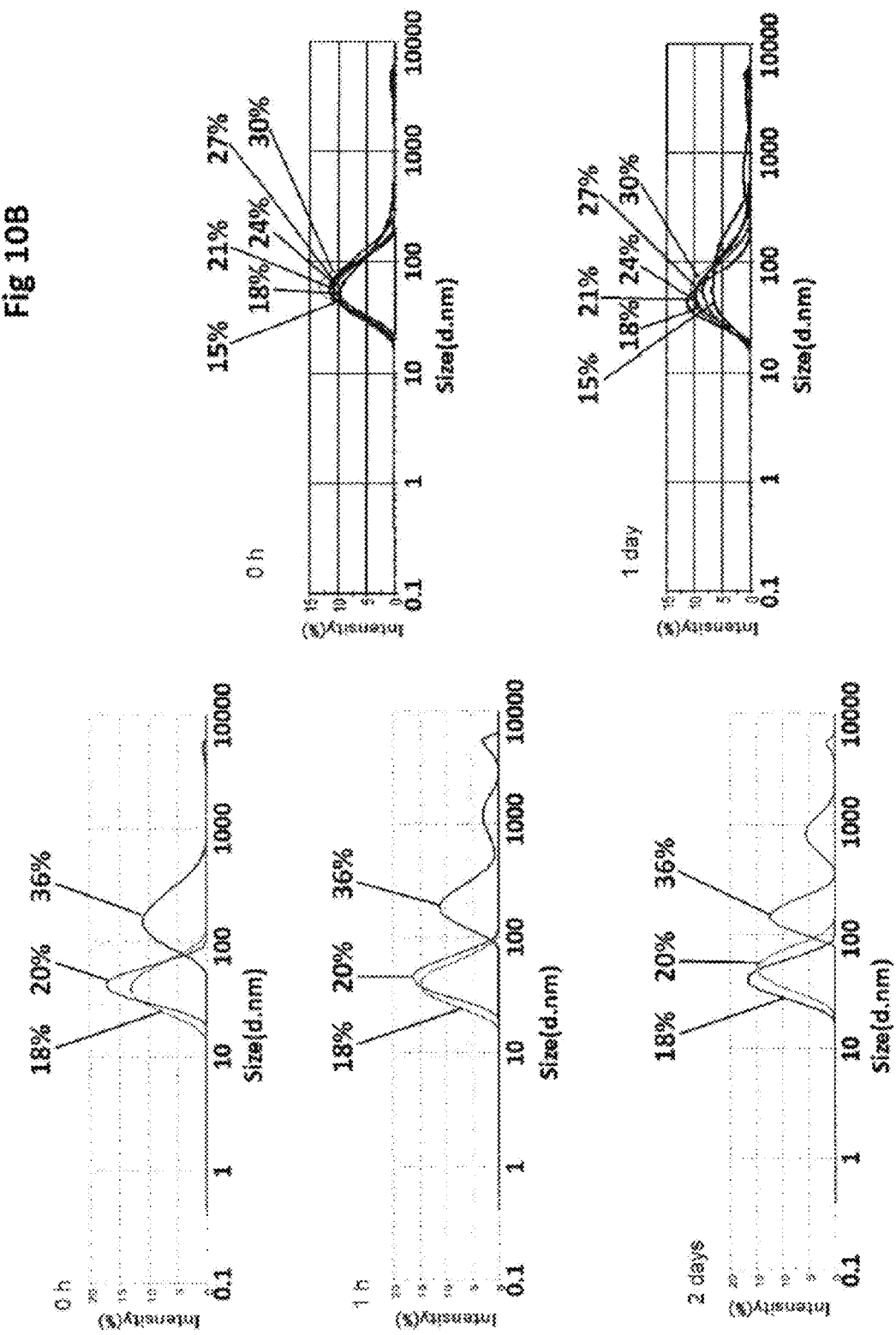
FIG. 10B is a diagram showing a change in the particle size distribution when using HSPC:Cholesterol:DSPG (2.0:1.0:0.8) as the lipid composition (molar ratio). The left side shows the particle size distribution of liposomes immediately after preparation and 1 hour after preparation at ethanol concentrations of 12%, 15%, 18%, 21%, 24%, and 27%. The right side shows the particle size distribution of liposomes immediately after preparation and 1 day after preparation at ethanol concentrations of 15%, 18%, 21%, 24%, 27%, and 30%.

Solution A and solution B were mixed in a 85° C. warm bath so that the ethanol concentrations (V/V) would be 12%, 18%, 27%, 36%, 39%, 42%, and 46%, and then incubated. The mean particle size and polydispersity index were observed immediately after mixing, 3 hours after mixing, and 3 days after mixing. The results are shown in the following table and the left side of FIG. 10A.

TABLE 1

| Ethanol concentration % (V/V) | | 12% | 18% | 27% | 36% | 39% | 42% | 46% |
|---|---|---|---|---|---|---|---|---|
| Mean particle size (nm) | | 74.74 | 65.63 | 74.32 | 161.1 | 98.76 | 132.2 | 165.4 |
| Pdl | | 0.081 | 0.062 | 0.032 | 0.073 | 0.063 | 0.086 | 0.112 |
| After 1 hour | Mean particle size (nm) | 74.61 | 66.54 | 86.54 | 226.2 | 322.8 | 616 | 722.1 |
| | Pdl | 0.062 | 0.038 | 0.03 | 0.231 | 0.356 | 0.505 | 0.519 |
| After 3 days | Mean particle size (nm) | 75.03 | 67.83 | 90.57 | 209.1 | 310 | 397.8 | 488.5 |
| | Pdl | 0.078 | 0.055 | 0.028 | 0.254 | 0.377 | 0.369 | 0.223 |
| Stability | | ○ | ○ | x | x | x | x | x |

Further, solution A was replaced with an ethanol solution prepared by dissolving solution A: 95.8 mg of HSPC, 31.9 mg of Cholesterol, 31.9 mg of MPEG 2000 DSPE, and 50 mg of α-Galactosylceramide into 6 ml of ethanol, and similarly mixed so that the ethanol concentrations (V/V) would be 15%, 18%, 21%, 24%, 27%, and 30%, and then incubated. The mean particle size and polydispersity index were observed immediately after mixing and 1 day after mixing. The results are shown in the following table and the right side of FIG. 10A.

TABLE 2

| Ethanol concentration % (V/V) | 15% | 18% | 21% | 24% | 27% | 30% |
|---|---|---|---|---|---|---|
| Mean particle size (nm) | 52.21 | 52.87 | 53.9 | 54.94 | 55.93 | 55.25 |
| Pdl | 0.047 | 0.073 | 0.121 | 0.123 | 0.135 | 0.133 |

TABLE 2-continued

| After 1 day | Mean particle size (nm) | 51.35 | 52.21 | 60.69 | 61.99 | 70.86 | 71.48 |
|---|---|---|---|---|---|---|---|
| | PdI | 0.071 | 0.079 | 0.141 | 0.185 | 0.229 | 0.229 |
| Stability | | ○ | ○ | x | x | x | x |

(1-2)

The following solutions were prepared.

Solution A: 170.4 mg of HSPC, 41.6 mg of Cholesterol, and 67.2 mg of DSPG were dissolved into 18 ml of ethanol Solution B: maltose was dissolved into 10 mM sodium phosphate buffer (pH 6.5) at a final concentration of 10% (W/V).

Solution A and solution B were mixed so that the ethanol concentration (V/V) would be 12%, 15%, 18%, 21%, 24%, and 27%, and then incubated in the same manner as (1-1).

The mean particle size and polydispersity index were observed immediately after mixing, 1 hour after mixing, and 2 days after mixing. The results are shown in the following table and the left side of FIG. 10B.

TABLE 3

| Ethanol concentration % (V/V) | | 18% | 20% | 36% |
|---|---|---|---|---|
| Mean particle size (nm) | | 37.69 | 40.96 | 158.6 |
| PdI | | 0.14 | 0.08 | 0.209 |
| After 1 hour | Mean particle size (nm) | 37.53 | 43.81 | 269.5 |
| | PdI | 0.116 | 0.095 | 0.486 |
| After 3 days | Mean particle size (nm) | 38.76 | 48.26 | 238.3 |
| | PdI | 0.079 | 0.108 | 0.406 |
| Stability | | ○ | x | x |

Further, solution A was replaced with an ethanol solution prepared by dissolving solution A: 170.4 mg of HSPC, 41.6 mg of Cholesterol, 67.2 mg of DSPG, and 50 mg of α-Galactosylceramide into 18 ml of ethanol, and similarly mixed so that the ethanol concentrations (V/V) would be 15%, 18%, 21%, 24%, 27%, and 30%, and then incubated. The mean particle size and polydispersity index were observed immediately after mixing and 1 day after mixing. The results are shown in the following table and the right side of FIG. 10B.

TABLE 4

| Ethanol concentration % (V/V) | | 15% | 18% | 21% | 24% | 27% | 30% |
|---|---|---|---|---|---|---|---|
| Mean particle size (nm) | | 52.91 | 55.41 | 55.97 | 58.03 | 59 | 60.95 |
| PdI | | 0.115 | 0.114 | 0.134 | 0.183 | 0.225 | 0.288 |
| After 1 day | Mean particle size (nm) | 52.67 | 55.47 | 70.84 | 82.91 | 90.86 | 102.92 |
| | PdI | 0.117 | 0.104 | 0.241 | 0.255 | 0.389 | 0.445 |
| Stability | | ○ | ○ | x | x | x | x |

(1-3)

The following solutions were prepared.

Solution A: 96 mg of DOPC, 97 mg of DOPG, 90 mg of DPPC, 91 mg of DPPG, and 126 mg of Cholesterol were dissolved into 4 ml of ethanol Solution B: maltose was dissolved into 10 mM sodium phosphate buffer (pH 6.5) at a final concentration of 10% (W/V).

Solution A and solution B were mixed so that the ethanol concentrations (V/V) would be 17%, 18%, 25%, 33%, and 35%, and then incubated in the same manner as (1-1). The mean particle size and polydispersity index were observed immediately after mixing and 1 hour after mixing. The results are shown in the following table and FIG. 10C.

TABLE 5

| Ethanol concentration % (V/V) | | 17% | 18% | 25% | 33% | 35% |
|---|---|---|---|---|---|---|
| Mean particle size (nm) | | 41.46 | 56.74 | 69.07 | 107.7 | 114.9 |
| PdI | | 0.091 | 0.171 | 0.091 | 0.04 | 0.069 |
| After 1 hour | Mean particle size (nm) | | 57.92 | 78.83 | 147.6 | 149.4 |
| | PdI | | 0.073 | 0.078 | 0.159 | 0.169 |
| Stability | | | ○ | x | x | x |

It was found from these experiments that the particle size of lipid particles changes depending on the ethanol dilution concentration. It was also shown that the mean particle size increases with time after preparation of lipid particles.

(Example 2) Relationship Between Second Stage Alcohol Dilution Concentration and Particle Size (2-1)

The following solutions were prepared.

Solution A: 95.8 mg of HSPC, 31.9 mg of Cholesterol, and 31.9 mg of MPEG 2000 DSPE were dissolved into 6 ml of ethanol Solution B: maltose was dissolved into 10 mM sodium phosphate buffer (pH 6.5) at a final concentration of 10% (W/V).

Figure 11A:
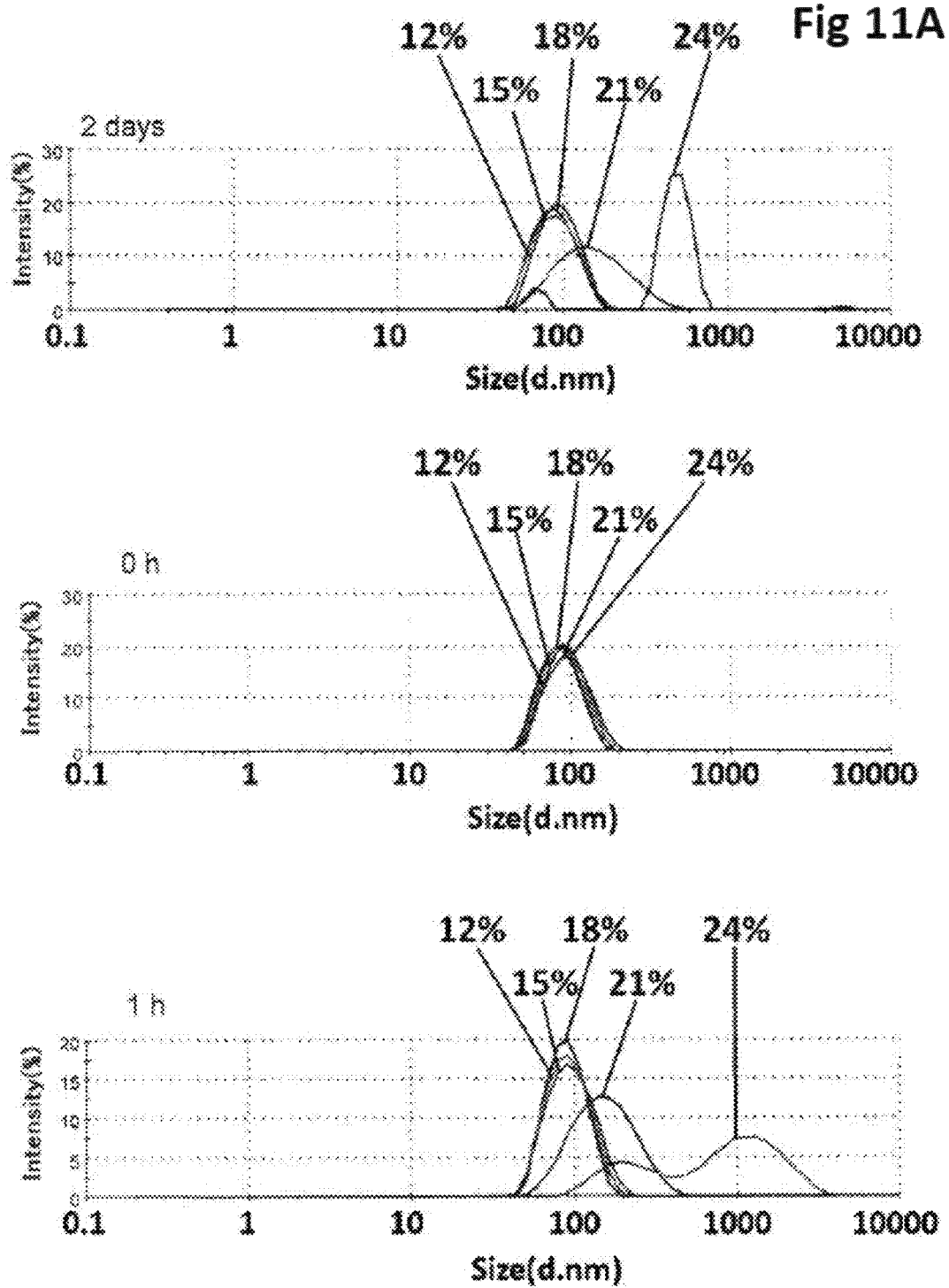
FIG. 11A is a diagram showing the particle size distribution immediately after, 1 hour after, 1 day after, and 2 days after the preparation of liposomes prepared at each of the secondary dilution concentrations when using the composition of HSPC, Cholesterol, and MPEG 2000 DSPE described in Examples 2-1.

6 mL of solution A and 10.7 mL of solution B were mixed so that the ethanol concentration would be 36% (V/V), and stirred for 30 seconds in an 85° C. warm bath. Solution B was then further added to prepare a secondary diluting solution so that the ethanol concentrations would be 12%, 15%, 18%, 21%, 24%, and 27%, and then the diluting solution was incubated at room temperature or 4° C. The mean particle size and polydispersity index were observed immediately after the preparation of the secondary diluting solution, after 1 hour, after 3 hours, after 1 day, and after 2 days. The results are shown in the following table and FIG. 11A.

TABLE 6

| Secondary diluting solution ethanol concentration % (V/V) | | 12% | 15% | 18% | 21% | 24% |
|---|---|---|---|---|---|---|
| Mean particle size (nm) | | 74.8 | 80.47 | 91.45 | 139.2 | 522.4 |
| PdI | | 0.04 | 0.082 | 0.098 | 0.159 | 0.532 |
| After 1 hour | Mean particle size (nm) | 78.6 | 82.7 | 95.17 | 142.8 | 426.3 |
| | PdI | 0.033 | 0.055 | 0.106 | 0.19 | 0.565 |
| After 2 days | Mean particle size (nm) | 80.2 | 84.4 | 94.86 | 141.1 | 638.1 |
| | PdI | 0.048 | 0.076 | 0.068 | 0.198 | 0.467 |
| Stability | | ○ | ○ | ○ | x | x |

(2-2)

The following solutions were prepared.

Solution A: 170.4 mg of HSPC, 41.6 mg of Cholesterol, and 67.2 mg of DSPG were dissolved into 18 ml of ethanol Solution B: maltose was dissolved into 10 mM sodium phosphate buffer (pH 6.5) at a final concentration of 10% (W/V).

18 mL of solution A and 32 mL of solution B were mixed so that the ethanol concentration would be 36% (V/V), and stirred for 30 seconds in an 85° C. warm bath. Solution B was then further added to prepare a secondary diluting solution so that the ethanol concentrations (V/V) would be 12%, 15%, 18%, 21%, 24%, and 27%, and then the diluting solution was incubated. The mean particle size and polydispersity index were observed immediately after the preparation of the secondary diluting solution, after 1 hour, after 1 day, and after 2 days. The results are shown in the following table and FIG. 11B.

TABLE 7

| Secondary diluting solution ethanol concentration % (V/V) | | 12% | 15% | 18% | 21% | 24% | 27% |
|---|---|---|---|---|---|---|---|
| Mean particle size (nm) | | 51.21 | 50.41 | 48.34 | 50.76 | 62.45 | 103.7 |
| PdI | | 0.086 | 0.072 | 0.072 | 0.053 | 0.065 | 0.165 |
| After 1 hour | Mean particle size (nm) | 56.17 | 50.08 | 48.87 | 62.8 | 128.3 | 145 |
| | PdI | 0.147 | 0.047 | 0.058 | 0.175 | 0.482 | 0.457 |
| After 2 days | Mean particle size (nm) | 51.57 | 50.22 | 49.75 | 68.9 | 128.2 | 143 |
| | PdI | 0.046 | 0.07 | 0.061 | 0.326 | 0.509 | 0.433 |
| Stability | | ○ | ○ | ○ | x | x | x |

These experiments show that lipid particles stabilize when the secondary dilution concentration of ethanol is a certain concentration (about 18%) or less, whereas lipid particles destabilize at a greater concentration. It is expected in view of the above that lipid particles with a desired particle size distribution can be stably provided by performing an operation that would result in a desired particle size at an alcohol concentration at which lipid particles destabilize and then adjusting the alcohol concentration to a concentration where lipid particles stabilize. It is also shown that the alcohol concentration (fluidity changing point) where lipid particles start destabilizing possibly does not change regardless of the lipid particle composition or the presence/absence of a drug loaded in lipid particles.

(Example 3) Relationship Between Lipid Concentration in Alcohol and Particle Size (3-1)

The following solutions were prepared.

Solution A: 95.8 mg of HSPC, 31.9 mg of Cholesterol, and 31.9 mg of MPEG 2000 DSPE were dissolved into 1, 2, 3, 4, and 6 ml of ethanol Solution B: maltose was dissolved into 10 mM sodium phosphate buffer (pH 6.5) at a final concentration of 10% (W/V).

Figure 12A:
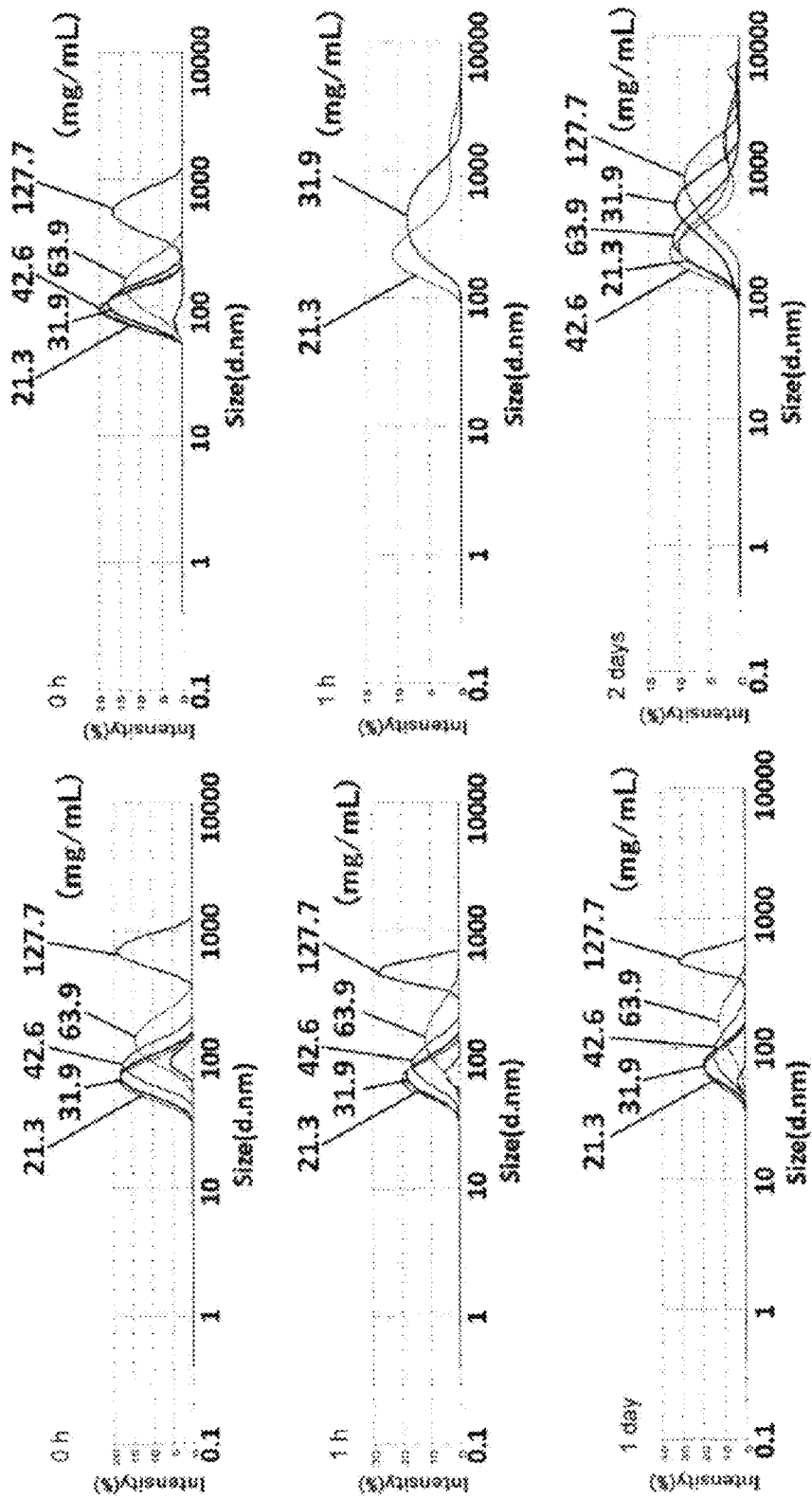
FIG. 12A is a diagram showing the particle size distribution at 18% or 36% dilution concentration of liposomes prepared at each lipid concentration when using HSPC:Cholesterol:MPEG 2000 DSPE (56:39:5) as the lipid composition (molar ratio).
Figure 12B:
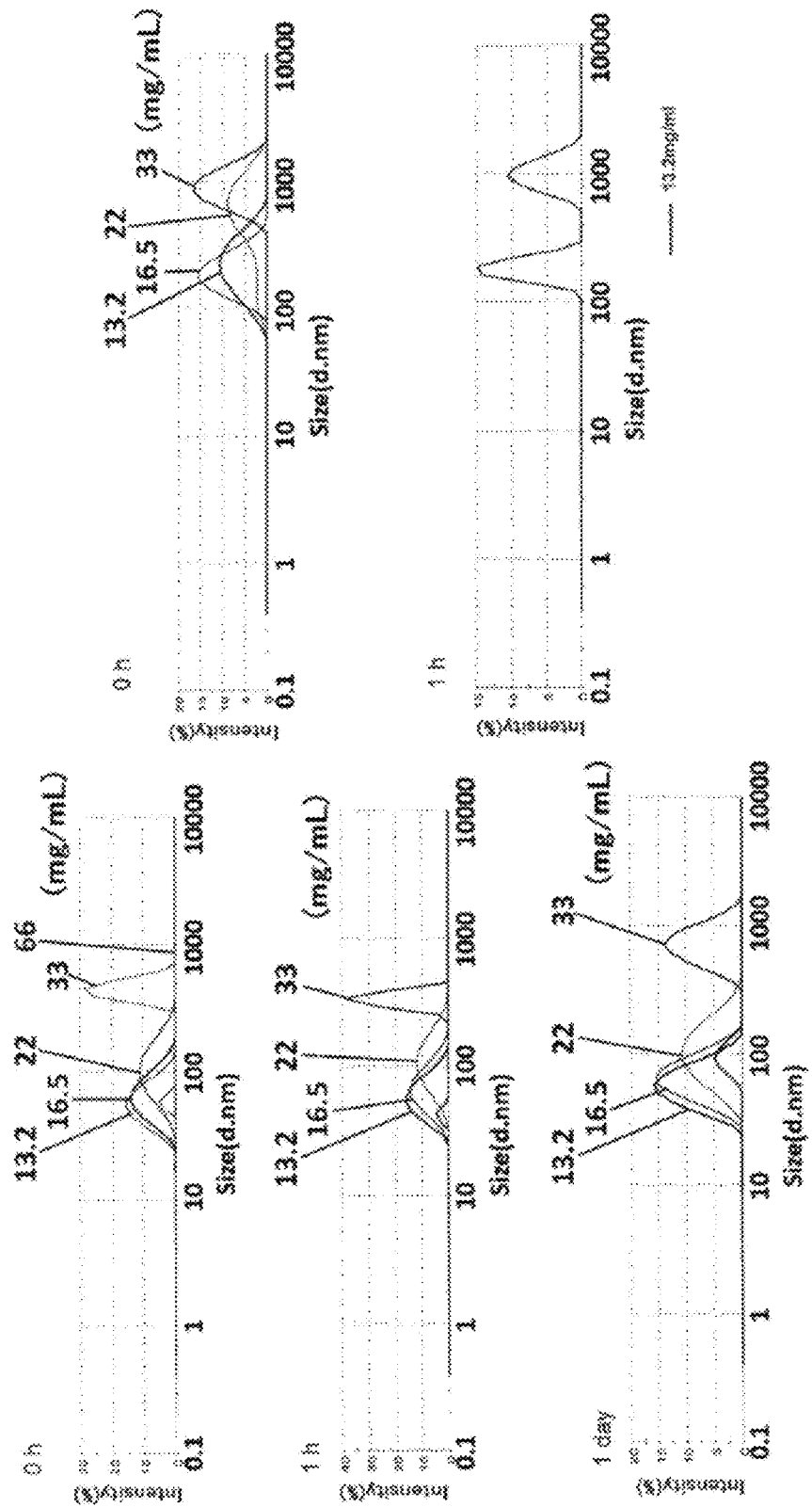
FIG. 12B is a diagram showing the particle size distribution at 18% or 36% dilution concentration of liposomes prepared at each lipid concentration when using HSPC:Cholesterol:DSPG (2.0:1.0:0.8) as the lipid composition (molar ratio).

Solution A and solution B were mixed in an 85° C. warm bath so that the ethanol concentrations (V/V) would be 18% and 36%, and then incubated. The mean particle size and polydispersity index were observed immediately after mixing, 1 hour after mixing, 1 day after mixing, and 2 days after mixing. The results are shown in the following tables and FIG. 12A.

TABLE 8

| | Ethanol concentration 18% | | | | |
|---|---|---|---|---|---|
| Lipid concentration (mg/ml) | 127.7 | 63.9 | 42.6 | 31.9 | 21.3 |
| Mean particle size (nm) | 512.9 | 135.8 | 89.02 | 71.7 | 67.57 |
| Pdl | 0.513 | 0.14 | 0.093 | 0.069 | 0.062 |
| After 1 hour Mean particle size (nm) | 713.6 | 137.7 | 88.84 | 71.82 | 68.69 |
| Pdl | 0.536 | 0.152 | 0.083 | 0.066 | 0.053 |
| After 1 day Mean particle size (nm) | 779.1 | 141.2 | 89.38 | 73.23 | 68.89 |
| Pdl | 0.547 | 0.149 | 0.129 | 0.063 | 0.058 |
| Stability | x | x | Δ | ○ | ○ |

TABLE 9

| | Ethanol concentration 36% | | | | |
|---|---|---|---|---|---|
| Lipid concentration (mg/ml) | 127.7 | 63.9 | 42.6 | 31.9 | 21.3 |
| Mean particle size (nm) | 479.1 | 138.2 | 98.28 | 105.1 | 95.88 |
| Pdl | 0.319 | 0.123 | 0.065 | 0.067 | 0.065 |
| After 1 hour Mean particle site (nm) | | | | 385.4 | 269.2 |
| Pdl | | | | 0.25 | 0.256 |
| After 2 days Mean particle size (nm) | 666.4 | 273.7 | 251.1 | 393 | 285.1 |
| Pdl | 0.298 | 0.213 | 0.269 | 0.25 | 0.325 |
| Stability | x | x | x | x | x |

(3-2)

The following solutions were prepared.
Solution A: 47.3 mg of HSPC, 11.6 mg of Cholesterol, and 18.7 mg of DSPG were dissolved into 1, 2, 3, 4, and 5 ml of ethanol
Solution B: maltose was dissolved into 10 mM sodium phosphate buffer (pH 6.5) at a final concentration of 10% (W/V).

Solution A and solution B were mixed so that the ethanol concentrations (V/V) would be 18% and 36%, and then incubated in the same manner as (3-1). The mean particle size and polydispersity index were observed immediately after mixing and 1 hour after mixing. The results are shown in the following tables and FIG. 121B.

(3-3)

The following solutions were prepared.
Solution A: 96 mg of DOPC, 97 mg of DOPG, 90 mg of DPPC, 91 mg of DPPG, and 126 mg of Cholesterol were dissolved into 3, 3.5, 4, and 5 ml of ethanol
Solution B: maltose was dissolved into 10 mM sodium phosphate buffer (pH 6.5) at a final concentration of 10% (W/V).

Solution A and solution B were mixed so that the ethanol concentration would be 25% (V/V), and then incubated in the same manner as (3-1). The mean particle size and polydispersity index were observed immediately after mixing, 1 hour after mixing, and after 1.5 hours. The results are shown in the following table and FIG. 12C.

TABLE 10

| | Ethanol concentration 18% | | | | |
|---|---|---|---|---|---|
| Lipid concentration (mg/ml) | 66 | 33 | 22 | 16.5 | 13.2 |
| Mean particle size (nm) | 15690 | 558.5 | 91.43 | 60.17 | 52.88 |
| Pdl | 0.105 | 0.603 | 0.181 | 0.12 | 0.106 |
| After 1 hour Mean particle size (nm) | | 446.8 | 107 | 71.59 | 54.16 |
| Pdl | | 0.456 | 0.189 | 0.162 | 0.098 |
| After 1 day Mean particle size (nm) | | 406.8 | 93.4 | 62.7 | 54.55 |
| Pdl | | 0.732 | 0.189 | 0.112 | 0.097 |
| Stability | | x | ○ | ○ | ○ |

TABLE 11

| | Ethanol concentration 36% | | | |
|---|---|---|---|---|
| Lipid concentration (mg/ml) | 33 | 22 | 16.5 | 13.2 |
| Mean particle size (nm) | 768.6 | 388.9 | 182.1 | 188.9 |
| Pdl | 0.248 | 0.41 | 0.136 | 0.185 |
| After 1 hour Mean particle size (nm) | | | | 377.5 |
| Pdl | | | | 0.694 |
| Stability | | | | x |

TABLE 12

| Lipid concentration (mg/ml) | | 124.7 | 106.9 | 93.5 | 74.8 |
|---|---|---|---|---|---|
| Mean particle size (nm) | | 108.3 | 88.5 | 69.07 | 57.92 |
| Pdl | | | 0.183 | 0.116 | 0.091 | 0.073 |
| After 1 hour | Mean particle size (nm) | | 114.9 | | 78.83 | |
| | Pdl | | 0.069 | | 0.078 | |
| After 1.5 hours | Mean particle size (nm) | | | | 81.77 | |
| | Pdl | | | | 0.088 | |
| Stability | | | Δ | | x | |

(3-4)

The following solutions were prepared.
Solution A: 96 mg of DOPC, 97 mg of DOPG, 90 mg of DPPC, 91 mg of DPPG, and 126 mg of Cholesterol were dissolved into 4, 5, and 6 ml of ethanol
Solution B: maltose was dissolved into 10 mM sodium phosphate buffer (pH 6.5) at a final concentration of 10% (W/V).

Figure 13:
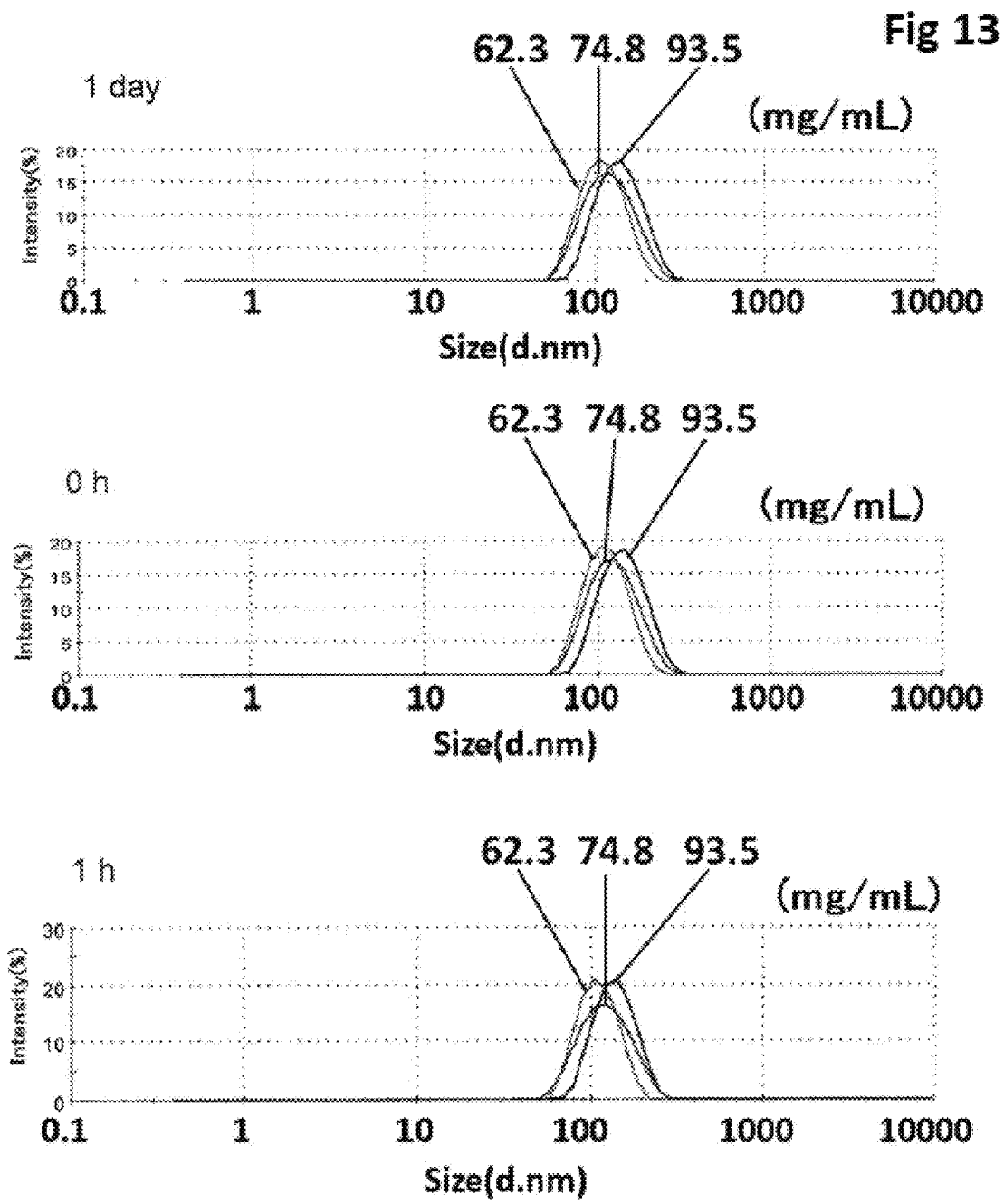
FIG. 13 FIG. 13 is a diagram showing the particle size distribution at 36% primary dilution concentration and 18% secondary dilution concentration of liposomes prepared at each lipid concentration when using DOPC:DOPG:DPPC: DPPG:Cholesterol (1:1:1:1:2.7) as the lipid composition (molar ratio).

Solution A and solution B were mixed so that the ethanol concentration would be 36% (V/V) in the same manner as (3-1). Solution B was then further added to prepare a secondary diluting solution so that the ethanol concentration would be 18%, and then the diluting solution was incubated. The mean particle size and polydispersity index were observed after the preparation of the secondary diluting solution. The results are shown in the following table and FIG. 13.

TABLE 13

| Lipid concentration (mg/ml) | | 93.5 | 74.8 | 62.3 |
|---|---|---|---|---|
| Mean particle size (nm) | | 134.1 | 115.4 | 106.3 |
| Pdl | | 0.061 | 0.085 | 0.059 |
| After 1 hour | Mean partide size (nm) | 134.4 | 114 | 106.2 |
| | Pdl | 0.038 | 0.093 | 0.066 |
| After 1 day | Mean particle size (nm) | 132.6 | 113.6 | 105.2 |
| | Pdl | 0.076 | 0.095 | 0.069 |
| Stability | | ○ | ○ | ○ |

It was found from these experiments that the particle size of lipid particles tend to be larger for higher lipid concentration, and the fluidity changing point is constant regardless of the lipid concentration.

(Example 4) Relationship Between Time Elapsed after First Alcohol Dilution and Particle Size (4-1)

The following solutions were prepared.
Solution A: 96 mg of DOPC, 97 mg of DOPG, 90 mg of DPPC, 91 mg of DPPG, and 126 mg of Cholesterol were dissolved into 4 ml of ethanol
Solution B: maltose was dissolved into 10 mM sodium phosphate buffer (pH 6.5) at a final concentration of 10% (W/V).

A lipid particle producing apparatus was configured to allow solution A and solution B to flow on separate flow channels, mix the solutions with a first mixer to prepare a first diluting solution, allow the first diluting solution to flow in a liquid supplying tube, and mix the first diluting solution with solution B in a second mixer to prepare a second diluting solution. In this regard, the flow volume was adjusted so that the ethanol concentration of the first diluting solution was 36% (V/V) and the ethanol concentration of the second diluting solution was 18% (V/V).

The mean particle size and polydispersity index were observed after changing the flow rate and the length of the liquid supplying tube. The results are shown in the following table and FIG. 14.

TABLE 14

| Primary diluting solution flow rate (ml/min) | Flow channel (m) | Time of retention (min:sec) | Mean particle size (nm) | Pdl |
|---|---|---|---|---|
| 16.5 | 40 | 1:54 | 88.39 | 0.109 |
| 8.25 | 20 | | 90.02 | 0.063 |
| 11 | 40 | 2:51 | 115.4 | 0.064 |
| 5.5 | 20 | | 111.5 | 0.06 |
| 8.25 | 40 | 3:48 | 131.4 | 0.064 |
| 4.13 | 20 | | 130.8 | 0.09 |

The experiment shows that lipid particles with the same particle size are formed at different flow rates/flow channel length, as long as the time of retention (time until second dilution) is the same.

(4-2)

The following solutions were prepared.

Solution A: 95.8 mg of HSPC, 31.9 mg of Cholesterol, and 31.9 mg of MPEG 2000 DSPE were dissolved into 3 ml of ethanol Solution B: maltose was dissolved into 10 mM sodium phosphate buffer (pH 6.5) at a final concentration of 10% (W/V).

A lipid particle producing apparatus was configured in the same manner as (4-1). The flow volume was adjusted so that the ethanol concentration of the first diluting solution was 36% (V/V) and the ethanol concentration of the second diluting solution was 18% (V/V). The steps from mixing in the first mixer to preparing the secondary diluting solution were performed under an 85° C. heated condition.

Figure 15A:
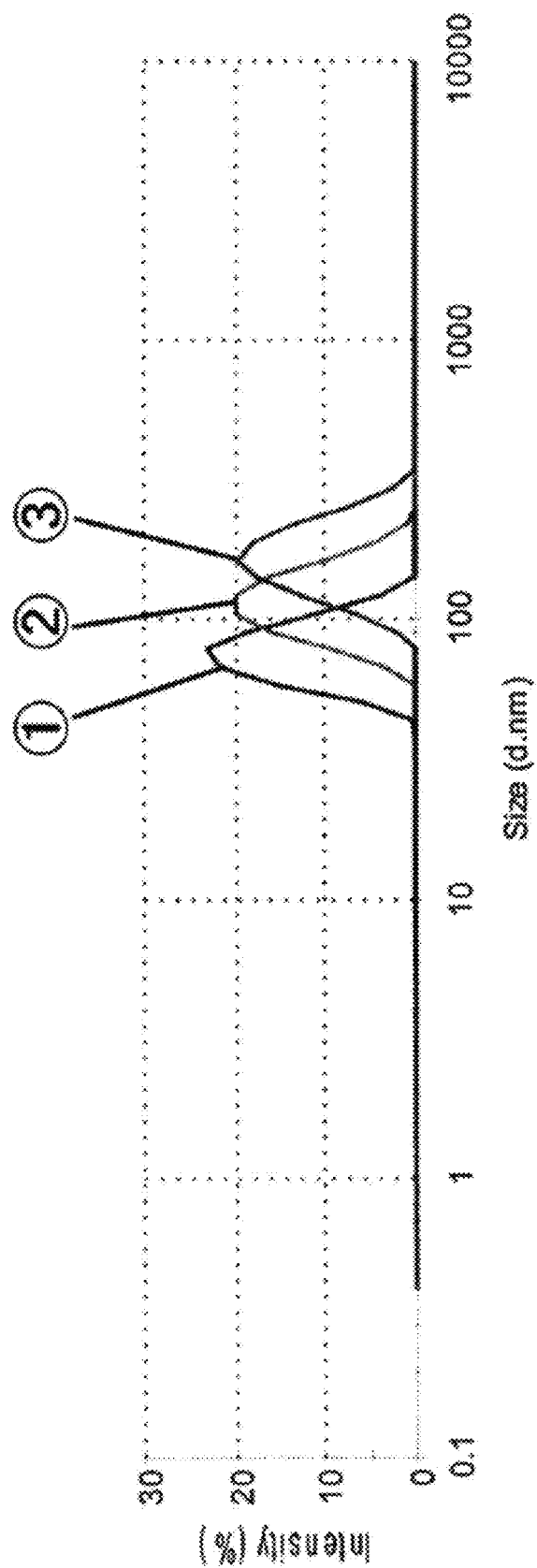
FIG. 15A is a diagram showing the particle size distribution of liposomes prepared at each flow rate (time of retention) when using HSPC:Cholesterol:MPEG 2000 DSPE (56:39:5) as the lipid composition (molar ratio).

The mean particle size and polydispersity index were observed after changing the flow rate. The results are shown in the following table and FIG. 15A.

TABLE 15

| | | ① | ② | ③ |
|---|---|---|---|---|
| Primary dilution | Solvent A (ml/min) | 6 | 1 | 0.2 |
| | Solvent B (ml/min) | 10.7 | 1.78 | 0.36 |
| Secondary dilution | Solvent B (ml/min) | 16.7 | 2.78 | 0.56 |
| Time of retention (min:sec) | | 0:28 | 2:49 | 14:01 |
| Mean particle size (nm) | | 75.03 | 111.9 | 160.5 |
| Pdl | | 0.028 | 0.049 | 0.053 |

(4-3)

The following solutions were prepared.

Solution A was changed to an ethanol solution with 96 mg of DOPC, 97 mg of DOPG, 90 mg of DPPC, 91 mg of DPPG, and 126 mg of Cholesterol dissolved into 4 ml of ethanol, and the same experiment as (4-2) was conducted. The results are shown in the following table and FIG. 15B.

TABLE 16

|  | | ① | ② | ③ |
|---|---|---|---|---|
| Primary dilution | Solvent A (ml/min) | 8 | 4 | 0.8 |
|  | Solvent B (ml/min) | 14 | 7 | 1.4 |
| Secondary dilution | Solvent B (ml/min) | 22 | 11 | 2.2 |
| Time of retention (min:sec) | | 1:25 | 2:51 | 14:16 |
| Mean particle size (nm) | | 98.23 | 115.4 | 166.1 |
| PdI | | 0.034 | 0.064 | 0.039 |

(4-4)
The following solutions were prepared.
Solution A: 96 mg of DOPC, 97 mg of DOPG, 90 mg of DPPC, 91 mg of DPPG, and 126 mg of Cholesterol were dissolved into 4 ml of ethanol
Solution B: maltose was dissolved into 10 mM sodium phosphate buffer (pH 6.5) at a final concentration of 10% (W/V).
A lipid particle producing apparatus was configured in the same manner as (4-1). In this regard, the flow volume was adjusted so that the ethanol concentration of the first diluting solution was 36% (V/V) and the ethanol concentration of the second diluting solution was 18% (V/V).
The mean particle size and polydispersity index were observed after adjusting the flow rate and the length of the liquid supplying tube so that the time of retention would be the time shown in the following table. The results are shown in the following table and FIG. 16A.

TABLE 17

| Time of retention (min:sec) | | 0:30 | 1:00 | 2:00 | 5:00 | 15:00 | 30:00 |
|---|---|---|---|---|---|---|---|
| Mean particle size (nm) | | 78.45 | 102 | 134.1 | 148.9 | 152.9 | 177.8 |
| PdI | | 0.093 | 0.091 | 0.061 | 0.049 | 0.082 | 0.148 |
| After 1 hour | Mean particle size (nm) | 79.08 | 7 | 134.4 | 149.1 | 154.5 | 181.1 |
|  | PdI | 0.102 | | 0.038 | 0.061 | 0.042 | 0.13 |
| After 2 days | Mean particle size (nm) | 79.19 | 104.2 | 132.6 | 150.4 | 155.9 | 184.1 |
|  | PdI | 0.093 | 0.075 | 0.076 | 0.076 | 0.062 | 0.143 |

(4-5)
The following solutions were prepared.
Solution A: 47.3 mg of HSPC, 11.6 mg of Cholesterol, and 18.7 mg of DSPG were dissolved into 18 ml of ethanol
Solution B: maltose was dissolved into 10 mM sodium phosphate buffer (pH 6.5) at a final concentration of 10% (W/V).
A lipid particle producing apparatus was configured in the same manner as (4-1). In this regard, the flow volume was adjusted so that the ethanol concentration of the first diluting solution was 36% (V/V) and the ethanol concentration of the second diluting solution was 18% (V/V).
The mean particle size and polydispersity index were observed after adjusting the flow rate and the length of the liquid supplying tube so that the time of retention would be the time shown in the following table. The results are shown in the following table and FIG. 16B.

TABLE 18

| Time of retention (min:sec) | | 0:30 | 1:00 | 2:00 | 5:00 | 15:00 |
|---|---|---|---|---|---|---|
| Particle size (nm) | | 48.34 | 51.12 | 56.72 | 66.04 | 60.63 |
| PdI | | 0.072 | 0.047 | 0.06 | 0.029 | 0.04 |
| After 1 hour | Particle size (nm) | 48.87 | 51.17 | 55.98 | 63.28 | 59.8 |
|  | PdI | 0.058 | 0.018 | 0.051 | 0.058 | 0.022 |
| After 2 days | Particle size (nm) | 49.75 | 51.15 | 57.13 | 66.3 | 60.68 |
|  | PdI | 0.061 | 0.038 | 0.078 | 0.089 | 0.043 |

These experiments show that the particle size of lipid particles can be increased by extending the time of retention. Further, the increase in PdI with the increase in particle size was low.

(Example 5) Relationship Between Temperature and Particle Size

The following solutions were prepared.
Solution A: 95.8 mg of HSPC, 31.9 mg of Cholesterol, and 31.9 mg of MPEG 2000 DSPE were dissolved into 6 ml of ethanol
Solution B: maltose was dissolved into 10 mM sodium phosphate buffer (pH 6.5) at a final concentration of 10% (W/V).
A lipid particle producing apparatus was configured to allow solution A and solution B to flow on separate flow channels, mix the solutions with a first mixer to prepare a first diluting solution, allow the first diluting solution to flow in a liquid supplying tube, and mix the first diluting solution with solution B in a second mixer to prepare a second diluting solution. In this regard, solution A (6 mL/min) and solution B (10.7 mL/min) were mixed with the first mixer to prepare the first diluting solution with an ethanol concentration of 36% (V/V), and solution B (16.7 mL/min) was added and mixed with the second mixer to prepare the second diluting solution with an ethanol concentration of 18% (V/V).

The mean particle size and polydispersity index were observed after using a 50° C. or 85° C. heating condition from the steps of mixing in the first mixer to preparing the secondary diluting solution. The results are shown in the following table and FIG. 17.

TABLE 19

| Temperature (° C.) | 50 | 85 |
|---|---|---|
| Flow channel (m) | 10 | |
| Time of retention (min:sec) | 0:28 | |
| Mean particle size (nm) | 95.5 | 61.78 |
| PdI | 0.084 | 0.065 |

The experiment shows that the particle size of lipid particles can be controlled by adjusting the temperature.

(Example 6) Relationship Between Back Pressure and Particle Size (6-1)
The following solutions were prepared.
Solution A: 96 mg of DOPC, 97 mg of DOPG, 90 mg of DPPC, 91 mg of DPPG, and 126 mg of Cholesterol were dissolved into 4 ml of ethanol
Solution B: maltose was dissolved into 10 mM sodium phosphate buffer (pH 6.5) at a final concentration of 10% (W/V).

A lipid particle producing apparatus was configured to allow solution A and solution B to flow on separate flow channels, mix the solutions with a first mixer to prepare a first diluting solution, allow the first diluting solution to flow in a liquid supplying tube, and mix the first diluting solution with solution B in a second mixer to prepare a second diluting solution. In this regard, solution A (4 mL/min) and solution B (9.3 mL/min) were mixed with the first mixer to prepare the first diluting solution with an ethanol concentration of 30% (V/V), and solution B (8.9 mL/min) was added and mixed with the second mixer to prepare the second diluting solution with an ethanol concentration of 18% (V/V).

Figure 18:
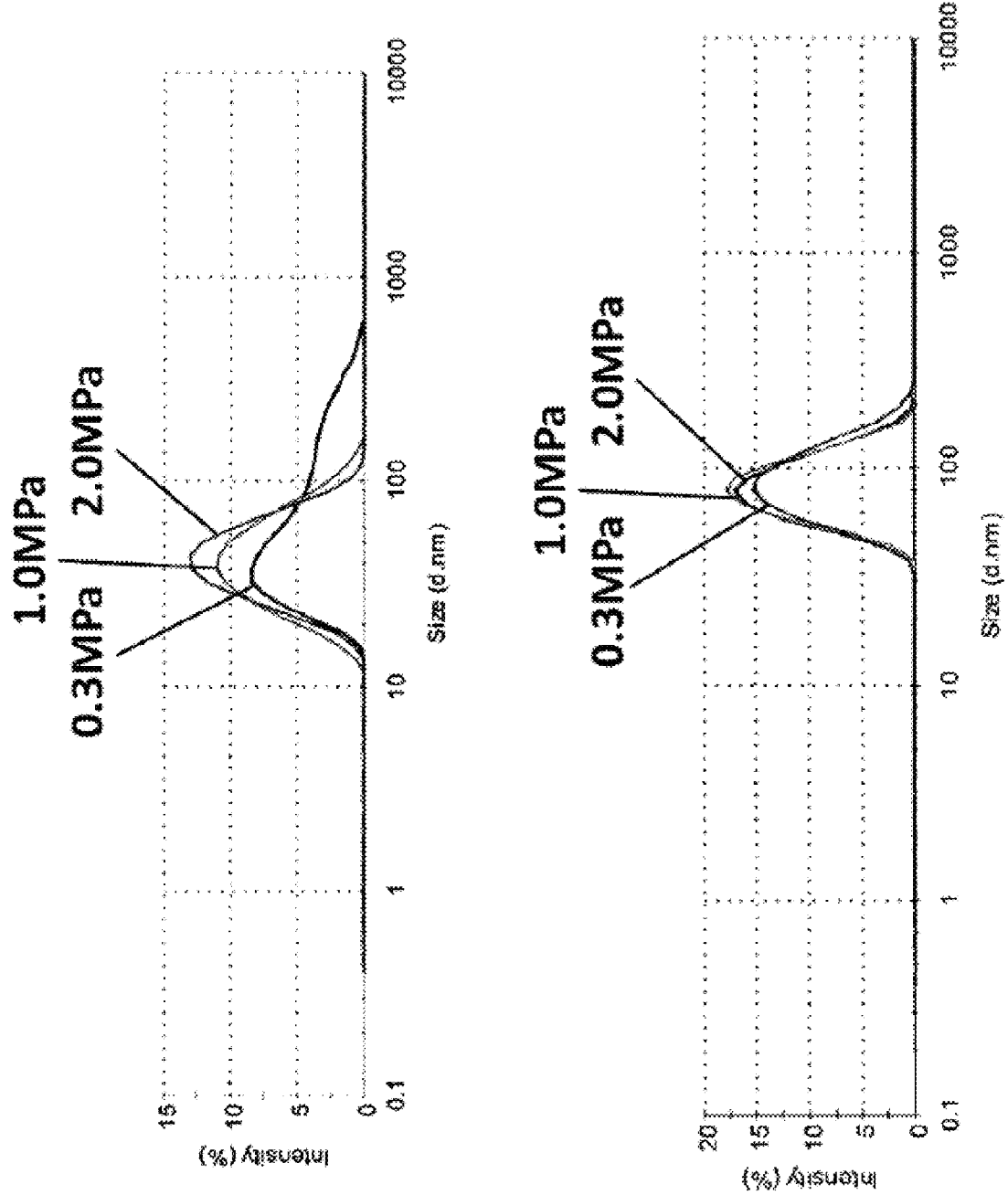
FIG. 18 is a diagram showing the particle size distribution of liposomes when the back pressure was changed.

The mean particle size and polydispersity index were observed after adjusting the back pressure in a flow channel between the first mixer and the second mixer to be 0.3 MPa, 1.0 MPa, or 2.0 MPa. The results are shown in the following table and the left side of FIG. 18.

TABLE 20

| Back pressure (MPa) | 0.3 | 1.0 | 2.0 |
|---|---|---|---|
| Particle size (nm) | 81.85 | 78.24 | 77.65 |
| PdI | 0.141 | 0.033 | 0.034 |

(6-2)
The following solutions were prepared.
Solution A: 144 mg of DOPC, 144 mg of DMPG, and 96 mg of Cholesterol were dissolved into 3 ml of ethanol
Solution B: maltose was dissolved into 10 mM sodium phosphate buffer (pH 6.5) at a final concentration of 10% (W/V).

A lipid particle producing apparatus was configured to allow solution A and solution B to flow on separate flow channels, mix the solutions with a first mixer to prepare a first diluting solution, allow the first diluting solution to flow in a liquid supplying tube, and mix the first diluting solution with solution B in a second mixer to prepare a second diluting solution. In this regard, solution A (3.06 mL/min) and solution B (13.5 mL/min) were mixed with the first mixer to prepare the first diluting solution with an ethanol concentration of 18.5% (V/V), and solution B (0.5 mL/min) was added and mixed with the second mixer to prepare the second diluting solution with an ethanol concentration of 18% (V/V).

The mean particle size and polydispersity index were observed after adjusting the back pressure in a flow channel between the first mixer and the second mixer to 0.3 MPa, 1.0 MPa, or 2.0 MPa. The results are shown in the following table and the right side of FIG. 18.

TABLE 21

| Back pressure (MPa) | 0.3 | 1.0 | 2.0 |
|---|---|---|---|
| Particle size (nm) | 50.76 | 37.19 | 38.22 |
| PdI | 0.279 | 0.175 | 0.138 |

These experiments show that the particle size of lipid particles and the PdI value are maintained at a low value and the uniformity of particle sizes is high when back pressure is 1.0 MPa or greater.

The experiments show that the particle size distribution of lipid particles can be controlled by adjusting the back pressure.

(Example 7) Controlling Particle Size with Combination of Elements

The following solutions were prepared.
Solution A: 95.8 mg of HSPC, 31.9 mg of Cholesterol, and 31.9 mg of MPEG 2000 DSPE were dissolved into 6 ml of ethanol
Solution B: maltose was dissolved into 10 mM sodium phosphate buffer (pH 6.5) at a final concentration of 10% (W/V).

A lipid particle producing apparatus was configured to allow solution A and solution B to flow on separate flow channels, mix the solutions with a first mixer to prepare a first diluting solution, allow the first diluting solution to flow in a liquid supplying tube so that the time of retention would be the time shown in the following table, and mix the first diluting solution with solution B in a second mixer to prepare a second diluting solution. In this regard, the flow volume was adjusted so that the ethanol concentrations (V/V) of the first diluting solution was 27%, 36%, 39%, and 45% and the ethanol concentration of the second diluting solution was 18% (V/V).

The mean particle size and polydispersity index were observed. The results are shown in the following table and FIG. 19.

TABLE 22

| First diluting solution 27% | | | |
|---|---|---|---|
| Time of retention (min:sec) | 0:30 | 3:00 | 15:00 |
| Mean particle size (nm) | 63.96 | 74.32 | 79.27 |
| PdI | 0.085 | 0.083 | 0.078 |
| After 1 hour Mean particle size (nm) | 69.55 | 73.18 | 77.53 |
| PdI | 0.136 | 0.073 | 0.021 |
| After 1 day Mean particle size (nm) | 67.08 | 74.05 | 77.13 |
| PdI | 0.067 | 0.08 | 0.051 |
| Stability | ○ | ○ | ○ |

TABLE 23

| First diluting solution 36% | | | |
|---|---|---|---|
| Time of retention (min:sec) | 0:30 | 3:00 | 15:00 |
| Mean particle size (nm) | 81.78 | 90.98 | 99.37 |
| PdI | 0.057 | 0.035 | 0.047 |
| After 1 hour Mean particle size (nm) | 85.29 | 96 | 104.1 |
| PdI | 0.076 | 0.077 | 0.027 |
| After 2 days Mean particle size (nm) | 84.44 | 88.9 | 106.6 |
| PdI | 0.069 | 0.039 | 0.022 |
| Stability | ○ | ○ | ○ |

TABLE 24

| First diluting solution 39% | | | |
|---|---|---|---|
| Time of retention (min:sec) | 0:30 | 3:00 | 15:00 |
| Mean particle size (nm) | 92.32 | 98.29 | 114.8 |
| PdI | 0.07 | 0.083 | 0.07 |
| After 1 hour Mean particle size (nm) | 93.3 | 100.1 | 116.5 |
| PdI | 0.067 | 0.055 | 0.053 |

TABLE 24-continued

| | First diluting solution 39% | | | |
|---|---|---|---|---|
| After 2 days | Mean particle size (nm) | 96.06 | 101.7 | 121.5 |
| | Pdl | 0.079 | 0.066 | 0.045 |
| Stability | | ○ | ○ | ○ |

TABLE 25

| | First diluting solution 45% | | | |
|---|---|---|---|---|
| Time of retention (min:sec) | | 0:30 | 3:00 | 15:00 |
| Mean particle size (nm) | | 112 | 150.3 | 178.4 |
| Pdl | | 0.046 | 0.027 | 0.087 |
| After 1 hour | Mean particle size (nm) | 116.5 | 152.6 | 182.7 |
| | Pdl | 0.035 | 0.013 | 0.047 |
| After 2 days | Mean particle size (nm) | 118.8 | 154.5 | 186.6 |
| | Pdl | 0.047 | 0.018 | 0.049 |
| Stability | | ○ | ○ | ○ |

The particle size of lipid particles was able to be controlled over a wide range (70 to 180 nm) while maintaining the granularity distribution by adjusting the ethanol concentration of the primary dilution and time of retention.

Example 8: Preparation of Micelles with a Desired Particle Size

Micelles can also prepared in a similar manner. Lipid particles comprising many micelles were prepared in the following manner.
The following solutions were prepared.
Solution A: 96 mg of DOPC, 97 mg of DOPG, 90 mg of DPPC, 91 mg of DPPG, and 126 mg of Cholesterol were dissolved into 4 ml of ethanol
Solution B: maltose was dissolved into 10 mM sodium phosphate buffer (pH 6.5) at a final concentration of 10% (W/V).
A lipid particle producing apparatus was configured to allow solution A and solution B to flow on separate flow channels, mix the solutions with a first mixer to prepare a first diluting solution, allow the first diluting solution to flow in a liquid supplying tube, and mix the first diluting solution with solution B in a second mixer so that the time of retention would be the time shown in the following table to prepare a second diluting solution. In this regard, the flow volume was adjusted so that the ethanol concentrations (V/V) of the first diluting solution was 25% and 36% and the ethanol concentration of the second diluting solution was 18% (V/V). In this regard, the time of retention from mixing of the first diluting solution to the mixing of the second diluting solution was adjusted to be 15 seconds when using the first diluting solution with an ethanol concentration of 25% and 2 minutes and 50 seconds when using a first diluting solution with an ethanol concentration of 36%. The mean particle size and polydispersity index were observed for these lipid particles. The results are shown in FIG. 20C. The mean particle sizes of lipid particle preparations were 36 nm (first diluting solution: 25%) and 110 nm (first diluting solution: 36%).

TABLE 26

| Time of retention | 15 seconds | 2 minutes and 50 seconds |
|---|---|---|
| Ethanol concentration % (V/V) | 25% | 36% |
| Mean particle size (nm) | 36.11 | 110.41 |
| Pdl | 0.075 | 0.104 |
| Micelle (%) | 73.1 | 7.2 |

The lipid bilayer structure was stained with phosphotungstic acid stain and observed with a transmission electron microscope (H-7600, Hitachi, Ltd., Tokyo) (FIGS. 20A and 20B). In view of the observation results, about 70% of preparations with a mean particle size of 36 nm did not exhibit a lipid bilayer structure, suggesting that the structure was a lipid nanoparticle (LNP) structure. These LNPs are expected to have a micelle structure with a cholesterol core.

In this manner, the present invention was also able to provide micelles. The micelles can also be controlled to have a desired particle size and/or polydispersity index.

In the same manner as Examples 1-7, the correlation with the particle size of micelles is analyzed for each of the following conditions: first stage alcohol dilution concentration; second stage alcohol dilution concentration; time elapsed after first stage alcohol dilution; temperature; and back pressure. Micelles with a desired mean particle size and polydispersity index are prepared based on such analysis results. It can be advantageous that the first stage alcohol concentration is low for the formation of micelles. To control the particle size of micelles, it can be conversely advantageous to increase the second stage alcohol concentration to promote fusion among micelles. The second diluting solution can be further diluted by adding a third mixer to adjust the alcohol concentration to 18% (V/V) or less for stabilization. For example, the particle size of micelles can also be controlled by controlling the time of retention (e.g., time of retention between the second mixer and the third mixer) in the same manner as liposomes.

Example 9: Determination of Conditions for Preparing Lipid Particles with a Desired Particle Size Loaded with a Drug For a given drug A, a condition for producing lipid particles (liposomes or micelles) loaded with drug A to have a mean particle size X nm (and polydispersity index Y as need) is determined.
Procedure 1) A solution comprising drug A, a given lipid, and specific alcohol is mixed with another solution comprising water to prepare a mixture with alcohol diluted to a predetermined concentration. In this regard, at least 2 predetermined concentrations are selected within the range of 20 wt % to 50 wt %. For each mixture, the particle size of lipid particles is measured when a certain period of time has elapsed after the preparation (can be immediately after preparation). A function representing the relationship between the mean particle size (and polydispersity index as needed) of lipid particles and dilution concentration is created based on the measurement results.
Procedure 2) Procedure 2 is performed after or in parallel with Procedure 1. A solution comprising drug A, a given lipid, and specific alcohol is mixed with another solution comprising water to prepare a mixture with alcohol diluted to a certain concentration. The particle size of lipid particles is measured when a predetermined time has elapsed after preparation of the mixture. In this regard, at least 2 predetermined times are selected within the range of 0 minutes to 1 hour after preparation. A function representing the relationship between the mean particle size (and polydispersity index as needed) of lipid particles and time elapsed after preparation is created based on the measurement results.

The functions created in Procedure 1 and Procedure 2 are used to determine the alcohol dilution concentration and predetermined time (time of retention) after dilution, or define the range of alcohol dilution concentration and predetermined time (time of retention) after dilution to select a suitable point therein, so that the lipid particles have a desired mean particle size (and polydispersity index as needed).

(Note)

As disclosed above, the present invention has been exemplified by the use of its preferred embodiments. However, it is understood that the scope of the present invention should be interpreted based solely on the Claims. It is also understood that any patent, patent application, and references cited herein should be incorporated herein by reference in the same manner as the contents are specifically described herein.

INDUSTRIAL APPLICABILITY

The present invention can be used for formulation of drugs.

The invention claimed is:

1. A method of manufacturing a lipid particle with a desired particle size, the method comprising:
   (A) preparing a primary diluting solution by mixing a first solution comprising a lipid and alcohol with a second solution comprising water in a first mixing region;
   (B) supplying the primary diluting solution from the first mixing region to a second mixing region through a liquid supplying tube in a predetermined time; and
   (C) preparing a secondary diluting solution by mixing the primary diluting solution with a third solution comprising water in the second mixing region;
   wherein steps (A) to (C) are performed sequentially, and
   wherein a particle size of a lipid particle is controlled by adjusting at least one condition including the predetermined time
   wherein the lipid particle is further loaded with a drug, and wherein the method further comprises, before step (A):
   (A-1) measuring a chronological change in a particle size of a lipid particle loaded with the drug under a condition where the concentration of the alcohol is constant;
   wherein at least one condition required for adjusting the desired particle size including the predetermined time is determined based on information obtained by step (A-1).

2. The method of claim 1, wherein the particle size of the lipid particle is controlled by further adjusting at least one condition selected from the group consisting of a concentration of the alcohol, a concentration of the lipid, and a temperature upon the mixing.

3. The method of claim 1, the predetermined time is adjusted in the range of 0.1 to 60 minutes.

4. The method of claim 1, which manufactures lipid particles with a particle size distribution with a PDI of less than 0.1.

5. The method of claim 1, wherein the adjusting the predetermined time comprises selecting a tube having a predetermined length as the liquid supplying tube.

6. The method of claim 5, wherein the length of the liquid supplying tube is adjusted between 10 m to 40 m.

7. The method of claim 1, wherein the adjusting the predetermined time comprises adjusting flow rate in the liquid supplying tube.

8. The method of claim 1, wherein the lipid particle is a liposome or a micelle.

9. The method of claim 1, wherein the method further comprises, before step (A):
   (A-2) measuring a particle size of a lipid particle formed when a concentration of the alcohol is changed by diluting a solution comprising the drug, the lipid, and the alcohol;
   wherein the at least one condition required for adjusting the desired particle size selected from the group consisting of the concentration of the alcohol in the primary diluting solution, the concentration of the lipid, the predetermined time, and the temperature upon the mixing is determined based on information obtained by step (A-2) together with the information obtained by step (A-1).

10. The method of claim 1, wherein the alcohol concentration in the primary diluting solution is adjusted to 18 wt % or greater.

11. The method of claim 1, wherein steps (A) to (C) are performed in a closed system.

12. The method of claim 1, wherein additional particle size controlling processing is not performed after step I.

13. The method of claim 1, wherein a pressure in the liquid supplying tube is 1 Mpa or greater.

14. The method of claim 1, wherein the secondary diluting solution is further supplied to a hollow fiber membrane column.

* * * * *